(12) United States Patent
Baltezor et al.

(10) Patent No.: US 10,398,646 B2
(45) Date of Patent: Sep. 3, 2019

(54) METHODS FOR TREATING LUNG DISORDERS

(71) Applicant: CRITITECH, INC., Lawrence, KS (US)

(72) Inventors: Michael Baltezor, Lawrence, KS (US); Matthew McClorey, Lawrence, KS (US); William Johnston, Lawrence, KS (US); Gere S. diZerega, Lawrence, KS (US); James Verco, Lawrence, KS (US)

(73) Assignee: CritiTech, Inc., Lawrence, KS (US)

( * ) Notice: Subject to any disclaimer, the term of this patent is extended or adjusted under 35 U.S.C. 154(b) by 0 days.

(21) Appl. No.: 16/007,095

(22) Filed: Jun. 13, 2018

(65) Prior Publication Data

US 2018/0360748 A1    Dec. 20, 2018

Related U.S. Application Data

(60) Provisional application No. 62/678,387, filed on May 31, 2018, provisional application No. 62/653,942, (Continued)

(51) Int. Cl.
| | |
|---|---|
| *A61K 9/00* | (2006.01) |
| *A61P 11/00* | (2006.01) |
| *A61P 35/00* | (2006.01) |
| *A61K 9/16* | (2006.01) |
| *A61K 9/10* | (2006.01) |

(Continued)

(52) U.S. Cl.
CPC .............. *A61K 9/0078* (2013.01); *A61K 9/10* (2013.01); *A61K 9/14* (2013.01); *A61K 9/1611* (2013.01); *A61K 9/1623* (2013.01); *A61K 31/337* (2013.01); *A61K 47/02* (2013.01); *A61K 47/26* (2013.01); *A61P 11/00* (2018.01); *A61P 35/00* (2018.01)

(58) Field of Classification Search
None
See application file for complete search history.

(56) References Cited

U.S. PATENT DOCUMENTS 5,399,363 A * 3/1995 Liversidge ............. A61K 9/145
424/489
5,833,891 A    11/1998 Subramaniam et al.
(Continued)

FOREIGN PATENT DOCUMENTS

| CN | 1463969 A | 12/2003 |
|---|---|---|
| CN | 1923189 A | 3/2007 |

(Continued)

OTHER PUBLICATIONS

Mayo Clinic Patient Care and Health Information regarding cystic fibrosis, accessed online Sep. 10, 2018. (Year: 2018).*

(Continued)

*Primary Examiner* — Robert A Wax
*Assistant Examiner* — Melissa S Mercier
(74) *Attorney, Agent, or Firm* — McDonnell Boehnen Hulbert & Berghoff LLP

(57) ABSTRACT

Disclosed herein are compositions and methods for treating lung disorders including lung tumors by pulmonary administration of compositions comprising taxane particles such as docetaxel or paclitaxel particles.

20 Claims, 29 Drawing Sheets

Lung and plasma levels of Paclitaxel

Related U.S. Application Data filed on Apr. 6, 2018, provisional application No. 62/628,582, filed on Feb. 9, 2018, provisional application No. 62/519,257, filed on Jun. 14, 2017.

(51) Int. Cl.
  *A61K 31/337* (2006.01)
  *A61K 47/02* (2006.01)
  *A61K 47/26* (2006.01)
  *A61K 9/14* (2006.01)

(56) References Cited

U.S. PATENT DOCUMENTS

| | | | |
|---|---|---|---|
| 5,874,029 A | 2/1999 | Subramaniam et al. | |
| 6,113,795 A | 9/2000 | Subramaniam et al. | |
| 6,348,209 B2* | 2/2002 | Placke | A61K 9/0073 424/422 |
| 6,419,901 B2 | 7/2002 | Placke et al. | |
| 6,562,952 B1 | 5/2003 | Rajewski et al. | |
| 6,620,351 B2 | 9/2003 | Gupta et al. | |
| 6,689,803 B2 | 2/2004 | Hunter | |
| 6,811,767 B1 | 11/2004 | Bosch et al. | |
| 7,217,735 B1 | 5/2007 | Au et al. | |
| RE40,493 E | 9/2008 | Straub et al. | |
| 7,556,798 B2* | 7/2009 | Edwards | A61K 9/0075 128/203.15 |
| 7,744,923 B2 | 6/2010 | Rajewski et al. | |
| 7,820,788 B2 | 10/2010 | Desai et al. | |
| 8,138,229 B2 | 3/2012 | Desai et al. | |
| 8,221,779 B2 | 7/2012 | Jonas et al. | |
| 8,314,156 B2 | 11/2012 | Desai et al. | |
| 8,778,181 B1 | 7/2014 | Johnson et al. | |
| 8,906,392 B2 | 12/2014 | Berkland et al. | |
| 9,233,348 B2 | 1/2016 | Johnson et al. | |
| 9,278,069 B2 | 3/2016 | Berkland et al. | |
| 9,763,946 B2 | 9/2017 | Lin | |
| 9,814,685 B2* | 11/2017 | Baltezor | A61K 9/1605 |
| 9,895,197 B2* | 2/2018 | Poquet | A61B 90/50 |
| 9,918,957 B2 | 3/2018 | Baltezor | |
| 2002/0102294 A1 | 8/2002 | Bosch et al. | |
| 2003/0166509 A1 | 9/2003 | Edwards et al. | |
| 2003/0190284 A1 | 10/2003 | Annapragada et al. | |
| 2004/0033267 A1 | 2/2004 | Merisko-Liversidge et al. | |
| 2004/0092577 A1 | 5/2004 | Lerner et al. | |
| 2005/0238725 A1* | 10/2005 | Cunningham | A61K 9/145 424/489 |
| 2006/0147535 A1 | 7/2006 | Muthukumaran et al. | |
| 2006/0188566 A1* | 8/2006 | Liversidge | A61K 9/0019 424/451 |
| 2008/0160095 A1 | 7/2008 | Desai et al. | |
| 2012/0087984 A1 | 4/2012 | Liversidge et al. | |
| 2012/0237768 A1 | 9/2012 | Hirokawa et al. | |
| 2015/0342872 A1 | 12/2015 | Williamson et al. | |
| 2015/0375153 A1 | 12/2015 | Johnson et al. | |
| 2016/0263232 A1 | 9/2016 | Amighi et al. | |
| 2016/0374953 A1 | 12/2016 | Baltezor | |
| 2018/0169058 A1 | 6/2018 | Baltezor | |

FOREIGN PATENT DOCUMENTS

| | | |
|---|---|---|
| CN | 101336899 A | 1/2009 |
| CN | 101829061 A | 9/2010 |
| PT | 104693 A | 1/2011 |
| WO | 2000/57852 A2 | 10/2000 |
| WO | 2000/72827 A2 | 12/2000 |
| WO | 2003/032906 A2 | 4/2003 |
| WO | 2004/089291 A2 | 10/2004 |
| WO | 2006/068890 A2 | 6/2006 |
| WO | 2007/027941 A2 | 3/2007 |
| WO | 2008/137148 A2 | 11/2008 |
| WO | 2009/111271 A1 | 9/2009 |
| WO | 2012/051426 A2 | 4/2012 |
| WO | 2017/176628 | 10/2017 |

OTHER PUBLICATIONS

Goel et al. (Exploring targeted pulmonary delivery for treatment of lung cancer, Int J. Pharm Investig. Jan.-Mar. 2013; 3(1): 8-14) (Year: 2013).*

Pazdur et al. (The toxoids: paclitaxel (Taxol) and docetaxel (Taxotere), Cancer Treatment Reviews, vol. 19, Issue 4, Oct. 1993, pp. 351-386. (Year: 1993).*

Gruden et al., "Antitumoral effect and reduced systemic toxicity in mice after intra-tumoral injection of an in vivo solidifying calcium sulfate formulation with docetaxel", European Journal of Pharmaceutics and Biopharmaceutics, 114 (2017); 186-193.

Kakran Mitali, et al., "Modified supercritical antisolvent method with enhanced mass transfer to fabricate drug nanoparticles," Materials Science and Engineering, 33(5): 2864-2870, Mar. 2013.

Lee, et al., "Supercritical antisolvent production of biodegradable micro-and nanoparticles for controlled delivery of paclitaxel," Journal of Controlled Release, 125(2): 96-106, Oct. 2007.

International Search Report and Written Opinion for PCT/US2016/035993, dated Sep. 19, 2016.

Williamson, et al., "Phase I clinical trial of the intraperitoneal (IP) administration of a novel nanoparticle formulation of paclitaxel (NTX)," Poster Presentation, ACS, Sep. 2013.

Johnston, et al., "Nanotax Injectable Nanocystal Paclitaxel for Ovarian and Other Intraperitoneal Cancers," Datasheet, Sep. 2013.

Bouquet, et al., "Drug Delivery of paclitaxel for an intraperitoneal chemotherapy," Thesis, 2009.

Merisko-Liversidge, et al., "Formulation and Antitumor Activity Evaluation of Nanocrystalline Suspensions of Poorly Soluble Anticancer Drugs," Pharmaceutical Research, 13(2): 272- 278, 1996.

Sharma, et al., "Development of Stabilized Paclitaxel nanocrystals: In vitro and in vivo efficacy studies," European Jounral of Pharmaceuticals Science, 69: 51-60, Jan. 2015.

Pankaj, et al., Nanosized Paclitaxel Particles from Supercritical Carbon Dioxide Processing and Their Biological Evaluation, Langmuir, 23(5): 2674-2679, Feb. 2007.

Della Porta and Reverchon, "Engineering Powder Properties by supercritical fluid for optimum Drug Delivery, Part One: Supercritical Antisolvent Precipitation," BioProcessTechnical, Feb. 2005, 48-52.

Della Porta and Reverchon, Engineering Powder Properties by supercritical fluid for optimum Drug Delivery, Part Two: Supercritical-Assisted Atomization, BioProcess Technical, Mar. 2005, 54-60.

Charoenchaitrakool, et al., "Micronization by Rapid Expansion of Supercritical Solutions to Enhance the Dissolution Rates of Poorly Water-Soluble Pharmaceuticals," Ind Eng Chem Res, 2000, 39: 4794-4802.

Werth, et al., "Agglomeration of Charged Nanopowders in Suspensions," Phys Rev E Stat Nonlin Soft Matter Phys. Feb. 2006;73(2 Pt 1):021402. Epub Feb. 10, 2006.

Rasenack, et al., Micronization of Anti-Inflammatory Drugs for Pulmonary Delivery by a Controlled Crystallization Process, J Pharm Sci, 92:35-44, 2003.

Castellanos, "The relationship between attractive interparticles forces and bulk behaviors in dry and uncharged fine powders," Advances in Physics, 54(4): 263-376, 2005.

Snavely, et al., "Micronization of insulin from halogenated alcohol solution using supercritical carbon dioxide as an antisolvent," J Pharm Sci, 91:2026-2039, 2002.

Vemavarapu, Particle formation by rapid expansion of supercritical solutions, Dissertation 2002.

Podczeck, "The Influence of Particle Size Distribution and Surface Roughness of Carrier Particles on the in vitro Properties of Dry Powder Inhalations," Aerosol Science and Technology, 31(4): 301-321, 1999.

Young, Characterisation of particle-particles interactions using the atomic force microscope, Dissertation, 2002.

Barura, et al "Challenges associated with penetration of nanoparticles across cell and tissue barriers: A review of current status and future prospects," Nano Today, 9: 223-243, 2014.

(56) References Cited

OTHER PUBLICATIONS

Carbone, et al "Non-Small Cell Lung Cancer: Role of the Immune System and Potential for Immunotherapy," J Thorac Oncol, 10(7): 974-984, 2015.
Desai, et al, "Pulmonary delivery of a novel, cremophor-free, protein-based nanoparticle preparation of paclitaxel," Proceedings of the American Association for Cancer Research, 44: 731-732, Abstract 2003.
Hershey, et al, "Inhalation Chemotherapy for Macroscopic Primary or Metastatic Lung Tumors: Proof of Principle Using Dogs with Spontaneously Occurring Tumors as a Model," Clinical Cancer Research, 5:2653-2659, 1999.
Hiraoka, et al, "Concurrent infiltration by CD8+T cells and CD4+T cells is a favourable prognostic factor in non-small-cell lung carcinoma," British Journal of Cancer, 94: 275-280, 2006.
Hohenforst-Schmidt, "Intratumoral chemotherapy for lung cancer: re-challenge current targeted therapies," Drug Design, Development and Therapy, 571-583, 2013.
Koshkina, et al "Paclitaxel Liposome Aerosol Treatment Induces Inhibition of Pulmonary Metastases in Murine Renal Carcinoma Model," Clinical Cancer Research, 7: 3258-3262, Mar. 2001.
Koshkina, et al, "Improved respiratory delivery of the anticancer drugs, camptothecin and paclitaxel, with 5% CO2-enriched air: pharmacokinetic studies," Cancer Chemother Pharmacol, 47: 451-456, Oct. 2001.
Koshkina, et al, "Cyclosporin A Aerosol Improves the Anticancer Effect of Paclitaxel Aerosol in Mice," Journal of Aerosol Medicine, 17(1): 7-14, 2004.
Kulkarni, et al, "The Use of Systemic Treatment in the Maintenance of Patients with Non-Small Cell Lung Cancer: A Systematic Review," Journal of Thoracic Oncology, 11(7): 989-1002, 2016.
Liu, et al, "Paclitaxel Nanocrystals for Overcoming Multidrug Resistance in Cancer," Mol Pharm, 7(3): 863-869, 2010.
Liu, et al, "Enabling Anticancer Therapeutics by Nanoparticle Carriers: The Delivery of Paclitaxel," Int J. Mol. Sci., 12:4395-4413, 2011.
Mallow, et al, Broncho-Adventitial Delivery of Paclitaxel to Extend Airway Patency in Malignant airway Obstruction (broadway trial), Advances in Thoracic Oncologic Diagnostics, Abstract May 2017.
Polo, et al, "Maintenance strategies in stage IV non-small-cell lung cancer (NSCLC): in which patients, with which drugs?" Annals of Oncology 25: 1283-1293, Dec. 2013.
Wakabayashi, et al, "CD4+ T cells in cancer stroma, not CD8+ T cells in cancer cell nests, are associated with favorable prognosis in human non-small cell lung cancers," Cancer Sci, 94(11): 1003-1009, Nov. 2003.
Xing, et al, "Efficacy and safety of albumin-bound paclitaxel in treating recurrent advanced non-small-cell lung cancer," Chinese Journal of Cancer Research, 25(2):200-205, 2013.
Zarogoulidis, et al, "Inhaled chemotherapy in lung cancer: future concept of nanomedicine," International Journal of Nanomedicine, 7: 1551-1572, Mar. 2012.
Zhou, "Atomized paclitaxel liposome inhalation treatment of bleomycin-induced pulmonary fibrosis in rats," Genetics and Molecular Research, 15(2): 1-11, 2016.
International Search Report for PCT/US2018/037219, dated Aug. 21, 2018.
Shikanov et al: "Paclitaxel tumor biodistribution and efficacy after intratumoral injection of a biodegradable extended release implant", International Journal of Pharmaceutics, 358 (2008) 114-120.

* cited by examiner

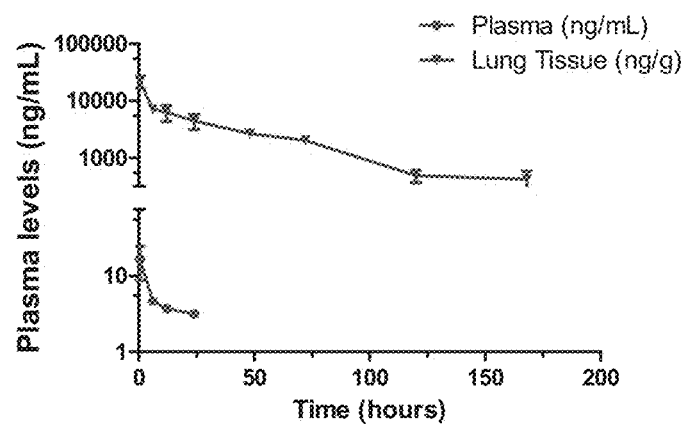
Figure 1. Lung and plasma levels of Paclitaxel
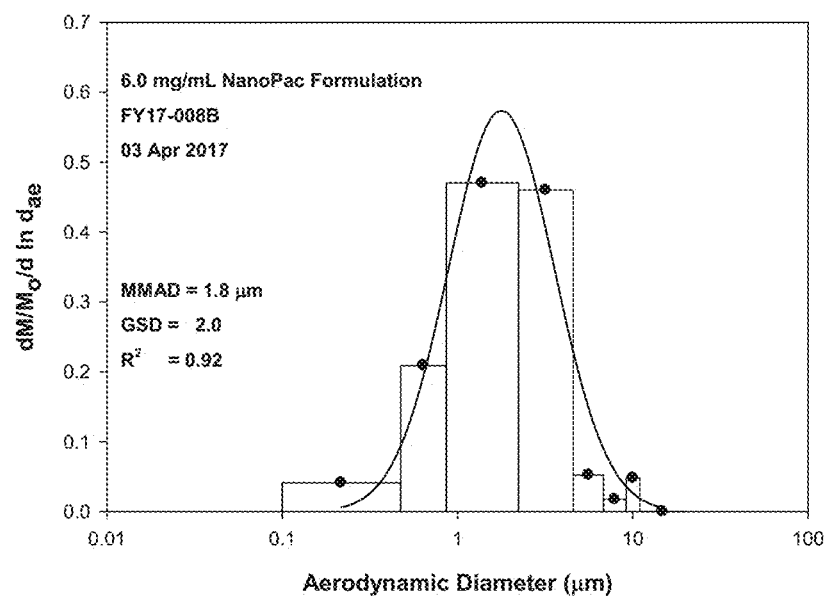
Figure 2

Figure 3: Particle size distribution for 20.0 mg/mL NANOPAC® formulation aerosols as measured by cascade impactor.

Data from PK Study FY17-008B showing amount of paclitaxel in plasma over time.

Data from PK Study FY17-008B showing amount of paclitaxel in lung tissue over time.

Data from Pilot PK Study FY17-008A (Example 1) for reference (0.33 mg/kg (ng/mL)

* indicates P> 0.05 and ** indicates P> 0.01

* indicates P> 0.05 and ** indicates P> 0.01

* indicates P> 0.05 and ** indicates P> 0.01

1006 (Control) Adenocarcinoma-3, Primitive-1, Regression-0. Primary characteristics of the lung tumor masses.
(2x)

1006 (Control) Adenocarcinoma-3, Primitive-1, Regression-0. Primary characteristics of undifferentiated cells within the lung tumor masses.

1006 (Control) Adenocarcinoma-3, Primitive-1, Regression-0. Primary characteristics of undifferentiated cells within the lung tumor masses.

1006 (Control) Adenocarcinoma-3, Primitive-1, Regression-0. Primary characteristics of undifferentiated cells within the lung tumor masses showing masses within alveolar spaces. a(20x)

1006 (Control) Adenocarcinoma-3, Primitive-1, Regression-0. Primary characteristics of primitive cells within the lung tumor masses. b(10x)

1006 (Control) Adenocarcinoma-3, Primitive-1, Regression-0. Primary characteristics of primitive cells within the lung tumor masses. b20x 1006 (Control) Adenocarcinoma-3, Primitive-1, Regression-0. Primary characteristics of primitive cells within the lung tumor masses. b(40x)

1006 (Control) Adenocarcinoma-3, Primitive-1, Regression-0 bronchiole. Primary characteristics of undifferentiated cells showing within bronchiole. c(10x)

1006 (Control) Adenocarcinoma-3, Primitive-1, Regression-0 bronchiole. Primary characteristics of undifferentiated cells showing within bronchiole. c(20x)

1006 (Control) Adenocarcinoma-3, Primitive-1, Regression-0 glands. Primary characteristics of acinar gland differentiation within the lung tumor masses. d(10x)

1006 (Control) Adenocarcinoma-3, Primitive-1, Regression-0 glands. Primary characteristics of acinar gland differentiation within the lung tumor masses. d(20x)

2001 (IV Abraxane) Adenocarcinoma-2, Primitive-1, Regression-0. Primary characteristics of the lung tumor mass pushing underneath a bronchiole and showing no evidence of intravascular invasion. (2x)

2001 (IV Abraxane) Adenocarcinoma-2, Primitive-1, Regression-0. Primary characteristics of the lung tumor mass pushing underneath a bronchiole and showing no evidence of intravascular invasion. (4x)

2001 (IV Abraxane) Adenocarcinoma-2, Primitive-1, Regression-0. Primary characteristics of the lung tumor mass pushing underneath a bronchiole. (10x)

2003 (IV Abraxane) Adenocarcinoma-1, Primitive-1, Regression-1. Characteristics of the lung tumor masses undergoing regression. (4x)

2003 (IV Abraxane) Adenocarcinoma-1, Primitive-1, Regression-1. Characteristics of the lung tumor masses undergoing regression. (10x)

2003 (IV Abraxane) Adenocarcinoma-1, Primitive-1, Regression-1. Characteristics of the lung tumor masses undergoing regression. (20x)

2003 (IV Abraxane) Adenocarcinoma-1, Primitive-1, Regression-1. Characteristics of the lung tumor masses undergoing regression. Note lymphocytes and macrophages along the edge. 1(40x)

2003 (IV Abraxane) Adenocarcinoma-1, Primitive-1, Regression-1. Characteristics of the lung tumor masses undergoing regression. Note lymphocytes and macrophages along the edge. 2(40x)

2003 (IV Abraxane) Adenocarcinoma-1, Primitive-1, Regression-1. Characteristics of the lung tumor masses undergoing regression. Note larger foamy and pigmented macrophages. 2, 2 x(40x)

2010 (IV Abraxane) Adenocarcinoma-3, Primitive-1, Regression-0. Primary characteristics of the lung tumor masses. (2x)

2010 (IV Abraxane) Adenocarcinoma-3, Primitive-1, Regression-0. Primary characteristics of the lung tumor masses. (20x)

2010 (IV Abraxane) Adenocarcinoma-3, Primitive-1, Regression-0. Primary characteristics of the lung tumor masses. Note subtle evidence of macrophages along the edge. (40x)

4009 (IH NanoPac 1x High) Adenocarcinoma-0, Primitive-0, Regression-4. Characteristics of the lung tumor masses that have undergone complete regression. (2x)

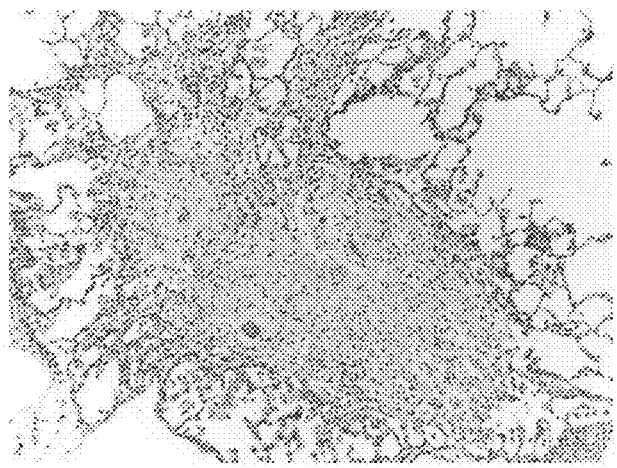

4009 (IH NanoPac 1x High) Adenocarcinoma-0, Primitive-0, Regression-4. Characteristics of a lung tumor mass that has undergone complete regression. Note stromal fibrosis. (10x)

FIG. 40

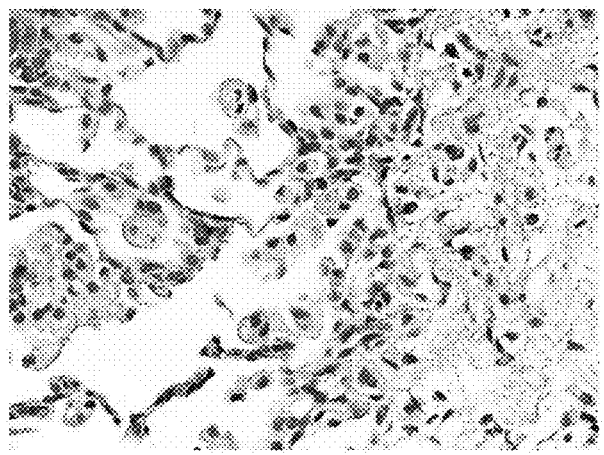

4009 (IH NanoPac 1x High) Adenocarcinoma-0, Primitive-0, Regression-4. Characteristics of a lung tumor mass that has undergone complete regression. Note stromal fibrosis, and lymphocytes and macrophages along the edge. (40x)

FIG. 41

5010 (IH NanoPac 2x Low) Adenocarcinoma-1, Primitive-0, Regression-3. Characteristics of the lung tumor masses undergoing regression. (2x)

5010 (IH NanoPac 2x Low) Adenocarcinoma-1, Primitive-0, Regression-3. Characteristics a lung tumor mass that is undergoing regression. (10x)

5010 (IH NanoPac 2x Low) Adenocarcinoma-1, Primitive-0, Regression-3. Characteristics a lung tumor mass that is undergoing regression. (20x)

5010 (IH NanoPac 2x Low) Adenocarcinoma-1, Primitive-0, Regression-3. Characteristics a lung tumor mass that is undergoing regression. (40x)

6005 (IH NanoPac 2x High) Adenocarcinoma-1, Primitive-0, Regression-4. Characteristics a lung tumor mass that is undergoing regression. (2x)

6005 (IH NanoPac 2x High) Adenocarcinoma-1, Primitive-0, Regression-4. Characteristics a lung tumor mass that is undergoing regression. Note stromal fibrosis, and lymphocytes and macrophages along the edge. (10x)

6005 (IH NanoPac 2x High) Adenocarcinoma-1, Primitive-0, Regression-4. Characteristics a lung tumor mass that is undergoing regression. Note lymphocytes and macrophages along the edge. (20x)

6005 (IH NanoPac 2x High) Adenocarcinoma-1, Primitive-0, Regression-4. Note lymphocytes and macrophages along the edge. (40x)

6005 (IH NanoPac 2x High) Adenocarcinoma-1, Primitive-0, Regression-4. Note the presence of a focal area of residual tumor cells within an alveolus. 2(40x)

METHODS FOR TREATING LUNG DISORDERS

CROSS REFERENCE

This application claims priority to U.S. Provisional Patent Application Ser. Nos. 62/519,257 filed Jun. 14, 2017; 62/628,582 filed Feb. 9, 2018; 62/653,942 filed Apr. 6, 2018; and 62/678,387 filed May 31, 2018, each incorporated by reference herein in their entirety.

BACKGROUND

Lung cancer is the second most common cancer and one of the most lethal. Conventional therapies such as surgical resection, radiation, and chemotherapy have not resulted in satisfactory long-term survival rates. Systemic drug delivery, even at a high dose, results in only a limited amount of taxane drugs reaching lung tumors. Improved methods for treating lung tumors are thus needed.

SUMMARY OF THE INVENTION

In one aspect, the invention provides methods for treating a lung disorder, such as a lung tumor or pulmonary fibrosis, comprising pulmonary administration to a subject with a lung disorder of an amount effective of a composition comprising taxane particles to treat the lung disorder, wherein the taxane particles comprise at least 95% of the taxane and have a mean particle size (number) of between 0.1 μm and 5 μm. In one embodiment, the pulmonary administration may comprise nebulization, wherein the nebulizing results in pulmonary delivery to the subject of aerosol droplets of the taxane particles or suspension thereof. In another embodiment, the taxane particles may have a mean particle size (number) of between 0.4 μm and 2 μm. In further embodiments, the taxane particles may have a mean particle size (number) of between about 0.4 μm and about 1.2 μm, or between about 0.6 μm and about 1.0 μm.

In another embodiment, the taxane particles may have a specific surface area (SSA) of at least 10 $m^2/g$, or at least 12 $m^2/g$, 14 $m^2/g$, 16 $m^2/g$, 18 $m^2/g$, 20 $m^2/g$, 25 $m^2/g$, 30 $m^2/g$, 32 $m^2/g$, 34 $m^2/g$, or 35 $m^2/g$; or wherein the taxane particles have an SSA of between about 10 $m^2/g$ and about 60 $m^2/g$. In another embodiment, the taxane particles may be present in a suspension, wherein the suspension comprises:

(a) the taxane particles;
(b) a pharmaceutically acceptable carrier; and
(c) a polysorbate, wherein the polysorbate is present in the suspension at a concentration of between about 0.01% v/v and about 1.5% v/v, or between about 0.01% v/v and about 1% v/v, about 0.01% v/v and about 0.5% v/v, about 0.01% v/v and about 0.4% v/v, about 0.01% v/v and about 0.25% v/v, about 0.05% v/v and about 0.5% v/v, about 0.05% v/v and about 0.25% v/v, about 0.1% v/v and about 0.5% v/v, about 0.1% v/v and about 0.25% v/v, about 0.1% v/v, about 0.16 v/v, or about 0.25% v/v. In one embodiment, the pharmaceutically acceptable carrier may be saline, such as 0.9% sodium chloride solution. In another embodiment, the polysorbate may be polysorbate 80. In a further embodiment, the taxane may be present in the suspension at a concentration between about 1 mg/ml and about 40 mg/ml, or about 6 mg/ml and about 20 mg/ml.

In another embodiment, the taxane particles and suspensions thereof may be uncoated and exclude lipids, polymers, proteins such as albumin, polyethoxylated castor oil, and/or polyethylene glycol glycerides composed of mono-, di- and triglycerides and mono- and diesters of polyethylene glycol.

In other embodiments, the taxane may comprise paclitaxel, docetaxel, cabazitaxel, or a pharmaceutically acceptable salt thereof. In one embodiment, the taxane may comprise paclitaxel or a pharmaceutically acceptable salt thereof; in this embodiment, the particles may have one or more of the following characteristics:

(a) a mean bulk density (not tapped) between about 0.050 $g/cm^3$ and about 0.12 $g/cm^3$, or between about 0.060 $g/cm^3$ and about 0.11 $g/cm^3$;

(b) a SSA of at least 12 $m^2/g$, 15 $m^2/g$, 18 $m^2/g$, 20 $m^2/g$, 25 $m^2/g$, 30 $m^2/g$, 32 $m^2/g$, 34 $m^2/g$, or 35 $m^2/g$;

(c) a SSA of between about 22 $m^2/g$ and about 40 $m^2/g$, 25 $m^2/g$ and about 40 $m^2/g$, 30 $m^2/g$ and about 40 $m^2/g$, or between about 35 $m^2/g$ and about 40 $m^2/g$; and/or (d) wherein at least 40% (w/w) of the paclitaxel is dissolved in 30 minutes or less in a solution of 50% methanol/50% water (v/v) at 37° C. and pH 7.0 in a USP II paddle apparatus operating at 75 RPM.

In another embodiment, the taxane particles may comprise docetaxel or a pharmaceutically acceptable salt thereof; in this embodiment, the particles may have one or more of the following characteristics:

(a) a mean bulk density (not tapped) between about 0.050 $g/cm^3$ and about 0.12 $g/cm^3$, or between about 0.06 $g/cm^3$ and about 0.1 $g/cm^3$;

(b) a SSA of at least 12 $m^2/g$, 15 $m^2/g$, 18 $m^2/g$, 20 $m^2/g$, 25 $m^2/g$, 30 $m^2/g$, 35 $m^2/g$, 40 $m^2/g$, or 42 $m^2/g$;

(c) a SSA of between about 20 $m^2/g$ and about 50 $m^2/g$, or between about 35 $m^2/g$ and about 46 $m^2/g$; and/or (d) wherein at least 20% (w/w) of the docetaxel is dissolved in 30 minutes or less in a solution of 15% methanol/85% water (v/v) at 37° C. and pH 7.0 in a USP II paddle apparatus operating at 75 RPM.

In another embodiment, the taxane particles may be in crystalline form. In a further embodiment, the taxane particles or suspensions thereof are aerosolized for administration, and the aerosol droplets have a mass median aerodynamic diameter (MMAD) of between about 0.5 μm to about 6 μm diameter, or between about 1 μm to about 3 μm diameter, or about 2 μm to about 3 μm diameter.

In one embodiment, the taxane may remain detectable in lung tissue of the subject for at least 4 days after the administering.

In some embodiments, the taxane particles reside at the tumor site after administration of the composition exposing the tumor to the taxane particles for a sustained amount of time sufficient to stimulate the endogenous immune system of the subject resulting in the production of tumoricidal cells and infiltration of the tumoricidal cells into the tumor at a level sufficient to treat the tumor. In some embodiments, the stimulation of the endogenous immune systems produces a cellular (cell-mediated) immune response. In other embodiments, the stimulation of the endogenous immune system produces a humoral immune response. In some embodiments, the stimulation of the endogenous immune system produces a tumor vaccine. In some embodiments, metastases are reduced or eliminated.

In one embodiment, the sustained amount of time is at least 4 weeks.

In some embodiments, the tumoricidal cells comprise T-cells, B cells, or natural killer (NK) cells, or combinations thereof.

In some embodiments, the composition is administered in two or more separate administrations.

In some embodiments, the two or more separate administrations are administered once a week for at least two weeks.

In other embodiments, the two or more separate administrations are administered twice a week for at least one week, wherein the two or more separate administrations are separated by at least one day.

In some embodiments, the treatment of the tumor is elimination of the tumor.

Disclosed in the context of the present invention are the following embodiments 1 to 25:

Embodiment 1 is a method for treating a lung disorder, including but not limited to a lung tumor or pulmonary fibrosis, comprising pulmonary administration to a subject with a lung disorder of an amount effective of a composition comprising taxane particles to treat the lung disorder, wherein the taxane particles comprise at least 95% of the taxane and have a mean particle size (number) of between 0.1 μm and 5 μm.

Embodiment 2 is the method of embodiment 1, wherein the pulmonary administration comprises nebulization, and wherein the nebulizing results in pulmonary delivery to the subject of aerosol droplets of the taxane particles or suspension thereof.

Embodiment 3 is the method of any one of embodiments 1-2, wherein the taxane particles have a mean particle size (number) of between 0.4 μm and 2 μm.

Embodiment 4 is the method of any one of embodiments 1-3, wherein the taxane particles have a mean particle size (number) of between about 0.4 μm and about 1.2 μm, or between about 0.6 μm and about 1.0 μm.

Embodiment 5 is the method of any one of embodiments 1-4, wherein the taxane particles have a specific surface area (SSA) of at least 10 m$^2$/g, or at least 12 m$^2$/g, 14 m$^2$/g, 16 m$^2$/g, 18 m$^2$/g, 20 m$^2$/g, 25 m$^2$/g, 30 m$^2$/g, 32 m$^2$/g, 34 m$^2$/g, or 35 m$^2$/g; or wherein the taxane particles have an SSA of between about 10 m$^2$/g and about 60 m$^2$/g.

Embodiment 6 is the method of any one of embodiments 1-5, wherein the taxane particles are present in a suspension, wherein the suspension comprises:
(a) the taxane particles;
(b) a pharmaceutically acceptable carrier; and
(c) a polysorbate, wherein the polysorbate is present in the suspension at a concentration of between about 0.01% v/v and about 1.5% v/v, or between about 0.01% v/v and about 1% v/v, about 0.01% v/v and about 0.5% v/v, about 0.01% v/v and about 0.4% v/v, about 0.01% v/v and about 0.25% v/v, about 0.05% v/v and about 0.5% v/v, about 0.05% v/v and about 0.25% v/v, about 0.1% v/v and about 0.5% v/v, about 0.1% v/v and about 0.25% v/v, about 0.1% v/v, about 0.16 v/v, or about 0.25% v/v.

Embodiment 7 is the method of embodiment 6, wherein the pharmaceutically acceptable carrier is saline, such as 0.9% sodium chloride solution.

Embodiment 8 is the method of embodiment 6 or 7, wherein the polysorbate is polysorbate 80.

Embodiment 9 is the method of any one of embodiments 6-8, wherein the taxane is present in the suspension at a concentration between about 1 mg/ml and about 40 mg/ml, or about 6 mg/ml and about 20 mg/ml.

Embodiment 10 is the method of any one of embodiments 1-9, wherein the particles and suspensions thereof are uncoated and exclude lipids, polymers, proteins such as albumin, polyethoxylated castor oil, and/or polyethylene glycol glycerides composed of mono-, di- and triglycerides and mono- and diesters of polyethylene glycol.

Embodiment 11 is the method of any one of embodiments 1-10, wherein the taxane comprises paclitaxel, docetaxel, cabazitaxel, or a pharmaceutically acceptable salt thereof.

Embodiment 12 is the method of embodiment 11, wherein the taxane comprises paclitaxel or a pharmaceutically acceptable salt thereof.

Embodiment 13 is the method of embodiment 12, wherein the particles have one or more of the following characteristics:
(a) a mean bulk density (not tapped) between about 0.050 g/cm$^3$ and about 0.12 g/cm$^3$, or between about 0.060 g/cm$^3$ and about 0.11 g/cm$^3$;
(b) a SSA of at least 12 m$^2$/g, 15 m$^2$/g, 18 m$^2$/g, 20 m$^2$/g, 25 m$^2$/g, 30 m$^2$/g, 32 m$^2$/g, 34 m$^2$/g, or 35 m$^2$/g;
(c) a SSA of between about 22 m$^2$/g and about 40 m$^2$/g, 25 m$^2$/g and about 40 m$^2$/g, 30 m$^2$/g and about 40 m$^2$/g, or between about 35 m$^2$/g and about 40 m$^2$/g; and/or
(d) wherein at least 40% (w/w) of the paclitaxel is dissolved in 30 minutes or less in a solution of 50% methanol/50% water (v/v) at 37° C. and pH 7.0 in a USP II paddle apparatus operating at 75 RPM.

Embodiment 14 is the method of embodiment 11, wherein the taxane comprises docetaxel or a pharmaceutically acceptable salt thereof.

Embodiment 15 is the method of embodiment 14, wherein the particles have one or more of the following characteristics:
(a) a mean bulk density (not tapped) between about 0.050 g/cm$^3$ and about 0.12 g/cm$^3$, or between about 0.06 g/cm$^3$ and about 0.1 g/cm$^3$;
(b) a SSA of at least 12 m$^2$/g, 15 m$^2$/g, 18 m$^2$/g, 20 m$^2$/g, 25 m$^2$/g, 30 m$^2$/g, 35 m$^2$/g, 40 m$^2$/g, or 42 m$^2$/g;
(c) a SSA of between about 20 m$^2$/g and about 50 m$^2$/g, or between about 35 m$^2$/g and about 46 m$^2$/g; and/or
(d) wherein at least 20% (w/w) of the docetaxel is dissolved in 30 minutes or less in a solution of 15% methanol/85% water (v/v) at 37° C. and pH 7.0 in a USP II paddle apparatus operating at 75 RPM.

Embodiment 16 is the method of any one of embodiments 1-15, wherein the taxane remains detectable in lung tissue of the subject for at least 4 days after the administering.

Embodiment 17 is the method of any one of embodiments 1-16, wherein the taxane particles are in crystalline form.

Embodiment 18 is the method of any one of embodiments 1-17, wherein the taxane particles or suspensions thereof are aerosolized for administration, and the aerosol droplets have a mass median aerodynamic diameter (MMAD) of between about 0.5 μm to about 6 μm diameter, or between about 1 μm to about 3 μm diameter, or about 2 μm to about 3 μm diameter. Embodiment 19 is the method of any one of embodiments 1-18, wherein the lung disorder comprises a lung tumor, and wherein the taxane particles reside at the tumor site after administration of the composition exposing the tumor to the taxane particles for a sustained amount of time sufficient to stimulate the endogenous immune system of the subject resulting in the production of tumoricidal cells and infiltration of the tumoricidal cells into the tumor at a level sufficient to treat the tumor.

Embodiment 20 is the method of embodiment 19, wherein the sustained amount of time is at least 4 weeks.

Embodiment 21 is the method of any one of embodiments 19-20, wherein the tumoricidal cells comprise T-cells, B cells, or natural killer (NK) cells, or combinations thereof.

Embodiment 22 is the method of any one of embodiments 1-21, wherein the composition is administered in two or more separate administrations.

Embodiment 23 is the method of embodiment 22, wherein the two or more separate administrations are administered once a week for at least two weeks.

Embodiment 24 is the method of embodiment 22, wherein the two or more separate administrations are administered twice a week for at least one week, wherein the two or more separate administrations are separated by at least one day.

Embodiment 25 is the method of any one of embodiments 1-24, wherein the lung disorder comprises a lung tumor, and wherein the treatment of the tumor is elimination of the tumor.

BRIEF DESCRIPTION OF THE FIGURES

FIG. 1 is a graph of lung tissue and plasma levels of paclitaxel over time from inhalation study.

FIG. 2 is a plot of the aerodynamic diameter of a 6.0 mg/mL paclitaxel particle formulation from inhalation study.

FIG. 3 is a plot of the aerodynamic diameter of a 20.0 mg/mL paclitaxel particle formulation from inhalation study.

FIG. 40 is a photomicrograph of Orthotopic Lung Cancer tissue slide—4009 (IH paclitaxel particle formulation 1× High) Adenocarcinoma-0, Primitive-0, Regression-4. Characteristics of a lung tumor mass that has undergone complete regression. Note stromal fibrosis. (10×).

FIG. 41 is a photomicrograph of Orthotopic Lung Cancer tissue slide—4009 (IH paclitaxel particle formulation 1× High) Adenocarcinoma-0, Primitive-0, Regression-4. Characteristics of a lung tumor mass that has undergone complete regression. Note stromal fibrosis, and lymphocytes and macrophages along the edge. (40×).

DETAILED DESCRIPTION OF THE INVENTION

Figure 4:
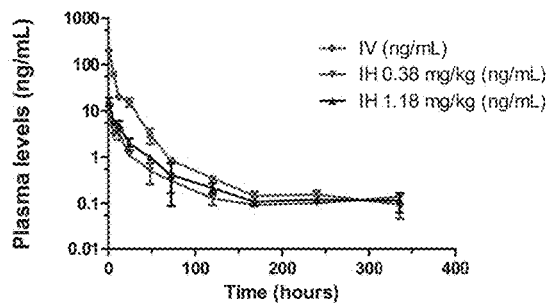
FIG. 4 is a graph of plasma levels of paclitaxel over time from inhalation study.
Figure 5:
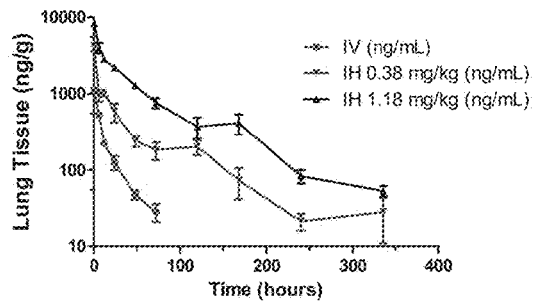
FIG. 5 is a graph of lung tissue levels of paclitaxel over time from inhalation study.
Figure 6:
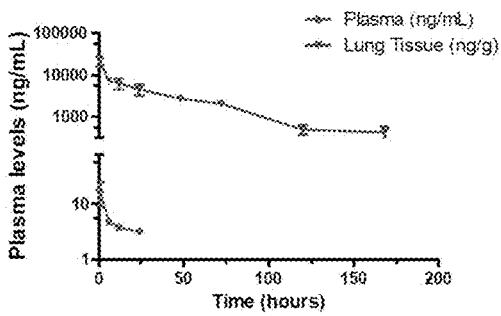
FIG. 6 is a graph of lung tissue and plasma levels of paclitaxel over time from inhalation study.

As used herein, the singular forms "a", "an" and "the" include plural referents unless the context clearly dictates otherwise. "And" as used herein is interchangeably used with "or" unless expressly stated otherwise.

As used herein, "about" means+/−five percent (5%) of the recited unit of measure.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application. The compositions and methods for their use can "comprise," "consist essentially of," or "consist of" any of the ingredients or steps disclosed throughout the specification.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the invention provides methods for treating a lung disorder, comprising pulmonary administration to a subject with a lung disorder of an amount effective of a composition comprising taxane particles to treat the lung tumor, wherein the taxane particles comprise at least 95% of the taxane and have a mean particle size (number) of between 0.1 μm and 5 μm.

The inventors have surprisingly discovered that pulmonary administration of the taxane particles according to the methods of the invention result in much longer residency times of the taxane in the lungs than was previously possible using any other taxane formulation. As shown in the examples that follow, the taxane remains detectable in lung tissue of the subject for at least 96 hours after the administering. In various further embodiments, the taxane remains detectable in lung tissue of the subject for at least 108, 120, 132, 144, 156, 168, 180, 192, 204, 216, 228, 240, 252, 264, 276, 288, 300, 312, 324, or 336 hours after the administering. Thus, the methods can be used to treat any lung disorder for which taxane particles may be an effective treatment, including but not limited to lung tumors, mesothelioma, restrictive lung diseases such as pulmonary fibrosis, and obstructive lung diseases such as chronic obstructive lung disease (COPD).

Another aspect of the invention is that the methods also allow for exposure of the taxane particles to a lung tumor after administration of the composition for a sustained amount of time sufficient to stimulate the endogenous immune system of the subject resulting in the production of tumoricidal cells and infiltration of the tumoricidal cells into the tumor at a level sufficient to treat the tumor. In some embodiments, the stimulation of the endogenous immune systems produces a cellular (cell-mediated) immune response. In other embodiments, the stimulation of the endogenous immune system produces a humoral immune response. In some embodiments, the stimulation of the endogenous immune system produces a tumor vaccine. In some embodiments, metastases are reduced or eliminated. The tumoricidal cells may comprise T-cells, B cells, or natural killer (NK) cells, or combinations thereof. In some embodiments, the sustained amount of exposure time is at least 108, 120, 132, 144, 156, 168, 180, 192, 204, 216, 228, 240, 252, 264, 276, 288, 300, 312, 324, or 336 hours. In various further embodiments, the sustained amount of exposure time is at least 3, 4, 5, 6, 7, or 8 weeks. The composition can be administered by pulmonary administration in a single administration (cycle) of a single dose, or in two or more separate administrations (2 or more cycles) of single doses. In some embodiments, the two or more separate administrations are administered at or at least 1, 2, 3, 4, 5, 6, 7, 8, 9, 10, 11, 12, or 14 days apart. In some embodiments, the two or more separate administrations are administered 2 to 12, 2-11, 2-10, 2-9, 2-8 2-7, 2-6, 2-5, 2-4, 2-3, 3-12, 3-11, 3-10, 3-9, 3-8, 3-7, 3-6, 3-5, 3-4, 4-12, 4-11, 4-10, 4-9, 4-8, 4-7, 4-6, 4-5, 5-12, 5-11, 5-10, 5-9, 5-8, 5-7, 5-6, 6-12, 6-11, 6-10, 6-9, 6-8, 6-7, 7-12, 7-11, 7-10, 7-9, 7-8, 8-12, 8-11, 8-10, 8-9, 9-12, 9-11, 9-10, 10-12, 10-11, 11-12, 2, 3, 4, 5, 6, 7, 8, 9, 10, 11, or 12 weeks apart. In some embodiments, the composition is administered in 2-5, 2-4, 2-3, 3-5, 3-4, 2, 3, 4, 5, or more separate administrations. In some embodiments, the two or more separate administrations are administered 2 to 12 weeks apart. In some embodiments, the composition is administered in two to five separate administrations. In some embodiments, the two or more separate administrations are administered once a week for at least two weeks. In other embodiments, the two or more separate administrations are administered twice a week for at least one week, wherein the two or more separate administrations are separated by at least one day. In some embodiments the treatment method results in elimination (eradication) of the tumor. In some embodiments, the composition is administered in 1, 2, 3, 4, 5, 6 or more separate administrations. In other embodiments, the composition is administered in 7 or more separate administrations.

As used herein, "taxane particles" are particles consisting essentially of the taxane (i.e.: at least 95%, 96%, 97%, 98%, 99%, or 100% taxane) that have a mean particle size (number) of between 0.1 μm and 5 μm. Taxane particles for use in the invention are uncoated, and are not embedded, contained, enclosed or encapsulated within a solid excipient. Taxane particles of the invention may, however, contain impurities and byproducts typically found during preparation of the taxane. Even so, the taxane particles comprise at least 95%, at least 96%, at least 97%, at least 98%, at least 99% or 100% taxane, meaning the taxane particles consist of or consist essentially of substantially pure taxane.

Taxanes are a class of diterpenoids containing a taxadiene core that are very poorly soluble in water. The taxane particles of the invention may be any suitable taxane, including but not limited to paclitaxel, docetaxel, cabazitaxel, taxadiene, baccatin III, taxchinin A, brevifoliol, and taxuspine D, combinations thereof, or pharmaceutically acceptable salts thereof. In one embodiment, the taxane is selected from the group consisting of paclitaxel, docetaxel, and cabazitaxel, or a pharmaceutically acceptable salt thereof.

Paclitaxel and docetaxel active pharmaceutical ingredients (APIs) are commercially available from Phyton Biotech LLC, Vancouver, Canada. The docetaxel API contains not less than 95%, or not less than 97.5% docetaxel calculated on the anhydrous, solvent-free basis. The paclitaxel API contains not less than 95%, or not less than 97% paclitaxel calculated on the anhydrous, solvent-free basis. In some embodiments, the paclitaxel API and docetaxel API are USP and/or EP grade. Paclitaxel API can be prepared from a semisynthetic chemical process or from a natural source such as plant cell fermentation or extraction.

The lung tumor is any tumor present within the lungs and may be a primary or a metastatic lung tumor. Non-limiting examples of a lung tumor include small-cell lung carcinoma (SCLC) and non-small-cell lung carcinoma (NSCLC). In one embodiment, the lung tumor is SCLC. In another embodiment, the lung tumor is a NSCLC. The subject may be any mammal subject to lung tumors, including but not limited to humans and other primates, dogs, cats, horses, cattle, pigs, sheep, goats, etc.

The "amount effective" of the taxane particle can be determined by an attending physician based on all relevant factors. The taxane particles may be the sole taxane administered, or may be administered with other therapeutics as deemed appropriate by an attending physician in light of all circumstances. In one embodiment, the methods further comprise treating the subject with the standard of care for the tumor being treated, such as intravenous chemotherapy, radiation therapy, surgical resection, etc.

As used herein, "treat", "treatment", or "treating" means accomplishing one or more of the following: (a) reducing tumor or fibrosis size; (b) reducing tumor growth rate; (c) eliminating a tumor or fibrosis; (d) reducing or limiting development and/or spreading of metastases, or eliminating metastases. In some embodiments, the treatment is eliminating a tumor or fibrosis.

In one specific embodiment of the invention, pulmonary administration comprises inhalation of a single dose of the taxane particles, such as by nasal, oral inhalation, or both. The taxane particles can be administered in two or more separate administrations (doses). In this embodiment, the taxane particles may be formulated as an aerosol (i.e.: liquid droplets of a stable dispersion or suspension of the antineoplastic particles in a gaseous medium). Taxane particles delivered by aerosol may be deposited in the airways by gravitational sedimentation, inertial impaction, and/or diffusion. Any suitable device for generating the aerosol may be used, including but not limited to pressured meter inhalers (pMDI), nebulizers, dry powder inhalers (DPI), and soft-mist inhalers.

In one specific embodiment, the methods comprise inhalation of taxane particles aerosolized via nebulization. Nebulizers generally use compressed air or ultrasonic power to create inhalable aerosol droplets of the taxane particles or suspensions thereof. In this embodiment, the nebulizing results in pulmonary delivery to the subject of aerosol droplets of the taxane particles or suspension thereof.

In another embodiment, the methods comprise inhalation of taxane particles aerosolized via a pMDI, wherein the taxane particles or suspensions thereof are suspended in a suitable propellant system (including but not limited to hydrofluoroalkanes (HFAs) containing at least one liquefied gas in a pressurized container sealed with a metering valve. Actuation of the valve results in delivery of a metered dose of an aerosol spray of the taxane particles or suspensions thereof.

In other embodiments, the taxane particles have a mean particle size (number) greater than 0.2 µm, or 0.3 µm. In another embodiment, the taxane particles have a mean particle size (number) of at least 0.4 µm. In further embodiments, the taxane particles have a mean particle size (number) of between 0.4 µm and 2 µm, or between 0.5 µm and 1.5 µm, or between 0.2 µm and 1 µm, or between 0.2 µm to less than 1 µm.

In further embodiments, the taxane particles can have a mean particle size number of between in the range of about 0.4 µm to about 5 µm, about 0.4 µm to about 3 µm, about 0.5 µm to about 1.4 µm, about 0.4 µm to about 0.8 µm, about 0.4 µm to about 0.7 µm, or about 0.5 µm to about 0.7 µm. In a further embodiment, the taxane particles have a mean particle size number of between about 0.4 µm and about 1.2 µm, or between about 0.6 µm and about 1.0 µm. In another embodiment, the taxane particles have a mean particle size number of between 0.6 µm and 0.861 µm, or between about 0.5 µm to about 0.7 µm, or between about 0.2 µm to about 1 µm, or between about 0.2 µm to less than 1 µm, or between about 0.3 µm to about 1 µm, or between about 0.3 µm to less than 1 µm, or between about 0.4 µm to about 1 µm, or between about 0.4 µm to less than 1 µm.

The particle size of the taxane particles can be determined by a particle size analyzer instrument and the measurement is expressed as the mean diameter based on a number distribution (number). A suitable particle size analyzer instrument is one which employs the analytical technique of light obscuration, also referred to as photozone or single particle optical sensing (SPOS). A suitable light obscuration particle size analyzer instrument is the ACCUSIZER, such as the ACCUSIZER 780 SIS, available from Particle Sizing Systems, Port Richey, Fla. Another suitable particle size analyzer instrument is one which employs laser diffraction, such as the Shimadzu SALD-7101.

In embodiments where the taxane particles are aerosolized for administration, the mass median aerodynamic diameter (MMAD) of the aerosol droplets of the taxane particles or suspensions thereof may be any suitable diameter for use in the invention. In one embodiment, the aerosol droplets have a MMAD of between about 0.5 µm to about 6 µm diameter. In various further embodiments, the aerosol droplets have a MMAD of between about 0.5 µm to about 5.5 µm diameter, about 0.5 µm to about 5 µm diameter, about 0.5 µm to about 4.5 µm diameter, about 0.5 µm to about 4 µm diameter, about 0.5 µm to about 3.5 µm diameter, about 0.5 µm to about 3 µm diameter, about 0.5 µm to about 2.5 µm diameter, about 0.5 µm to about 2 µm diameter, about 1 µm to about 5.5 µm diameter, about 1 µm to about 5 µm diameter, about 1 µm to about 4.5 µm diameter, about 1 µm to about 4 µm diameter, about 1 µm to about 3.5 µm diameter, about 1 µm to about 3 µm diameter, about 1 µm to about 2.5 µm diameter, about 1 µm to about 2 µm diameter, about 1.5 µm to about 5.5 µm diameter, about 1.5 µm to about 5 µm diameter, about 1.5 µm to about 4.5 µm diameter, about 1.5 µm to about 4 µm diameter, about 1.5 µm to about 3.5 µm diameter, about 1.5 µm to about 3 µm diameter, about 1.5 µm to about 2.5 µm diameter, about 1.5 µm to about 2 µm diameter, about 2 µm to about 5.5 µm diameter, about 2 µm to about 5 µm diameter, about 2 µm to about 4.5 µm diameter, about 2 µm to about 4 µm diameter, about 2 µm to about 3.5 µm diameter, about 2 µm to about 3 µm diameter, and about 2 µm to about 2.5 µm diameter. A suitable instrument for measuring the mass median aerodynamic diameter (MMAD) and geometric standard deviation (GSD) of the aerosol droplets is a seven-stage aerosol sampler such as the Mercer-Style Cascade Impactor.

In another embodiment, the taxane particles may have a specific surface area (SSA) of at least 10 $m^2/g$, or at least 12 $m^2/g$, 14 $m^2/g$, 16 $m^2/g$, 18 $m^2/g$, 20 $m^2/g$, 25 $m^2/g$, 30 $m^2/g$, 32 $m^2/g$, 34 $m^2/g$, or 35 $m^2/g$; or wherein the taxane particles have an SSA of between about 10 $m^2/g$ and about 60 $m^2/g$.

In various embodiments, the taxane particles are made by "precipitation with compressed anti-solvents" (PCA) methods as disclosed in U.S. Pat. Nos. 5,874,029, 5,833,891, 6,113,795, 7,744,923, 8,778,181, 9,233,348; US publications US 2015/0375153, US 2016/0354336, US 2016/0374953; and international patent application publications WO 2016/197091, WO 2016/197100, and WO 2016/197101; all of which are herein incorporated by reference.

In PCA particle size reduction methods using supercritical carbon dioxide, supercritical carbon dioxide (anti-solvent) and solvent, e.g. acetone or ethanol, are employed to generate uncoated taxane particles as small as 0.1 to 5 microns within a well-characterized particle-size distribution. The carbon dioxide and solvent are removed during processing (up to 0.5% residual solvent may remain), leaving taxane particles as a powder. Stability studies show that the paclitaxel particle powder is stable in a vial dose form when stored at room temperature for up to 59 months and under accelerated conditions (40° C./75% relative humidity) for up to six months.

Taxane particles produced by various supercritical carbon dioxide particle size reduction methods can have unique physical characteristics as compared to taxane particles produced by conventional particle size reduction methods using physical impacting or grinding, e.g., wet or dry milling, micronizing, disintegrating, comminuting, microfluidizing, or pulverizing. As disclosed in US publication 2016/0374953, herein incorporated by reference, such unique characteristics include a bulk density (the mass of the totality of particles in the composition divided by the total volume they occupy when poured into a graduated cylinder, without tapping the graduated cylinder, with the total volume including particle volume, inter-particle void volume, and internal pore volume.) between 0.05 $g/cm^3$ and 0.15 $g/cm^3$ and a specific surface area (SSA) of at least 18 $m^2/g$ of taxane (e.g., paclitaxel and docetaxel) particles, which are produced by the supercritical carbon dioxide particle size reduction methods described in US publication 2016/0374953 and as described below. This bulk density range is generally lower than the bulk density of taxane particles produced by conventional means, and the SSA is generally higher than the SSA of taxane particles produced by conventional means. These unique characteristics result in significant increases in dissolution rates in water/methanol media as compared to taxanes produced by conventional means. As used herein, the "specific surface area" (SSA) is the total surface area of the taxane particle per unit of taxane mass as measured by the Brunauer-Emmett-Teller ("BET") isotherm by the following method: a known mass between 200 and 300 mg of the analyte is added to a 30 mL sample tube. The loaded tube is then mounted to a Porous Materials Inc. SORPTOMETER®, model BET-202A. The automated test is then carried out using the BETWIN® software package and the surface area of each sample is subsequently calculated. As will be understood by those of skill in the art, the "taxane particles" can include both agglomerated taxane particles and non-agglomerated taxane particles; since the SSA is determined on a per gram basis it takes into account both agglomerated and non-agglomerated taxane particles in the composition. The BET specific surface area test procedure is a compendial method included in both the United States Pharmaceopeia and the European Pharmaceopeia. The bulk density measurement can be conducted by pouring the taxane particles into a graduated cylinder without tapping at room temperature, measuring the mass and volume, and calculating the bulk density.

As disclosed in US publication 2016/0374953, studies showed a SSA of 15.0 $m^2/g$ and a bulk density of 0.31 $g/cm^3$ for paclitaxel particles produced by milling paclitaxel in a Deco-PBM-V-0.41 ball mill suing a 5 mm ball size, at 600 RPM for 60 minutes at room temperature. Also disclosed in US publication 2016/0374953, one lot of paclitaxel particles had a SSA of 37.7 $m^2/g$ and a bulk density of 0.085 $g/cm^3$ when produced by a supercritical carbon dioxide method using the following method: a solution of 65 mg/mL of paclitaxel was prepared in acetone. A BETE MicroWhirl® fog nozzle (BETE Fog Nozzle, Inc.) and a sonic probe (Qsonica, model number Q700) were positioned in the crystallization chamber approximately 8 mm apart. A stainless steel mesh filter with approximately 100 nm holes was attached to the crystallization chamber to collect the precipitated paclitaxel particles. The supercritical carbon dioxide was placed in the crystallization chamber of the manufacturing equipment and brought to approximately 1200 psi at about 38° C. and a flow rate of 24 kg/hour. The sonic probe was adjusted to 60% of total output power at a frequency of 20 kHz. The acetone solution containing the paclitaxel was pumped through the nozzle at a flow rate of 4.5 mL/minute for approximately 36 hours. Additional lots of paclitaxel particles produced by the supercritical carbon dioxide method described above had SSA values of: 22.27 $m^2/g$, 23.90 $m^2/g$, 26.19 $m^2/g$, 30.02 $m^2/g$, 31.16 $m^2/g$, 31.70 $m^2/g$, 32.59 $m^2/g$, 33.82 $m^2/g$, 35.90 $m^2/g$, 38.22 $m^2/g$, and 38.52 $m^2/g$.

As disclosed in US publication 2016/0374953, studies showed a SSA of 15.2 $m^2/g$ and a bulk density of 0.44 $g/cm^3$ for docetaxel particles produced by milling docetaxel in a Deco-PBM-V-0.41 ball mill suing a 5 mm ball size, at 600 RPM for 60 minutes at room temperature. Also disclosed in US publication 2016/0374953, docetaxel particles had a SSA of 44.2 $m^2/g$ and a bulk density of 0.079 $g/cm^3$ when produced by a supercritical carbon dioxide method using the following method: A solution of 79.32 mg/mL of docetaxel was prepared in ethanol. The nozzle and a sonic probe were positioned in the pressurizable chamber approximately 9 mm apart. A stainless steel mesh filter with approximately 100 nm holes was attached to the pressurizable chamber to collect the precipitated docetaxel particles. The supercritical carbon dioxide was placed in the pressurizable chamber of the manufacturing equipment and brought to approximately 1200 psi at about 38° C. and a flow rate of 68 slpm. The sonic probe was adjusted to 60% of total output power at a frequency of 20 kHz. The ethanol solution containing the docetaxel was pumped through the nozzle at a flow rate of 2 mL/minute for approximately 95 minutes). The precipitated docetaxel agglomerates and particles were then collected from the supercritical carbon dioxide as the mixture is pumped through the stainless steel mesh filter. The filter containing the particles of docetaxel was opened and the resulting product was collected from the filter.

As disclosed in US publication 2016/0374953, dissolution studies showed an increased dissolution rate in methanol/water media of paclitaxel and docetaxel particles made by the supercritical carbon dioxide methods described in US publication 2016/0374953 as compared to paclitaxel and docetaxel particles made by milling paclitaxel and docetaxel using a Deco-PBM-V-0.41 ball mill suing a 5 mm ball size, at 600 RPM for 60 minutes at room temperature. The procedures used to determine the dissolution rates are as follows. For paclitaxel, approximately 50 mg of material were coated on approximately 1.5 grams of 1 mm glass beads by tumbling the material and beads in a vial for approximately 1 hour. Beads were transferred to a stainless steel mesh container and placed in the dissolution bath containing methanol/water 50/50 (v/v) media at 37° C., pH 7, and a USP Apparatus II (Paddle), operating at 75 rpm. At 10, 20, 30, 60, and 90 minutes, a 5 mL aliquot was removed, filtered through a 0.22 μm filter and analyzed on a UV/VIS spectrophotometer at 227 nm. Absorbance values of the samples were compared to those of standard solutions prepared in dissolution media to determine the amount of material dissolved. For docetaxel, approximately 50 mg of material was placed directly in the dissolution bath containing methanol/water 15/85 (v/v) media at 37° C., pH 7, and a USP Apparatus II (Paddle), operating at 75 rpm. At 5, 15, 30, 60, 120 and 225 minutes, a 5 mL aliquot was removed, filtered through a 0.22 μm filter, and analyzed on a UV/VIS spectrophotometer at 232 nm. Absorbance values of the samples were compared to those of standard solutions prepared in dissolution media to determine the amount of material dissolved. For paclitaxel, the dissolution rate was 47% dissolved in 30 minutes for the particles made by the supercritical carbon dioxide method versus 32% dissolved in 30 minutes for the particles made by milling. For docetaxel, the dissolution rate was 27% dissolved in 30 minutes for the particles made by the supercritical carbon dioxide method versus 9% dissolved in 30 minutes for the particles made by milling.

In some embodiments, the taxane particles have a SSA of at least 10, at least 12, at least 14, at least 16, at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 $m^2/g$. In one embodiment, the antineoplastic particles have an SSA of between about 10 $m^2/g$ and about 50 $m^2/g$. In some embodiments, the antineoplastic particles have a bulk density (not tapped) between about 0.050 $g/cm^3$ and about 0.20 $g/cm^3$.

In further embodiments, the antineoplastic particles have a SSA of:
(a) between 16 $m^2/g$ and 31 $m^2/g$ or between 32 $m^2/g$ and 40 $m^2/g$;
(b) between 16 $m^2/g$ and 30 $m^2/g$ or between 32 $m^2/g$ and 40 $m^2/g$;
(c) between 16 $m^2/g$ and 29 $m^2/g$ or between 32 $m^2/g$ and 40 $m^2/g$;
(d) between 17 $m^2/g$ and 31 $m^2/g$ or between 32 $m^2/g$ and 40 $m^2/g$;
(e) between 17 $m^2/g$ and 30 $m^2/g$ or between 32 $m^2/g$ and 40 $m^2/g$;
(f) between 17 $m^2/g$ and 29 $m^2/g$, or between 32 $m^2/g$ and 40 $m^2/g$;
(g) between 16 $m^2/g$ and 31 $m^2/g$ or between 33 $m^2/g$ and 40 $m^2/g$;

(h) between 16 m²/g and 30 m²/g or between 33 m²/g and 40 m²/g;
(i) between 16 m²/g and 29 m²/g or between 33 m²/g and 40 m²/g;
(j) between 17 m²/g and 31 m²/g or between 33 m²/g and 40 m²/g;
(k) between 17 m²/g and 30 m²/g or between 33 m²/g and 40 m²/g;
(l) between 17 m²/g and 29 m²/g, or between 33 m²/g and 40 m²/g;
(m) between 16 m²/g and 31 m²/g, or≥32 m²/g;
(h) between 17 m²/g and 31 m²/g, or≥32 m²/g;
(i) between 16 m²/g and 30 m²/g, or≥32 m²/g;
(j) between 17 m²/g and 30 m²/g, or≥32 m²/g;
(k) between 16 m²/g and 29 m²/g, or≥32 m²/g;
(l) between 17 m²/g and 29 m²/g, or≥32 m²/g;
(m) between 16 m²/g and 31 m²/g, or≥33 m²/g;
(n) between 17 m²/g and 31 m²/g, or≥33 m²/g;
(o) between 16 m²/g and 30 m²/g, or≥33 m²/g;
(p) between 17 m²/g and 30 m²/g, or≥33 m²/g;
(q) between 16 m²/g and 29 m²/g, or≥33 m²/g; or
(r) between 17 m²/g and 29 m²/g, or≥33 m²/g.

In some embodiments, the taxane particles are paclitaxel particles and have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 m²/g. In other embodiments, the paclitaxel particles have an SSA of 18 m²/g to 50 m²/g, or 20 m²/g to 50 m²/g, or 22 m²/g to 50 m²/g, or 25 m²/g to 50 m²/g, or 26 m²/g to 50 m²/g, or 30 m²/g to 50 m²/g, or 35 m²/g to 50 m²/g, or 18 m²/g to 45 m²/g, or 20 m²/g to 45 m²/g, or 22 m²/g to 45 m²/g, or 25 m²/g to 45 m²/g, or 26 m²/g to 45 m²/g or 30 m²/g to 45 m²/g, or 35 m²/g to 45 m²/g, or 18 m²/g to 40 m²/g, or 20 m²/g to 40 m²/g, or 22 m²/g to 40 m²/g, or 25 m²/g to 40 m²/g, or 26 m²/g to 40 m²/g, or 30 m²/g to 40 m²/g, or 35 m²/g to 40 m²/g.

In some embodiments, the paclitaxel particles have a bulk density (not-tapped) of 0.05 g/cm³ to 0.15 g/cm³, or 0.05 g/cm³ to 0.20 g/cm³.

In some embodiments, the paclitaxel particles have a dissolution rate of at least 40% w/w dissolved in 30 minutes or less in a solution of 50% methanol/50% water (v/v) in a USP II paddle apparatus operating at 75 RPM, at 37° C., and at a pH of 7.

In another embodiment, the paclitaxel particles have one or more of the following characteristics:
(a) a mean bulk density (not tapped) between about 0.050 g/cm³ and about 0.12 g/cm³, or between about 0.060 g/cm³ and about 0.11 g/cm³;
(b) a SSA of at least 12 m²/g, 15 m²/g, 18 m²/g, 20 m²/g, 25 m²/g, 30 m²/g, 32 m²/g, 34 m²/g, or 35 m²/g;
(c) a SSA of between about 22 m²/g and about 40 m²/g, 25 m²/g and about 40 m²/g, 30 m²/g and about 40 m²/g, or between about 35 m²/g and about 40 m²/g; and/or
(d) wherein at least 40% (w/w) of the paclitaxel is dissolved in 30 minutes or less in a solution of 50% methanol/50% water (v/v) at 37° C. and pH 7.0 in a USP II paddle apparatus operating at 75 RPM.

In one embodiment, the paclitaxel particles have a mean bulk density (not tapped) of between about between about 0.050 g/cm³ and about 0.12 g/cm³ and a SSA of at least 30 m²/g. In another embodiment, the paclitaxel particles have a mean bulk density (not tapped) of between about about 0.050 g/cm³ and about 0.12 g/cm³ and a SSA of at least 35 m²/g. In one embodiment the paclitaxel particles have a mean bulk density (not tapped) of between about between about 0.050 g/cm³ and about 0.12 g/cm³ and a SSA of between about 30 m²/g and about 40 m²/g. In another embodiment, the paclitaxel particles have a mean bulk density (not tapped) of between about 0.060 g/cm³ and about 0.11 g/cm³ and a SSA of between about 30 m²/g and about 40 m²/g. In another embodiment, the paclitaxel particles have a mean bulk density (not tapped) of between about 0.060 g/cm³ and about 0.11 g/cm³ and a SSA of at least 30 m²/g. In a further embodiment, the paclitaxel particles have a mean bulk density (not tapped) of between about 0.060 g/cm³ and about 0.11 g/cm³ and a SSA of at least 35 m²/g.

In another embodiment, at least 40% (w/w) of the paclitaxel in the paclitaxel particles of the composition is dissolved in 30 minutes or less in a solution of 50% methanol/50% water (v/v) in a USP II paddle apparatus operating at 75 RPM. pH 7 was used, and the solubility of the taxanes are not effected by pH. In another embodiment, the dissolution studies are carried out at 37° C.

In some embodiments, the taxane particles are docetaxel particles and have an SSA of at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, or at least 42 m²/g. In other embodiments, the docetaxel particles have an SSA of 18 m²/g to 60 m²/g, or 22 m²/g to 60 m²/g, or 25 m²/g to 60 m²/g, or 30 m²/g to 60 m²/g, or 40 m²/g to 60 m²/g, or 18 m²/g to 50 m²/g, or 22 m²/g to 50 m²/g, or 25 m²/g to 50 m²/g, or 26 m²/g to 50 m²/g, or 30 m²/g to 50 m²/g, or 35 m²/g to 50 m²/g, or 40 m²/g to 50 m²/g.

In some embodiments, the docetaxel particles have a bulk density (not-tapped) of 0.05 g/cm³ to 0.15 g/cm³.

In some embodiments, the docetaxel particles have a dissolution rate of at least 20% w/w dissolved in 30 minutes or less in a solution of 15% methanol/85% water (v/v) in a USP II paddle apparatus operating at 75 RPM, at 37° C., and at a pH of 7.

In another embodiment, the docetaxel particles have one or more of the following characteristics:
(a) a mean bulk density (not tapped) between about 0.050 g/cm³ and about 0.12 g/cm³, or between about 0.06 g/cm³ and about 0.1 g/cm³;
(b) a SSA of at least 12 m²/g, 15 m²/g, 18 m²/g, 20 m²/g, 25 m²/g, 30 m²/g, 35 m²/g, 40 m²/g, or 42 m²/g;
(c) a SSA of between about 20 m²/g and about 50 m²/g, or between about 35 m²/g and about 46 m²/g; and/or
(d) wherein at least 20% (w/w) of the docetaxel is dissolved in 30 minutes or less in a solution of 15% methanol/85% water (v/v) at 37° C. and pH 7.0 in a USP II paddle apparatus operating at 75 RPM.

In one embodiment, the docetaxel particles have a mean bulk density (not tapped) between about 0.050 g/cm³ and about 0.12 g/cm³ and a SSA of at least 30 m²/g. In another embodiment, the docetaxel particles have a mean bulk density (not tapped) between about 0.050 g/cm³ and about 0.12 g/cm³ and a SSA of at least 35 m²/g. In a further embodiment, the docetaxel particles have a mean bulk density (not tapped) between about 0.050 g/cm³ and about 0.12 g/cm³ and a SSA of at least 40 m²/g. In one embodiment, the docetaxel particles have a mean bulk density (not tapped) between about 0.050 g/cm³ and about 0.12 g/cm³ and a SSA of between about 20 m²/g and about 50 m²/g. In another embodiment, mean bulk density (not tapped) of the docetaxel particles is between about 0.06 g/cm³ and about 0.1 g/cm³ and the SSA is between about 30 m²/g and about 50 m²/g. In another embodiment, mean bulk density (not tapped) of the docetaxel particles is between about 0.06 g/cm$^3$ and about 0.1 g/cm$^3$ and the SSA is between about 35 m$^2$/g and about 50 m$^2$/g. In another embodiment, mean bulk density (not tapped) of the docetaxel particles is between about 0.06 g/cm$^3$ and about 0.1 g/cm$^3$ and the SSA is between about 35 m$^2$/g and about 45 m$^2$/g.

In another embodiment, at least 20% (w/w) of the docetaxel is dissolved in 30 minutes or less in a solution of 15% methanol/85% water (v/v) in a USP II paddle apparatus operating at 75 RPM. A neutral pH was used where the solubility of the taxanes are not effected by pH. In another embodiment, the dissolution studies are carried out at 37° C.

In any of these various embodiments, the taxane particles may include at least 4.16×10$^{-13}$ gram taxane, or a pharmaceutically acceptable salt thereof per taxane particle. In some embodiments, the taxane particles are non-agglomerated individual particles and are not clusters of multiple taxane particles.

In various embodiments of the present invention, the taxane particles are uncoated (neat) individual particles; the taxane particles are not bound to or conjugated to any substance; no substances are absorbed or adsorbed onto the surface of the taxane particles; the taxane particles are not encapsulated in any substance; the taxane particles are not coated with any substance; the taxane particles are not microemulsions, nanoemulsions, microspheres, or liposomes of a taxane; and/or the taxane particles are not bound to, attached to, encapsulated in, or coated with a monomer, a polymer (or biocompatible polymer), a protein, a surfactant, or albumin. In some embodiments, a monomer, a polymer (or biocompatible polymer), a copolymer, a protein, a surfactant, or albumin is not absorbed or adsorbed onto the surface of the taxane particles. In some embodiments, the compositions are free of/do not include or contain a polymer/copolymer or biocompatible polymer/copolymer. In some embodiments, the compositions are free of/do not include or contain a protein. In some aspects of the invention, the compositions are free of/do not include or contain albumin. In some aspects of the invention, the compositions are free of/do not include or contain hyaluronic acid. In some aspects of the invention, the compositions are free of/do not include or contain a conjugate of hyaluronic acid and a taxane. In some aspects of the invention, the compositions are free of/do not include or contain a conjugate of hyaluronic acid and paclitaxel. In some aspects of the invention, the compositions are free of/do not include or contain poloxamers, polyanions, polycations, modified polyanions, modified polycations, chitosan, chitosan derivatives, metal ions, nanovectors, poly-gamma-glutamic acid (PGA), polyacrylic acid (PAA), alginic acid (ALG), Vitamin E-TPGS, dimethyl isosorbide (DMI), methoxy PEG 350, citric acid, anti-VEGF antibody, ethylcellulose, polystyrene, polyanhydrides, polyhydroxy acids, polyphosphazenes, polyorthoesters, polyesters, polyamides, polysaccharides, polyproteins, styrene-isobutylene-styrene (SIBS), a polyanhydride copolymer, polycaprolactone, polyethylene glycol (PEG), Poly (bis(P-carboxyphenoxy)propane-sebacic acid, poly(d,l-lactic acid) (PLA), poly(d.l-lactic acid-co-glycolic acid) (PLAGA), and/or poly(D, L lactic-co-glycolic acid (PLGA). In some embodiments, the taxane particles are in crystalline form. In other embodiments, the taxane particles are in amorphous form, or a combination of both crystalline and amorphous form.

In one embodiment, the taxane particles for administration comprises a dosage form of taxane in suspension (i.e.: with a pharmaceutically acceptable carrier, and or in an aerosol formulation) of between about 0.1 mg/ml and about 100 mg/ml taxane. In various further embodiments, the dosage form may be between about 0.5 mg/ml and about 100 mg/ml, about 1 mg/ml and about 100 mg/ml, about 2 mg/ml and about 100 mg/ml, about 5 mg/ml and about 100 mg/ml, about 10 mg/ml and about 100 mg/ml, about 25 mg/ml and about 100 mg/ml, about 0.1 mg/ml and about 75 mg/ml, about 0.5 mg/ml and about 75 mg/ml, about 1 mg/ml and about 75 mg/ml, about 2 mg/ml and about 75 mg/ml, about 5 mg/ml and about 75 mg/ml, about 10 mg/ml and about 75 mg/ml, about 25 mg/ml and about 75 mg/m, about 0.1 mg/ml and about 50 mg/ml, about 0.5 mg/ml and about 50 mg/ml, about 1 mg/ml and about 50 mg/ml, about 2 mg/ml and about 50 mg/ml, about 5 mg/ml and about 50 mg/ml, about 10 mg/ml and about 50 mg/ml, about 25 mg/ml and about 50 mg/m, about 0.1 mg/ml and about 25 mg/ml, about 0.5 mg/ml and about 25 mg/ml, about 1 mg/ml and about 40 mg/ml, about 1 mg/ml and about 25 mg/ml, about 2 mg/ml and about 25 mg/ml, about 5 mg/ml and about 25 mg/ml, about 10 mg/ml and about 25 mg/ml, about 0.1 mg/ml and about 15 mg/ml, about 0.5 mg/ml and about 15 mg/ml, about 1 mg/ml and about 15 mg/ml, about 2 mg/ml and about 15 mg/ml, about 5 mg/ml and about 15 mg/ml, about 10 mg/ml and about 15 mg/ml, about 0.1 mg/ml and about 10 mg/ml, about 0.5 mg/ml and about 10 mg/ml, about 1 mg/ml and about 10 mg/ml, about 2 mg/ml and about 10 mg/ml, about 5 mg/ml and about 10 mg/ml, about 0.1 mg/ml and about 5 mg/ml, about 0.5 mg/ml and about 5 mg/ml, about 1 mg/ml and about 5 mg/ml, about 2 mg/ml and about 5 mg/ml, about 0.1 mg/ml and about 2 mg/ml, about 0.5 mg/ml and about 2 mg/ml, about 1 mg/ml and about 2 mg/ml, about 0.1 mg/ml and about 1 mg/ml, about 0.5 mg/ml and about 1 mg/ml, about 0.1 mg/ml and about 0.5 mg/ml, about 0.1 mg/ml and about 15 mg/ml, about 0.5 mg/ml and about 15 mg/ml, about 1 mg/ml and about 15 mg/ml, about 2 mg/ml and about 15 mg/ml, about 5 mg/ml and about 15 mg/ml, about 3 mg/ml and about 8 mg/ml, or about 4 mg/ml and about 6 mg/ml taxane, or at least about 0.1, 0.5, 1, 10, 20, 25, 50, 75, or 100 mg/ml taxane.

In one embodiment, the taxane particles are present in a liquid carrier prior to aerosolization. Any suitable liquid carrier may be used, such as an aqueous liquid carrier. Any suitable aqueous liquid carrier can be used, including but not limited to 0.9% saline solution (normal saline) such as 0.9% Sodium Chloride for Injection USP. In another embodiment, the taxane particles are present in a suspension prior to aerosolization. In some embodiments, the suspension includes an aqueous carrier. The carrier can comprise buffering agent, osmotic salt and/or surfactant in water, and other agents for adjustment of pH, isotonicity and viscosity. In one embodiment employing an aqueous carrier, the concentration of surfactant is less than 1% on a w/w or w/v basis; in other embodiments, less than 0.5%, less than 0.25%, or about 0.1%. In other embodiments, the aqueous carrier can exclude the surfactants GELUCIRE® (polyethylene glycol glycerides composed of mono-, di- and triglycerides and mono- and diesters of polyethylene glycol) and/or CREMOPHOR® (polyethoxylated castor oil). In some embodiments, the composition or suspension excludes polymers, proteins (such as albumin), polyethoxylated castor oil, and/or polyethylene glycol glycerides composed of mono-, di- and triglycerides and mono- and diesters of polyethylene glycol.

In some embodiments, the suspension can comprise water and optionally one or more excipients selected from the group consisting of buffer, tonicity adjusting agent, preservative, demulcent, viscosity modifier, osmotic agent, surfactant, antioxidant, alkalinizing agent, acidifying agent, antifoaming agent, and colorant. For example, the suspension can comprise taxane particles, water, buffer and salt. It optionally further comprises a surfactant. In some embodiments, the suspension consists essentially of or consists of water, paclitaxel particles suspended in the water and buffer. The suspension can further contain an osmotic salt.

The suspension can comprise one or more surfactants. Suitable surfactants include by way of example and without limitation polysorbates, lauryl sulfates, acetylated monoglycerides, diacetylated monoglycerides, and poloxamers. Polysorbates are polyoxyethylene sorbitan fatty acid esters which are a series of partial fatty acid esters of sorbitol and its anhydrides copolymerized with approximately 20, 5, or 4 moles of ethylene oxide for each mole of sorbitol and its anhydrides. Non-limiting examples of polysorbates are polysorbate 20, polysorbate 21, polysorbate 40, polysorbate 60, polysorbate 61, polysorbate 65, polysorbate 80, polysorbate 81, polysorbate 85, and polysorbate 120. Polysorbates containing approximately 20 moles of ethylene oxide are hydrophilic nonionic surfactants. Examples of polysorbates containing approximately 20 moles of ethylene oxide include polysorbate 20, polysorbate 40, polysorbate 60, polysorbate 65, polysorbate 80, polysorbate 85, and polysorbate 120. Polysorbates are available commercially from Croda under the tradename TWEEN™. The number designation of the polysorbate corresponds to the number designation of the TWEEN, e.g., polysorbate 20 is TWEEN 20, polysorbate 40 is TWEEN 40, polysorbate 60 is TWEEN 60, polysorbate 80 is TWEEN 80, etc. USP/NF grades of polysorbate include polysorbate 20 NF, polysorbate 40 NF, polysorbate 60 NF, and polysorbate 80 NF. Polysorbates are also available in PhEur grades (European Pharmacopoeia), BP grades, and JP grades. The term "polysorbate" is a non-proprietary name. The chemical name of polysorbate 20 is polyoxyethylene 20 sorbitan monolaurate. The chemical name of polysorbate 40 is polyoxyethylene 20 sorbitan monopalmitate. The chemical name of polysorbate 60 is polyoxyethylene 20 sorbitan monostearate. The chemical name of polysorbate 80 is polyoxyethylene 20 sorbitan monooleate. In some embodiments, the suspension can comprise mixtures of polysorbates. In some embodiments, the suspension comprises polysorbate 20, polysorbate 40, polysorbate 60, polysorbate 65, polysorbate 80, polysorbate 85, and/or polysorbate 120. In other embodiments, the suspension comprises polysorbate 20, polysorbate 40, polysorbate 60, and/or polysorbate 80. In one embodiment, the suspension comprises polysorbate 80.

The suspension can comprise one or more tonicity adjusting agents. Suitable tonicity adjusting agents include by way of example and without limitation, one or more inorganic salts, electrolytes, sodium chloride, potassium chloride, sodium phosphate, potassium phosphate, sodium, potassium sulfates, sodium and potassium bicarbonates and alkaline earth metal salts, such as alkaline earth metal inorganic salts, e.g., calcium salts, and magnesium salts, mannitol, dextrose, glycerin, propylene glycol, and mixtures thereof.

The suspension can comprise one or more buffering agents. Suitable buffering agents include by way of example and without limitation, dibasic sodium phosphate, monobasic sodium phosphate, citric acid, sodium citrate hydrochloric acid, sodium hydroxide, tris(hydroxymethyl)aminomethane, bis(2-hydroxyethyl)iminotris-(hydroxymethyl) methane, and sodium hydrogen carbonate and others known to those of ordinary skill in the art. Buffers are commonly used to adjust the pH to a desirable range for intraperitoneal use. Usually a pH of around 5 to 9, 5 to 8, 6 to 7.4, 6.5 to 7.5, or 6.9 to 7.4 is desired.

The suspension can comprise one or more demulcents. A demulcent is an agent that forms a soothing film over a mucous membrane, such as the membranes lining the peritoneum and organs therein. A demulcent may relieve minor pain and inflammation and is sometimes referred to as a mucoprotective agent. Suitable demulcents include cellulose derivatives ranging from about 0.2 to about 2.5% such as carboxymethylcellulose sodium, hydroxyethyl cellulose, hydroxypropyl methylcellulose, and methylcellulose; gelatin at about 0.01%; polyols in about 0.05 to about 1%, also including about 0.05 to about 1%, such as glycerin, polyethylene glycol 300, polyethylene glycol 400, and propylene glycol; polyvinyl alcohol from about 0.1 to about 4%; povidone from about 0.1 to about 2%; and dextran 70 from about 0.1% when used with another polymeric demulcent described herein.

The suspension can comprise one or more alkalinizing agents to adjust the pH. As used herein, the term "alkalizing agent" is intended to mean a compound used to provide an alkaline medium. Such compounds include, by way of example and without limitation, ammonia solution, ammonium carbonate, potassium hydroxide, sodium carbonate, sodium bicarbonate, and sodium hydroxide and others known to those of ordinary skill in the art The suspension can comprise one or more acidifying agents to adjust the pH. As used herein, the term "acidifying agent" is intended to mean a compound used to provide an acidic medium. Such compounds include, by way of example and without limitation, acetic acid, amino acid, citric acid, nitric acid, fumaric acid and other alpha hydroxy acids, hydrochloric acid, ascorbic acid, and nitric acid and others known to those of ordinary skill in the art.

The suspension can comprise one or more antifoaming agents. As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE, octoxynol and others known to those of ordinary skill in the art.

The suspension can comprise one or more viscosity modifiers that increase or decrease the viscosity of the suspension. Suitable viscosity modifiers include methylcellulose, hydroxypropyl methycellulose, mannitol and polyvinylpyrrolidone.

In some embodiments, the taxane particle is present in a suspension further comprising a polysorbate. In one specific embodiment, the taxane particle is present in a suspension further comprising a polysorbate, wherein the polysorbate is polysorbate 80. In other embodiments, the polysorbate or polysorbate 80 is present in the suspension at a concentration of between about 0.01% v/v and about 1.5% v/v. The inventors have surprisingly discovered that the recited very small amounts of polysorbate 80 reduce the surface tension at the interface of the taxane particles and the aqueous carrier in the suspension (such as saline). In some embodiments, the particles may be coated with the polysorbate or polysorbate 80, in other embodiments the particles are not coated with the polysorbate or polysorbate 80. In various other embodiments, the polysorbate or polysorbate 80 is present in the suspension at a concentration of between about 0.01% v/v and about 1% v/v, about 0.01% v/v and about 0.5% v/v, about 0.01% v/v and about 0.4% v/v, about 0.01% v/v and about 0.25% v/v, about 0.05% v/v and about 0.5% v/v, about 0.05% v/v and about 0.25% v/v, about 0.1% v/v and about 0.5% v/v, about 0.1% v/v and about 0.25% v/v, about 0.1% v/v, about 0.16 v/v, or about 0.25% v/v. In further embodiments, the taxane, such as paclitaxel, is present in the suspension at a concentration between about 1 mg/ml and about 40 mg/ml, or about 6 mg/ml and about 20 mg/ml. In various further embodiments, the taxane is present in the suspension at a concentration between about 6 mg/ml and about 15 mg/ml, between about 6 mg/ml and about 10 mg/ml, about 10 mg/ml and about 20 mg/ml, about 10 mg/ml and about 15 mg/ml, about 6 mg/ml, about 10 mg/ml, or about 15 mg/ml. In various further embodiments, the aqueous carrier in the composition may be saline, such as about 0.9% sodium chloride.

Example 1 paclitaxel particles (i.e.: paclitaxel particles as disclosed herein, approximately 98% paclitaxel with a mean particle size (number) of 0.83 microns, a SSA of 27.9 $m^2/g$, and a bulk density (not tapped) of 0.0805 $g/cm^3$ used in examples 1, 2, 3, and 4) in Suspension—Safety and Efficacy Development Program—Pilot Pharmacokinetic Study in Sprague Dawley Rats Study Number: FY17-008A Executive Summary The objective of this pilot study was to define sampling time points for a complete pharmacokinetic (PK) study with paclitaxel particle suspension formulation. Due to the potential for the paclitaxel particle formulation to result in increased retention in the lungs, nine time points from 0.5 to 168 hours were evaluated to determine the appropriate sampling strategy for a complete pharmacokinetic study.

Sixteen (16) Sprague Dawley rats were exposed to paclitaxel particle formulation (target dose of 0.37 mg/kg) by nose only inhalation on a single occasion. Two animals (n=2) were euthanatized at their designated time point of 0.5, 6, 12, 24, 48, 72, 120 and 168 hours post exposure. Samples of blood (plasma) and lung tissue were collected.

On the day of exposure, the paclitaxel particle formulation (6 mg/mL) was prepared as per instructions provided by the sponsor Total aerosol exposure time was 63 minutes for all animals. Aerosol concentration was monitored throughout the 63 minute paclitaxel particle formulation aerosol exposure by measuring the amount of formulation accumulated on 47-mm GF/A filters positioned at the breathing zone in a nose-only exposure chamber. The aerosol particle size (droplet size) was measured using Mercer style cascade impactor from animal breathing zone on the exposure chamber.

paclitaxel particle suspension formulation was aerosolized using two Hospitak compressed air jet nebulizers (average Paclitaxel aerosol concentration: target 82.65 μg/L). The overall average aerosol concentration as measured from the GF/A filters was 0.24 mg/L, and the average Paclitaxel aerosol concentration was 73.5 μg/mL. The particle size distribution was measured to be 2.0 μm MMAD with a GSD of 2.2. The measured average Paclitaxel aerosol concentration of 73.5 μg/L was ~11% lower from target average Paclitaxel aerosol concentration of 82.65 μg/L (within the accuracy/recovery performance criteria of the analytical assay of ±15%). Oxygen and temperature were monitored throughout the paclitaxel particles formulation aerosols exposure. The recorded oxygen and temperature ranges were 19.7%-20.9% and 20.4° C.-20.8° C., respectively.

Paclitaxel deposited dose to the lung was calculated based on the Paclitaxel average aerosol concentration of 73.5 μg/L, average rodent body weight of 326 g, assumed deposition fraction of 10% and exposure duration of 63 minutes. The average achieved rodent deposited dose was determined to be 0.33 mg/kg. The average achieved deposited dose was ~11% lower when compared to target deposited dose of 0.37 mg/kg, but was within the expected variability (±15% from target) for nebulized exposures.

All animals survived to their designated necropsy timepoint. At necropsy, several animals had minimal, red discolorations on the lungs. No other abnormal gross observations were noted at necropsy. From body and lung weights obtained at necropsy, average terminal bodyweight among animals at all timepoints (standard deviation) was 346.26 g (24.01); and average lung weight (standard deviation) was 1.60 g (0.13).

Systemic blood (in the form of plasma from $K_2EDTA$) was assayed via the liquid chromatography-mass spectrometry (LCMS) assay and lung tissue was assayed as briefly described in section 4.6 (Bioanalytical Analysis) to quantify the amount of paclitaxel as a function of time. The lung tissue analysis showed lung exposure with detectable amounts of Paclitaxel out to 168 hours. The systemic blood showed no detectable Paclitaxel (under 1 ng/mL) after 24 hours. Based on these data the following sampling timepoints are suggested for the PK study: 0.5 (±10 minutes), 6 (±10 minutes), 12 (±10 minutes), 24 (±30 minutes), 48 (±30 minutes), 72 (±30 minutes), 120 (±30 minutes) 168 (±30 minutes), 240 (±30 minutes) and 336 (±30 minutes) post inhalation exposure.

Objectives

The objective of this pilot study was to define sampling timepoints for a complete pharmacokinetic (PK) study with paclitaxel particle formulation. The preliminary data with paclitaxel particle formulation dosed by intraperitoneal (IP) injection indicate a significant retention time in the intraperitoneal cavity. Due to the potential for the paclitaxel particles formulation to result in increased retention in the lungs, time points out to 168 hours were evaluated to determine the appropriate sampling strategy for a complete pharmacokinetic study.

Materials and Methods

Test System

Species/Strain: Sprague Dawley Rats

Age of Animals at Study Start: 8-10 weeks of age

Body Weight Range at Study Start: 308-353 g

Number on Study/Sex: 18 Males (16 study animals and 2 spares)

Source: Charles River Laboratories (Kingston, N.Y.)

Identification: Permanent maker tail marking

Test and Control Article Formulation and Administration

A paclitaxel particle suspension formulation (6 mg/mL) was prepared as per instructions provided by the sponsor. Briefly, 5.0 mL of 1% Polysorbate 80 was added to the vial containing paclitaxel particles (306 mg). The paclitaxel particle suspension vial was shaken vigorously and inverted to ensure wetting of all particles present in the vial. Immediately after shaking, 46 mL of 0.9% Sodium Chloride was added to the vial and the vial was shaken for at least 1 minute to make sure sufficient mixing and proper dispersion of suspension. Resultant formulation was left undisturbed for at least 5 minutes to reduce any air/foam in the vial before placing it in the nebulizer for aerosolization work. The final formulation was kept at room temperature and used within 3 hours after reconstitution.

Experimental Design

Sixteen (16) Sprague Dawley rats were exposed to the paclitaxel particle suspension formulation (target dose of 0.37 mg/kg) by nose only inhalation on a single occasion. Two animals (n=2) were euthanatized at 0.5 (±10 minutes), 6 (±10 minutes), 12 (±10 minutes), 24 (±30 minutes), 48 (±30 minutes), 72 (±30 minutes), 120 (±30 minutes) and 168

(±30 minutes) hours post exposure for blood (plasma) and lung tissue collections. No specific PK modeling was done; rather, data will define the duration for detectable amounts of paclitaxel post exposure for the PK Study.

Husbandry, Quarantine and Assignment to Study

Male Sprague Dawley rats (6-8 weeks old) were obtained from Charles River Laboratories (Kingston, N.Y.) and quarantined for 14 days. At the end of quarantine, animals were weighed and then randomized by weight for assignment to study. Animals were identified by tail marking and cage card. Water, lighting, humidity, and temperature control were maintained and monitored using standard techniques. Rats were fed a standard rodent diet ad libitum during non-exposure hours.

Body Weights and Daily Observations

Body weights were collected at randomization, daily throughout the study and at euthanasia. Each animal on study was observed twice daily by Comparative Medicine Animal Resources (CMAR) personnel for any clinical signs of abnormality, moribundity or death.

Nose-Only Aerosol Exposures

Conditioning

Animals were conditioned to nose-only exposure tubes for up to 70 minutes using standard techniques. Three conditioning sessions occurred over three days prior to exposure, with the first session lasting 30 minutes, the second 60 minutes and the third 70 minutes. They were monitored closely throughout the conditioning periods and during exposures to assure that they did not experience more than momentary distress.

Exposure System

The inhalation exposure system consisted of two compressed air jet nebulizer (Hospitak) and a rodent nose-only inhalation exposure chamber. Exposure oxygen levels (%) were monitored throughout the exposure. A paclitaxel particle suspension formulation aerosol was generated with a set of two compressed air jet nebulizers (used for up to 40 (±1) minutes, then replaced with a second set of two compressed air jet nebulizers for remaining exposure duration) with an inlet pressure of 20 psi. The aerosol was directed through a 24-inch stainless steel aerosol delivery line (with a 1.53 cm diameter) into a nose-only exposure chamber.

Concentration Monitoring

Aerosol concentration monitoring was conducted by collecting aerosols onto pre-weighed GF/A 47-mm filters. The filters were sampled from rodent breathing zones of the nose-only exposure chamber throughout the rodent exposure. The aerosol sampling flow rate through GF/A filters were maintained at 1.0±0.5 L/minute. A total of six GF/A filters were collected, one every 10 minutes throughout the exposure duration with an exception of the last filter which was collected after 13 minutes. After sample collection, filters were weighed to determine the total aerosol concentration in the exposure system. The filters were extracted and analyzed by high performance liquid chromatography (HPLC) to quantify the amount of Paclitaxel collected on each filter. The total aerosol concentration and Paclitaxel aerosol concentrations were calculated for each filter by dividing the total amount of aerosols and Paclitaxel aerosols collected with total air flow through the filter. The average Paclitaxel aerosol concentration was used to calculate the achieved average deposited dose of Paclitaxel to the rodent lungs using equation 1 as shown below.

Particle Size Determination

Particle size distribution of aerosols was measured from rodent breathing zone of the nose-only exposure chamber by a Mercer-style, seven-stage cascade impactor (Intox Products, Inc., Albuquerque, N. Mex.). The particle size distribution was determined in terms of mass median aerodynamic diameter (MMAD) and geometric standard deviation (GSD). Cascade impactor sample was collected at a flow rate of 2.0±0.1 L/min.

Determination of Dose

Deposited dose was calculated using Equation 1. In this calculation the average aerosol concentration measured from the exposures along with average group body weights for rats were used. In this manner the estimated amount of Paclitaxel that was deposited in the rat lungs was calculated using the measured Paclitaxel aerosol concentration.

$$DD(\mu g/kg) = \frac{AC(\mu g/L) \times RMV(L/min.) \times DF \times T(min.)}{BW(kg)} \quad \text{Eqn. 1}$$

Where:

Deposited Dose=(DD) μg/kg

[2]Respiratory minute volume (RMV)=$0.608 \times BW^{0.852}$

Aerosol exposure concentration (AC)=Paclitaxel aerosol concentration (μg/L)

Deposition Fraction (DF)=assumed deposition fraction of 10%

BW=average body weight (at randomization; Day −1) of animals on study (kg)

Euthanasia and Necropsy

Animals were euthanized at their respective time points by an IP injection of euthanasia solution. During necropsy, blood (for plasma) was collected by cardiac puncture into $K_2EDTA$ tube, lungs were weighed, lung tissue samples were collected and snap frozen in liquid nitrogen for bioanalytical analyses. Additionally, a full gross examination was performed by qualified necropsy personnel. External surfaces of the body, orifices, and the contents of the cranial, thoracic, and abdominal cavities were examined. Lesions were described and recorded using a set of glossary terms for morphology, quantity, shape, color, consistency, and severity.

Bioanalytical Analyses

Systemic blood (in the form of plasma from $K_2EDTA$) and lung tissue were assayed via the liquid chromatography-mass spectrometry (LCMS) assay to quantify the amount of paclitaxel as a function of time. In brief the assay utilizes an ultra-performance liquid chromatography tandem mass spectrometry (UPLC-MS/MS) assay to quantify paclitaxel. Plasma samples are extracted via a protein precipitation method and separation is achieved via reversed phase chromatography. Lung samples were homogenized with water at a ratio of 4:1 (water:lung tissue). The homogenate then underwent a similar protein precipitation method prior to analysis on the LCMS. Quantification was conducted with a matrix based calibration curve.

No pharmacokinetic modeling was conducted on these data; however, the concentration at which paclitaxel drops below the sensitivity limits of the assay (1 ng/mL) was used to define the sampling timepoints for the main PK study.

Results

Clinical Observations and Survival

All animals survived to their designated necropsy timepoint and gained weight. No abnormal clinical observations were noted through the duration of the study.

Paclitaxel Particle Exposures
Aerosol Concentration Table 1 shows total aerosol and Paclitaxel aerosol concentrations measured by sampling each GF/A filter during exposures. The inhalation exposure average Paclitaxel aerosol concentration of 73.5 µg/L was ~11% lower from target average Paclitaxel aerosol concentration of 82.65 µg/L. The average exposure aerosol concentration was within ±15% of target aerosol concentration which was expected for nebulized inhalation exposures.

TABLE 1

Aerosol concentrations during FY17-008A inhalation exposure.

| Filter ID | Total Aerosol Conc. (mg/L) | Paclitaxel Aerosol Conc. (µg/L) |
|---|---|---|
| FS-1 | 0.230 | 68.97 |
| FS-2 | 0.236 | 71.82 |
| FS-3 | 0.240 | 77.58 |
| FS-4 | 0.268 | 87.11 |
| FS-5 | 0.205 | 62.11 |
| FS-6 | 0.237 | 73.12 |
| Average | 0.24 | 73.5 |
| SD | 0.02 | 8.4 |
| % RSD | 8.55 | 11.5 |

Necropsy

All animals survived to their designated necropsy timepoint. At necropsy several animals had minimal, red discolorations on the lungs. No other abnormal gross observations were noted at necropsy. Individual and average lung weights, body weights and ratios were determined. Average terminal bodyweight (standard deviation) was 346.26 g (24.01). Average lung weight (standard deviation) was 1.60 g (0.13). Organ lung weights and lung weight to body weight ratios are common parameters used to assess potential toxicological responses to inhaled materials. Overall, the data are in line with historical data and indicate that there was not a response with either of these endpoints.

Bioanalytical

Results are summarized below in Table 2 and FIG. 1. Average paclitaxel concentration in plasma was 16.705 ng/mL at 0.5 hours post exposure, then decreased gradually through the 24 hour timepoint and was below the lower limit of quantification (1 ng/mL) for all subsequent timepoints. Average paclitaxel concentration in lung tissue was 21940 ng/g at 0.5 hours post exposure and decreased gradually to 419.6 ng/g by the 168 hour timepoint. This indicates significant paclitaxel particle retention in the lung with minimal systemic exposure.

TABLE 2

Lung tissue and plasma results

| Animal Number | Timepoint (hr) | Plasma Concentration (ng/mL) | Lung Tissue Concentration (ng/g) | Plasma Average Conc. (ng/mL) Per timepoint | Lung Tissue Average Conc. (ng/g) Per timepoint |
|---|---|---|---|---|---|
| 1001 | 0.5 | 8.81 | 16680 | 16.705 | 21940 |
| 1002 | | 24.6 | 27200 | | |
| 1003 | 6 | 4.46 | 7800 | 4.695 | 7160 |
| 1004 | | 4.93 | 6520 | | |
| 1005 | 12 | 3.72 | 8240 | 3.720 | 6320 |
| 1006 | | <LLOQ | 4400 | | |
| 1007 | 24 | <LLOQ | 3144 | 3.140 | 4452 |
| 1008 | | 3.14 | 5760 | | |
| 1009 | 48 | <LLOQ | 2300 | <LLOQ | 2652 |
| 1010 | | <LLOQ | 3004 | | |
| 1011 | 72 | <LLOQ | 1760 | <LLOQ | 2028 |
| 1012 | | <LLOQ | 2296 | | |
| 1013 | 120 | <LLOQ | 608 | <LLOQ | 486.8 |
| 1014 | | <LLOQ | 366 | | |
| 1015 | 168 | <LLOQ | 572 | <LLOQ | 419.6 |
| 1016 | | <LLOQ | 267 | | |

Oxygen and Temperature

The recorded oxygen and temperature ranges were 19.7%-20.9% and 20.4° C.-20.8° C., respectively.

Particle Size

The particle size distribution was determined in terms of MMAD (GSD) for 6.0 mg/mL paclitaxel particle formulation aerosols using cascade impactor was 2.0 (2.2) µm.

Deposited Dose

Based on Paclitaxel average aerosol concentration of 73.5 µg/L, average rodent Day −1 (randomization) body weight of 326 g, assumed deposition fraction of 10% and exposure duration of 63 minutes; the average achieved rodent deposited dose was determined to be 0.33 mg/kg. The average achieved deposited dose was ~11% lower when compared to target deposited dose of 0.37 mg/kg due to expected variability (±15% from target) in exposure average aerosol concentration.

Conclusions

Sixteen (16) male Sprague Dawley rats were exposed to paclitaxel particle formulation aerosols (target dose of 0.37 mg/kg) by nose only inhalation on a single occasion. Two animals (n=2) were euthanatized at 0.5, 6, 12, 24, 48, 72, 120 and 168 hours post exposure for blood (plasma) and lung tissue collections.

The average Paclitaxel aerosol concentration of 73.5 µg/L during the 63 minute inhalation exposure was ~11% lower from target average Paclitaxel aerosol concentration of 82.65 µg/L. The average exposure aerosol concentration was within ±15% of target aerosol concentration which was expected for nebulized inhalation exposures. The particle size distribution was determined in terms of MMAD (GSD) for 6.0 mg/mL paclitaxel particle formulation aerosols using cascade impactor as 2.0 (2.2) µm. The recorded oxygen and temperature ranges were 19.7%-20.9% and 20.4° C.-20.8° C., respectively.

Paclitaxel deposited dose was calculated based on Paclitaxel average aerosol concentration of 73.5 µg/L, average rodent body weight of 326 g, assumed deposition fraction of 10% and exposure duration of 63 minutes. The average achieved rodent deposited dose was determined to be 0.33 mg/kg. The average achieved deposited dose was ~11% lower when compared to target deposited dose of 0.37 mg/kg due to expected variability (±15% from target).

All animals survived to their planned necropsy timepoint. At necropsy, several animals had minimal, red discolorations on the lungs. No other abnormal gross observations were noted at necropsy. From body and lung weights obtained at necropsy, average terminal bodyweight (standard deviation) was 346.26 g (24.01); and average lung weight (standard deviation) was 1.60 g (0.13). Organ lung weights and lung weight to body weight ratios are common parameters used to assess potential toxicological responses to inhaled materials. Overall, the data indicate that there was not a response with either of these endpoints.

Average paclitaxel concentration in plasma was 16.705 ng/mL at 0.5 hours post exposure, then decreased gradually through the 24 hour timepoint and was below the lower limit of quantification at all timepoints after 24 hours. Average paclitaxel concentration in lung tissue was 21940 ng/g at 0.5 hours post exposure and decreased gradually to 419.6 ng/g by the 168 hour timepoint. This indicates significant paclitaxel particle retention in the lung with minimal systemic exposure. The following sampling timepoints are suggested for the PK study: 0.5 (±10 minutes), 6 (±10 minutes), 12 (±10 minutes), 24 (±30 minutes), 48 (±30 minutes), 72 (±30 minutes), 120 (±30 minutes) 168 (±30 minutes), 240 (±30 minutes) and 336 (±30 minutes) hours post exposure.

Example 2: Study FY17-008B—Paclitaxel Particle Aerosol Inhalation Exposure Study Executive Summary The overall objective of this work was to conduct nose-only inhalation exposure to male rats with paclitaxel particle suspension formulations of 6.0 mg/mL and 20.0 mg/mL. Rat inhalation exposures were conducted for 65 minutes each.

Paclitaxel particle suspension formulations of 6.0 mg/mL and 20.0 mg/mL were prepared as per instructions provided by the sponsor. Two Hospitak compressed air jet nebulizers were used simultaneously at 20 psi for aerosolization of paclitaxel particle formulation into the rodent inhalation exposure chamber. During each exposure, aerosol concentration was measured from animal breathing zone by sampling onto 47-mm GF/A filters at a flow rate of 1.0±0.5 L/minute. Particle size was determined by sampling aerosols from animal breathing zone using Mercer style cascade impactor at a flow rate of 2.0±0.1 L/minute. Filters were analyzed gravimetrically to determine total paclitaxel particle aerosol concentration and via high performance liquid chromatography (HPLC) to determine Paclitaxel aerosol concentration for each exposure. Oxygen and temperature were monitored and recorded throughout the inhalation exposures.

The average total paclitaxel particle aerosol concentration and Paclitaxel aerosol concentration were determined to be 0.25 mg/L with a RSD of 7.43% and 85.64 µg/L with a RSD of 10.23%, respectively for inhalation exposures conducted with 6.0 mg/mL paclitaxel particle formulation. The measured average mass median aerodynamic diameter (geometric standard deviation) using cascade impactor was 1.8 (2.0) µm for 6.0 mg/mL paclitaxel particle formulation aerosols. The average total paclitaxel particle aerosol concentration and Paclitaxel aerosol concentration were determined to be 0.46 mg/L with a RSD of 10.95% and 262.27 µg/L with a RSD of 11.99%, respectively for inhalation exposures conducted with 20.0 mg/mL paclitaxel particle formulation. The measured average mass median aerodynamic diameter (geometric standard deviation) using cascade impactor was 2.3 (1.9) µm for 20.0 mg/mL paclitaxel particle formulation aerosols.

The average Paclitaxel deposited dose of 0.38 mg/kg and 1.18 mg/kg were calculated using equation 1 for a 65 minute exposure for 6.0 mg/mL and 20.0 mg/mL paclitaxel particle formulation, respectively.

Formulation and Inhalation Exposure
Formulation Preparation
Materials
Test Article
The test article used for inhalation exposure is shown below.
Paclitaxel Particles
Identity: Paclitaxel particles (sterile)
Description: Novel dry powder formulation of Paclitaxel delivered as 306 mg/vial
Supplier: US Biotest
Manufacturer: CritiTech
Storage Conditions: Ambient
Vehicle
The vehicles used for preparation of paclitaxel particle formulations are shown below.
Polysorbate 80
Identity: Sterile 1% Polysorbate 80 in 0.9% sodium chloride for injection
Description: Clear liquid
Supplier: US Biotest
Manufacturer: CritiTech
Storage Conditions: Ambient
Normal Saline
Identity: Sterile 0.9% sodium chloride for injection, USP
Description: Clear liquid
Manufacturer: Hospira, Inc, IL
Storage Conditions: Ambient
Formulation and Inhalation Exposure
Formulation Preparation Paclitaxel particle formulation of 6.0 mg/mL was prepared as follows: Briefly, 5.0 mL of 1% Polysorbate 80 was added to the vial containing paclitaxel particles (306 mg). The vial was shaken vigorously and inverted to ensure wetting of all particles present in the vial. Immediately after shaking, 46 mL of 0.9% Sodium Chloride solution was added to the vial and vial was shaken for at least 1 minute to make sure sufficient mixing and proper dispersion of suspension.

The paclitaxel particle formulation procedure described above for 6.0 mg/mL formulation was used to prepare 20.0 mg/mL paclitaxel particle formulation with an exception of 10.3 mL of 0.9% sodium chloride solution was added to the vial instead of 46 mL used for the 6.0 mg/mL formulation.

Resultant formulations were left undisturbed for at least 5 minutes to reduce any air/foam in the vial before placing it in nebulizer for aerosolization work. The final formulation of 6.0 mg/mL was kept at room temperature and nebulized within 2 hours after reconstitution. The final formulation of 20.0 mg/mL was kept at room temperature and nebulized within 30 minutes after reconstitution.

Experimental Design

Thirty (30) Sprague Dawley rats were exposed to a single "clinical reference" dose of intravenous ABRAXANE® (paclitaxel: target dose 5.0 mg/kg), thirty (30) Sprague Dawley rats were exposed to the paclitaxel particle formulations disclosed herein (target dose of 0.37 mg/kg) and thirty (30) Sprague Dawley rats were expose to the paclitaxel particle formulations (target dose of 1.0 mg/kg) by nose only inhalation on a single occasion. Three animals (n=3) were euthanatized at 0.5 (±10 minutes), 6 (±10 minutes), 12 (±10 minutes), 24 (±30 minutes), 48 (±30 minutes), 72 (±30 minutes), 120 (±30 minutes), 168 (±30 minutes), 240 (±30 minutes), and 336 (±30 minutes) hours post exposure for blood (plasma) and lung tissue collections. Non-compartmental analyses were performed on plasma and lung tissue to identify duration of detectable amounts of paclitaxel post exposure for each dose group.

Exposure System Set-up/Aerosol Generation: As in example 1
Aerosol Concentration Monitoring: As in Example 1
Particle Size Distribution: As in Example 1
Deposited Dose Calculation: As in Example 1
Results
Exposure Results
Aerosol Concentration and Particle Size Aerosol concentration was monitored throughout each paclitaxel particle formulation aerosol exposure using 47-mm GF/A filters from breathing zone of the animals on nose-only exposure chamber. Seven 47-mm GF/A filters were sampled during each exposure. Filters FS-1 through FS-6 were sampled for 10 minutes each and filter FS-7 was sampled for 5 minutes during each low and high dose groups. Particle size was measured using Mercer style cascade impactor from animal breathing zone on the exposure chamber. Tables 3 and 4 show total and Paclitaxel aerosol concentrations measured by sampling GF/A filters during low dose and high dose exposures, respectively.

TABLE 3

Aerosol concentrations during FY17-008B low dose inhalation exposure.

| Filter ID | Total Aerosol Conc. (mg/L) | Paclitaxel Aerosol Conc. (µg/L) |
|---|---|---|
| FS-1-L | 0.247 | 80.05 |
| FS-2-L | 0.242 | 81.79 |
| FS-3-L | 0.252 | 87.09 |
| FS-4-L | 0.296 | 104.38 |
| FS-5-L | 0.247 | 78.47 |
| FS-6-L | 0.249 | 82.50 |
| FS-7-L | 0.244 | 85.19 |
| Average | 0.25 | 85.64 |
| SD | 0.02 | 8.76 |
| % RSD | 7.43 | 10.23 |

TABLE 4

Aerosol concentrations during FY17-008B high dose inhalation exposure.

| Filter ID | Total Aerosol Conc. (mg/L) | Paclitaxel Aerosol Conc. (µg/L) |
|---|---|---|
| FS-1-H | 0.383 | 212.53 |
| FS-2-H | 0.412 | 239.28 |
| FS-3-H | 0.494 | 291.44 |
| FS-4-H | 0.516 | 296.56 |
| FS-5-H | 0.456 | 254.67 |
| FS-6-H | 0.501 | 289.50 |
| FS-7-H | 0.431 | 251.88 |
| Average | 0.46 | 262.27 |
| SD | 0.05 | 31.45 |
| % RSD | 10.95 | 11.99 |

The particle size (aerosol droplet size) distribution was determined in terms of MMAD (Median of the distribution of airborne particle mass with respect to the aerodynamic diameter) (GSD; accompanies the MMAD measurement to characterize the variability of the particle size distribution) for each paclitaxel particle formulation aerosols using cascade impactor. For 6.0 mg/mL and 20.0 mg/mL paclitaxel particle formulation aerosols the MMAD (GSD) were determined to be 1.8 (2.0) μm and 2.3 (1.9) μm, respectively. FIGS. 2 and 3 show particle size distribution for 6.0 mg/mL and 20.0 mg/mL paclitaxel particle formulations aerosols, respectively.

Deposited Dose

Paclitaxel deposited dose was calculated based on Paclitaxel average aerosol concentration, average rat body weight, assumed deposition fraction of 10% and exposure duration of 65 minutes for each low dose and high dose paclitaxel particle formulation exposures by using equation 1. Table 5 shows average Paclitaxel aerosol concentration, average rat body weight, exposure time and deposited dose for each exposure. The average achieved rodent deposited dose was determined to be 0.38 mg/kg and 1.18 mg/kg for 6.0 mg/kg and 20.0 mg/kg paclitaxel particle formulation exposures, respectively.

TABLE 5

Paclitaxel deposited dose for low and high dose paclitaxel particle formulation inhalation exposures.

| Dose Level | paclitaxel particles Formulation Conc. (mg/mL) | Paclitaxel Avg. Aerosol Conc. (μg/L) | Avg. Rat Weight (g) | Exposure Time (min.) | Deposited Dose (mg/kg) |
|---|---|---|---|---|---|
| Low | 6.0 | 85.64 | 420.4 | 65 | 0.38 |
| High | 20.0 | 262.27 | 420.5 | 65 | 1.18 |

Oxygen and Temperature

Oxygen and temperature were monitored throughout the paclitaxel particle formulation aerosols exposures. The recorded oxygen and temperature ranges were 19.8%-20.9% and 20.7° C.-20.8° C., respectively for 6.0 mg/mL paclitaxel particle formulation exposure. For 20.0 mg/mL paclitaxel particle formulation exposure, the recorded oxygen value was 19.8% throughout the exposure and temperature range was 20.7° C.-20.8° C.

Preliminary data is shown in FIGS. 4-6.

Example 3 Evaluating Efficacy of Inhaled Paclitaxel Particle Formulations in the Nude Rat Orthotopic Lung Cancer Model—Study FY17-095

Executive Summary

One hundred twenty-seven (127) NIH-rnu Nude Rats were x-irradiated to induce immunosuppression on Day −1. On Day 0 animals were dosed with Calu3 tumor cells by intratracheal (IT) instillation. Animals underwent a growth period of three weeks. During the third week, animals were randomized by body weight stratification into 5 study groups. Starting Week 4, animals in Group 2 received a once weekly dose of ABRAXANE® by intravenous (IV) dosing (5 mg/kg) on Days 22, 29 and 36. Animals in Groups 3 and 4 received once weekly (Monday) inhalation (INH) dose of paclitaxel particle formulations at low (0.5 mg/kg) and high (1.0 mg/kg) target doses, respectively. Animals in Groups 5 and 6 received a twice weekly (Monday and Thursday) target inhalation dose of paclitaxel particle formulations at low (0.50 mg/kg) and high (up to 1.0 mg/kg) doses respectively. Animals in Group 1 were left untreated as a control of normal tumor cell growth. All animals were necropsied during Week 8.

All animals survived to their designated necropsy timepoint. Clinical observations related to the model included skin rash and labored breathing. All groups gained weight at about the same rate throughout the course of the study.

The inhalation exposure average Paclitaxel aerosol concentration for once weekly Low Dose and twice weekly Low Dose paclitaxel particle formulation groups was 270.51 µg/L and 263.56 µg/L, respectively. The inhalation exposure average Paclitaxel aerosol concentration for once weekly High Dose and twice weekly High Dose paclitaxel particle formulation groups was 244.82 µg/L and 245.76 µg/L, respectively.

Doses were based on average aerosol paclitaxel concentration, most recent average group bodyweight, the assumed deposition fraction of 10%, and an exposure duration of 33 (Low-Dose) or 65 (High-Dose) minutes. During four weeks of treatment, the average achieved rodent deposited dose for the once weekly Low Dose paclitaxel particles formulation group and twice weekly Low Dose paclitaxel particles formulation group were 0.655 mg/kg and 0.640 mg/kg (1.28 mg/kg/week), respectively. The average achieved rodent deposited dose for the once weekly High Dose paclitaxel particles formulation group and twice weekly High Dose paclitaxel particles formulation group were 1.166 mg/kg and 1.176 mg/kg (2.352 mg/kg/week), respectively. For the group receiving IV injections of ABRAXANE®, the average dose on Day 22, 29 and 36 was 4.94, 4.64 and 4.46 mg/kg respectively.

At scheduled necropsy, the majority of animals from each group had tan nodules on the lungs and/or red or tan patchy discolorations of the lung. Other sporadic observations included an abdominal hernia in one animal and a nodule on the pericardium in another animal. No other abnormal gross observations were noted at necropsy.

In the ABRAXANE® treated animal's lung weights, the lung to BW ratios and lung to brain weight ratios were significantly lower compared to Untreated Controls. The once weekly paclitaxel particle formulation High Dose group had similar weights to the ABRAXANE® group and significantly lower lung weights and lung to brain ratios compared to Untreated Controls.

Histologically, lungs of the majority of animals in all groups contained some evidence of tumor formation. Tumor formation was characterized by the presence of expansile variably sized small masses randomly scattered within the lung parenchyma and larger expanded and coalescing masses that effaced up to 75% of the lung parenchyma, smaller airways and blood vessels. The larger masses were distributed primarily in the hilar regions or juxtaposed at the axial airway and the smaller masses were generally located peripherally.

The primary morphologic cellular characteristics of the lung tumor masses varied from the presence of undifferentiated to a fairly well differentiated pattern of adenocarcinoma of the lung. The predominant tumor cell type showed an undifferentiated adenocarcinoma morphology; the cells were pleomorphic, large, anaplastic, pale amphophilic-staining with fine intracytoplasmic vacuoles resembling mucoid vesicles, exhibited moderate to marked anisokaryosis, and were observed to be individualized or growing in sheets and lacking clear-cut features towards differentiation to adenocarcinoma. However, the cellular morphologic characteristics that were observed within other masses or growing within the previously described undifferentiated masses were more organized and consistent with well differentiated lung adenocarcinoma demonstrating clear acinar gland differentiation. These amphophilic staining tumor cells were primarily arranged in nests or glandular patterns which were observed to be bound by alveolar septae. Mitotic figures were rarely observed in this tumor cell population. Less frequently observed within these masses were focal areas of primitive-appearing relatively small Primitive Tumor Cells with small to moderate amounts of pale basophilic staining cytoplasm, ovoid and variably vesicular nuclei, and moderate anisokaryosis. These Primitive Tumor Cells were observed to be growing randomly and in sheets. Increased numbers of mitotic figures and apoptotic bodies were noted most often in this basophilic Primitive Tumor Cell population. Inflammation, characterized by mixed inflammatory cell (predominately eosinophils, lymphocytes, foamy macrophages and the occasional giant cell) infiltration accompanied by interstitial fibrosis was commonly observed. Significant parenchymal necrosis was uncommon to absent.

The pathologist considered the presence of scalloping of the edges of the individual tumor masses characterized by gradual loss of tumor cells, to complete loss of tumor cells with residual fibrosis connective tissue scaffolding of the lung parenchyma and accompanied by invasion of foamy macrophages to be evidence of Tumor Regression.

Compared to the positive control Grp. 1 and the ABRAXANE® treated comparative Grp. 2, there was a decreased overall lung tumor burden in the paclitaxel particle formulation treated groups (Grp. 3-6) characterized by a decrease in the severity of adenocarcinoma tumor masses and Primitive Tumor Cell population as well as evidence of Tumor Regression. No other treatment-related lesions or findings were observed. Extensive mononuclear cell infiltration was observed in the lungs of animals receiving paclitaxel particle formulation through inhalation. As the model used is T cell deficient, it is likely that the cells are B cells or NK cells. It is hypothesized that the localized, likely higher concentration exposure of the tumor to paclitaxel particles affected the tumors leading to an alteration in the environment to draw the mononuclear cellular infiltrate into the lung.

Objectives

The objective of this study was to evaluate the efficacy of inhaled paclitaxel particle formulation compared to a clinical reference dose of intravenous administered ABRAXANE® in reducing tumor burden in an orthotopic model of lung cancer.

Materials and Methods

Test System

Species/Strain: NIH-rnu Nude Rats

Age of Animals at Study Start: 3-5 weeks old

Body Weight Range at Study Start: Approximately 150-200 g

Number on Study/Sex: 127 Males (120 study animals and 7 spares)

Source: Envigo

Identification: Permanent maker tail marking

ABRAXANE® Formulation

The clinical reference material used for IV formulation was the drug product ABRAXANE®. The drug product was reconstituted to 5.0 mg/mL with saline on the day of dosing and was stored per manufacturer's instructions.

Paclitaxel Particle Formulation

The 20.0 mg/ml paclitaxel particle formulations for exposures were prepared per the sponsor recommendations. Specifically, the paclitaxel particles were reconstituted with 1% polysorbate 80. The vial was shaken by hand until all particles were wetted. Additional 0.9% sodium chloride for injection was added (to the desired concentration target) and the vial was shaken by hand for another minute. Shaking continued until no large clumps were visible and the suspension was properly dispersed.

Resultant formulations were left undisturbed for at least 5 minutes to reduce any air/foam in the vial before placing it in a nebulizer for aerosolization work. The final formulation was kept at room temperature and nebulized within 2 hours after reconstitution. The final 20.0 mg/mL was kept at room temperature and nebulized within 30 (+5) minutes after reconstitution.

Experimental Design

One hundred twenty-seven (127) animals were used for study. Prior to x-irradiation and dosing of tumor cells, 7 animals were designated as spares (spare animals did not have irradiations or cell line instillations). On Day −1 all study animals were x-irradiated to induce immunosuppression. On Day 0 animals were dosed with Calu3 tumor cells by intratracheal (IT) instillation. Animals underwent a growth period of three weeks. During the third week, animals were randomized by body weight stratification into the groups outlined in Table 6 below. Starting Week 4, animals in Group 2 received a once weekly target dose of ABRAXANE® by intravenous (IV) dosing (5 mg/kg). Animals in Groups 3 and 4 received once weekly (Monday) inhalation (INH) target dose of paclitaxel particle formulations at low (0.5 mg/kg) and high (1.0 mg/kg) doses, respectively. Animals in Groups 5 and 6 received a twice weekly (Monday and Thursday) inhalation target dose of paclitaxel particle formulations at low (0.50 mg/kg) and high (1.0 mg/kg) respectively. Animals in Group 1 were left untreated as a control of normal tumor cell growth. All animals were necropsied during Week 8.

Husbandry, Quarantine and Assignment to Study

After quarantine all animals were weighed and randomized to remove the 7 spares based on body weights. From Week 1 to Week 3 animals were identified by cage cards (LC numbers) and tail markings.

During Week 3, prior to beginning treatment, animals were weighed and randomized into the groups listed above by body weight stratification and assigned a Study ID. From this point forward, animals were identified by cage cards and sharpie tail marking.

Immunosuppression and Irradiation

On Day −1, animals underwent whole body x-ray exposure with ~500 rads (Phillips RT 250 X-ray Therapy Unit, Phillips Medical Systems, Shelton, Conn.) set at 250 kVp, 15 mA, and a source-to-object distance of 100 cm. The animals were placed in a pie chamber unit, 2-3 animals per slice of pie. The irradiation process took ~10-15 minutes.

Tumor Cell Implantation

On Day 0, animals received tumor cells (Calu3) administered by IT. Briefly, after being anesthetized by 3-5% isoflurane in an induction chamber, the animal was placed with upper incisors hooked on an inclined hanging instillation platform. The animals tongue was gently secured while the stylet is inserted just past the larynx and into the trachea. A volume of cells in EDTA suspension (target dose volume: 500 µL; concentration: approximately $20 \times 10^6$ per 0.5 mL) was delivered to the lungs via intratracheal instillation. After the instillation, the animals' breathing and movement was monitored carefully. Following tumor cell implantation, animals underwent a tumor growth period of approximately 3 weeks prior to treatment to allow for tumor cell engraftment and the development of lung cancer.

TABLE 6

Experimental Design

| Group Description | N= | Irradiation | Cell Line | Route | Target Dose and Frequency* | Treatment Formulation | Exposure Duration | Necropsy* |
|---|---|---|---|---|---|---|---|---|
| 1 Control | 20 | Day −1 | Calu 3, IT instillation Day 0 | N/A | N/A | N/A | N/A | Week 8 |
| 2 IV ABRAXANE® | 20 | | | IV | up to 5 mg/kg** | ABRAXANE® (5 mg/ml) | N/A | |
| 3 paclitaxel particle formulation Low Once Weekly (1×) | 20 | | | INH | 0.5 mg/kg, once weekly | 20.0 mg/mL paclitaxel particle formulation | 33 min | |
| 4 paclitaxel particle formulation High Once Weekly (1×) | 20 | | | INH | 1.0 mg/kg, once weekly | 20.0 mg/mL paclitaxel particle formulation | 65 min | |
| 5 paclitaxel particle formulation Low- Twice Weekly (2×) | 20 | | | INH | 0.5 mg/kg, twice weekly | 20.0 mg/mL paclitaxel particle formulation | 33 min | |
| 6 paclitaxel particle formulation High Twice Weekly (2×) | 20 | | | INH | 1.0 mg/kg, twice weekly | 20.0 mg/mL paclitaxel particle formulation | 65 min | |

*Treatment occurred during Week 4-8. Necropsy occurred during Week 8.
**ABRAXANE® target dose: 5.0 mg/kg based on bodyweight; target dose volume: not to exceed 250 µL, frequency: Day 1, 8, and 15 of each 21 day cycle beginning during Week 4.

Calu3 Growth and Preparation

Calu3 cells were grown at 37° C. with 5% $CO_2$ in cell culture flasks. They were grown in Roswell Park Memorial Institute (RPMI) 1640 media with 10% fetal bovine serum (FBS) until 80% confluence. Cells were maintained until the day of instillation. Prior to instillation they were harvested by washing with PBS, then trypsin was added to remove cells from the flask. The cells were neutralized with RPMI 1640 media containing 10% FBS. They were then centrifuged at 100×g for 5 minutes; the media was removed and the cells were resuspended to a concentration of 20 million cells in 450 µL of serum free RPMI. Prior to instillation, 50 µL of 70 µM EDTA was added to the cell suspension for a total IT dose volume of 500 µL per rat.

Body Weights and Daily Observations

Body weights were collected for randomization, weekly through Week 3, twice weekly beginning at Week 4 through the end of the study, and at necropsy.

Each animal on study was observed twice daily for any clinical signs of abnormality, morbidity or death. Technicians observed animals during dosing and bodyweight sessions.

ABRAXANE® Administration IV-Tail Vein Injections

ABRAXANE® (5 mg/mL, maximum dose volume of 250 µL) was administered to animals in Group 2 by IV tail vein injection on Days 22, 29 and 36.

Paclitaxel Particle Formulation Administration—Nose-Only Aerosol Exposures Conditioning Animals were conditioned to nose-only exposure tubes for up to 70 minutes. Three conditioning sessions occurred over three days prior to exposure, with the first session lasting 30 minutes, the second 60 minutes and the third 70 minutes. They were monitored closely throughout the conditioning periods and during exposures to assure that they did not experience more than momentary distress.

Exposure System

Figure 7:
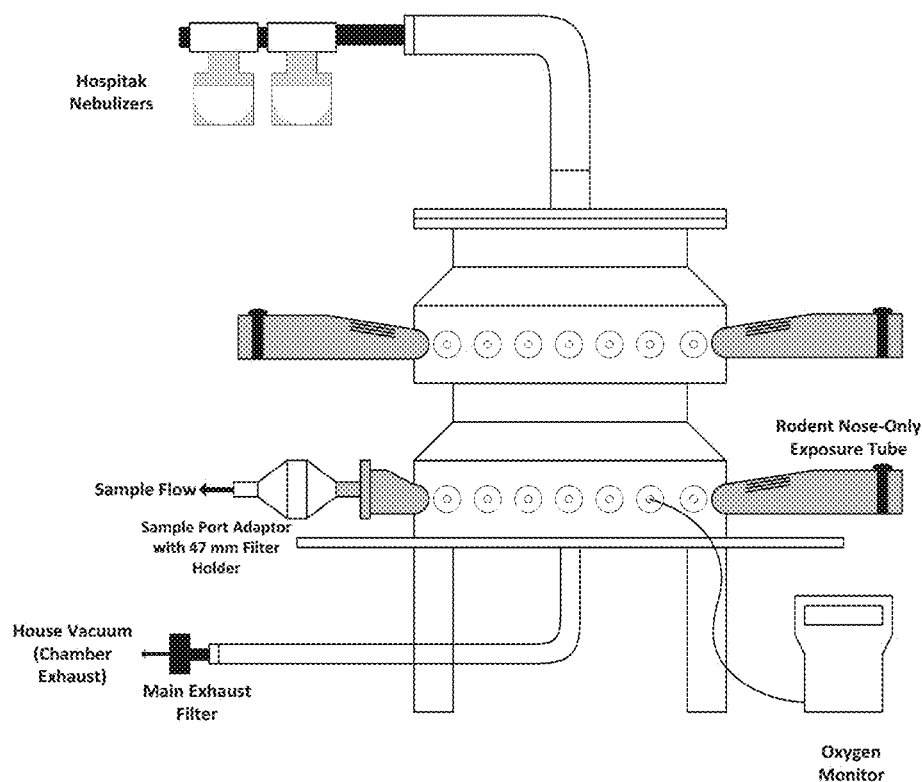
FIG. 7 is a diagram of a compressed air jet Hospitak nebulizer.

Aerosols were generated with two compressed air jet Hospitak nebulizers as shown in FIG. 7 at a nebulizer pressure of 20 psi. paclitaxel particle suspension formulation of 20.0 mg/mL was used for low dose and high dose exposures. Aerosols were directed through a delivery line into a 32-port nose-only exposure chamber. The rodent inhalation exposures were conducted for 33 or 65 minutes. paclitaxel particle suspension aerosol was generated with a set of two Hospitak compressed air jet nebulizers (used for up to 40 (±1) minutes, then replaced with a second set of two Hospitak nebulizers for remaining exposure duration. Oxygen and temperature were monitored and recorded throughout each inhalation exposure Concentration Monitoring Aerosol concentration monitoring was conducted by collecting aerosols onto pre-weighed GF/A 47-mm filters. The filters were sampled from animals breathing zones of the nose-only exposure chamber throughout each inhalation exposure. The aerosol sampling flow rate through GF/A filters was maintained at 1.0±0.5 L/minute. Filters were collected throughout each exposure duration every 10-minutes except for the last filter. With the low-dose exposures (groups 3 and 5) lasting 33 minutes, the final filter was collected after 13 minutes and with the high-dose exposures (groups 4 and 6) lasting 65 minutes, the final filter was collected after 15 minutes. After sample collection filters were weighed to determine the total aerosol concentration in the exposure system.

Post weighing, each filter was placed in a 7 mL glass vial. The filters in glass vials were extracted and analyzed by High Performance Liquid Chromatography (HPLC) to quantify the amount of Paclitaxel collected onto the filters. The total aerosol concentration and Paclitaxel aerosol concentrations were calculated for each filter by dividing the total amount of aerosols and Paclitaxel aerosols collected with total air flow through the filter. The average Paclitaxel aerosol concentration was used to calculate the achieved average deposited dose of Paclitaxel to the rodent lungs using Equation 1 as shown in the Determination of Dose section below.

Determination of Dose

Deposited dose was calculated using Equation 1. In this calculation the average aerosol concentration measured from the exposures along with average group body weights for rats were used. In this manner the estimated amount of Paclitaxel deposited in the rat lungs was calculated using the measured Paclitaxel aerosol concentration.

$$DD(\mu g/kg) = \frac{AC(\mu g/L) \times RMV(L/min) \times DF \times T(min)}{BW(kg)} \quad \text{Equation 1}$$

Where:
Deposited Dose=(DD) µg/kg
²Respiratory minute volume (RMV)=$0.608 \times BW^{0.852}$
Aerosol exposure concentration (AC)=Paclitaxel aerosol concentration (µg/L)
Deposition Fraction (DF)=assumed deposition fraction of 10%
BW=average body weight (at randomization; Day −1) of animals on study (kg)

Euthanasia and Necropsy

At scheduled necropsy, animals were euthanized by intraperitoneal injection of an overdose of a barbiturate-based sedative.

Blood and Tissue Collection

For all necropsies a terminal body weight and brain weight was collected. For scheduled euthanasia blood (for plasma) was collected by cardiac puncture into a $K_2$EDTA tube. The lungs were removed and weighed. A section of lung tissue containing a tumor, a tracheobronchial lymph node, was frozen in liquid nitrogen for potential future analysis. The remaining lung was fixed for potential histopathology.

Histopathology

Fixed left lung lobes were trimmed in a "bread loaf" manner and alternate sections were placed in 2 cassettes to yield 2 slides each with 3 representative sections of the left lung. Tissues were processed routinely, paraffin embedded, sectioned at ~4 µm, mounted, and stained with hematoxylin and eosin (H&E) for microscopic examination. Findings were graded subjectively, semi-quantitatively.

Sections of lung (1-4/animal) obtained from 60 out of the 120 treated nude rats on study, trimmed longitudinally, were processed to H & E stained glass slides for light microscopic evaluation.

During this review, the microscopic findings were recorded and then transferred to an electronic pathology reporting system (PDS-Ascentos-1.2.0, V.1.2), which summarized the incidence and severities of the lung burden characteristics data and tabulated the results and generated the individual animal data. The lungs from the 60 nude rats were examined histologically: Group 1 [1001-1010], Group 2 [2001-2010], Group 3 [3001-3010], Group 4 [4001-4010], Group 5 [5001-5010] and Group 6 [6001-6010]). In order to assess the level of tumor burden in these lungs, the lungs were evaluated and scored during histopathologic examination. For each cumulative lung burden characteristic diagnosis: 1) Adenocarcinoma (undifferentiated and differentiated), 2) Primitive Tumor Cells (poorly differentiated pleomorphic cells) and 3) Tumor Regression, the lungs were graded semi-quantitatively using a 4-point grading scale indicating the percent involvement of the overall lung tissue provided as follows: 0=no evidence, 1=minimal (~1-25% total area of lung sections involved), 2=mild (~25-50% total area of lung sections involved), 3=moderate (~50-75% total area of lung sections involved), and 4=marked (~75-100% total area of lung sections involved).

HistoMorphometry

Histomorphometric analyses was performed using fixed left lung lobes of the first 10 animals from each group. Tissue was trimmed using a morphometry ("bread slice") style trim. Briefly, trimming started at a random point between 2 and 4 mm from the cranial end of the lung. Each lung section was cut approximately 4 mm thick. Odd numbered sections were placed caudal side down in cassette 1 while even numbered sections were placed in cassette 2. Tissue sections were then processed, paraffin embedded, and sectioned at 4 µm and stained with hematoxylin and eosin (HE) for examination. Both slides (odd and even slices) were used to determine an average tumor fraction per animal.

Morphometric analysis was performed on the hematoxylin and eosin (HE) stained lung tissue from the designated animals by Lovelace Biomedical. Whole slides (2 per animal containing transverse sections of the entire left lung) were scanned using a Hamamatsu Nanozoomer. Scans were analyzed with Visiopharm Integrator System software (VIS, version 2017.2.5.3857). Statistical analysis of tumor area fraction was performed in GraphPad Prism 5 (version 5.04).

Computerized image quantification designed to quantify the amount of tumor area present on each slide was performed on all left lung tissue using the whole slide scans. The Visiopharm Application for quantifying the area of lung metastases was used to differentiate tumor cells from normal lung tissue based on cell density, staining intensity, and size and staining intensity. It is noted that this quantitation based upon simple H&E staining will not be perfect (i.e. it is not capable of fully discriminating between types of tumor tissue, necrotic and viable tumor tissue, and some normal structures may be included as tumor). The value in application of this process to H&E sections is that it is an unbiased approach to tumor quantification. The area of the whole piece of lung is determined, and the area occupied by structures identified as metastases is then expressed as a percentage of the total area. Minor adjustment of the area to be analyzed to ensure extrapulmonary structures are excluded and the entire lung is included may be performed manually. Other manual manipulations are avoided in order to ensure consistency across all groups and remove potential for introduction of bias. If possible, development of specific immunohistochemical stains to identify only tumor tissue would increase specificity of this analysis.

Blood Collection and Processing

Blood collected at necropsy was processed to plasma by centrifugation at a minimum of 1300 g at 4° C. for 10 minutes. Plasma samples were stored at −70 to −90° C. until analysis or shipment to sponsor.

Results

Clinical Observation, Survival, and Bodyweights

All animals survived to their designated necropsy timepoint. Clinical observations related to the model included skin rash and labored breathing. One animal was observed to have an upper abdominal hernia. Per vet recommendation the animal was switched with a Group 1 (Untreated Control) that would not undergo inhalation exposures therefore no exposure tube restraint would be necessary.

Figure 8:
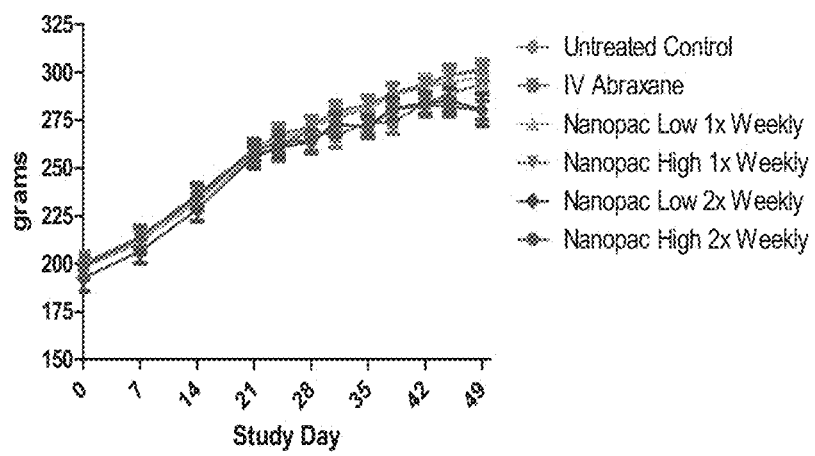
FIG. 8 is a graph of animal body weight over time from Orthotopic Lung Cancer study.
Figure 9:
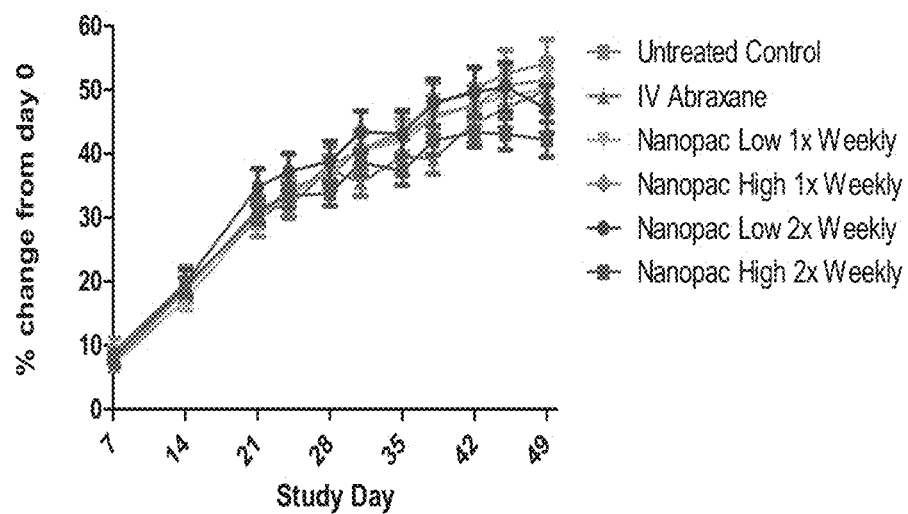
FIG. 9 is a graph of animal body weight change over time from Orthotopic Lung Cancer study.

FIG. 8 shows the average body weights through the duration of the study. FIG. 9 shows the percent change in average body weights from Day 0. All groups gained weight at about the same rate through the course of the study.

ABRAXANE® IV Tail Vein Injections

For the group receiving IV injections of ABRAXANE®, the average dose on Day 22, 29 and 36 was 4.94, 4.64 and 4.46 mg/kg respectively.

Paclitaxel Particle Exposures

Aerosol Concentrations and Deposited Dose

Total aerosol and Paclitaxel aerosol concentrations were measured by sampling of GF/A filters during each exposure. The inhalation exposure average Paclitaxel aerosol concentration for once weekly Low Dose and twice weekly Low Dose paclitaxel particle formulation groups were of 270.51 µg/L and 263.56 µg/L, respectively. The inhalation exposure average Paclitaxel aerosol concentration for once weekly High Dose and twice weekly High Dose paclitaxel particle formulation groups were of 244.82 µg/L and 245.76 µg/L, respectively. The oxygen and temperature levels were monitored throughout each exposure.

Doses were based on average aerosol paclitaxel concentration, most recent average group bodyweight, the assumed deposition fraction of 10% and an exposure duration of 33 or 65 minutes. During four weeks of treatment, the average achieved rodent deposited dose for the once weekly Low Dose paclitaxel particle formulation group and twice weekly Low Dose paclitaxel particle formulation group were 0.655 mg/kg and 0.640 mg/kg (1.28 mg/kg/week), respectively.

The average achieved rodent deposited dose for the once weekly High Dose paclitaxel particle formulation group and twice weekly High Dose paclitaxel particle formulation group were 1.166 mg/kg and 1.176 mg/kg (2.352 mg/kg/week), respectively.

Particle Size (MMAD & GSD)

The particle size distribution was determined in terms of Mass Median Aerodynamic Diameter (MMAD) and Geometric Standard Deviation (GSD) for each paclitaxel particle formulation aerosols using cascade impactor. For the 20.0 mg/mL paclitaxel particle formulation aerosols the average MMAD was determined to be 2.01 µm and a GSD of 1.87.

Necropsy Observations and Organ Weights

All animals survived to their designated necropsy timepoint. At necropsy animals from each group had tan nodules on the lungs and/or red or tan patchy discolorations of the lung. Other sporadic observations included an abdominal hernia in one animal and a nodule on the pericardium in another animal. No other abnormal gross observations were noted at necropsy. One animal did not have any visible tumors (nodules) at the time of necropsy.

Figure 10:
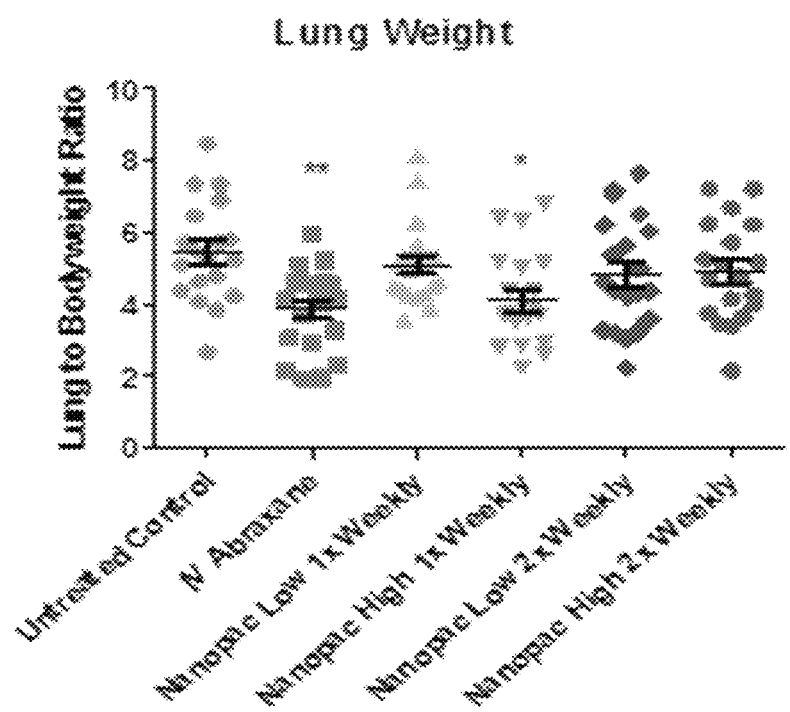
FIG. 10 is a plot of animal lung weights from Orthotopic Lung Cancer study.
Figure 11:
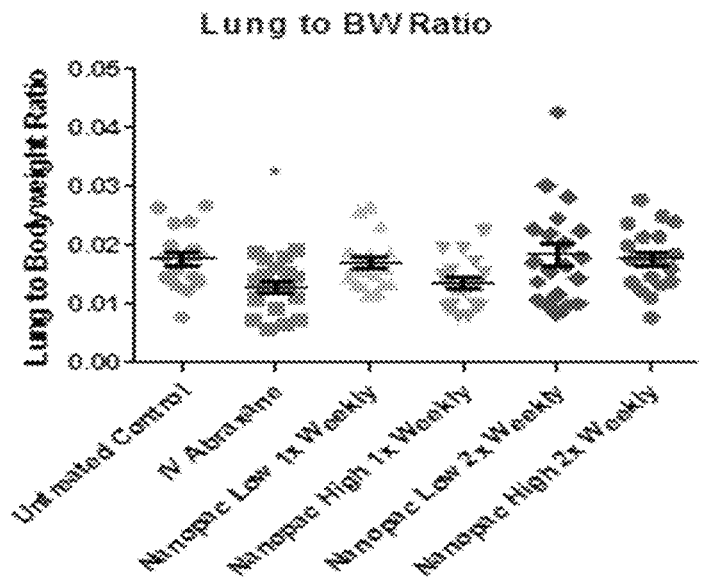
FIG. 11 is a plot of animal lung to body weight ratios from Orthotopic Lung Cancer study.
Figure 12:
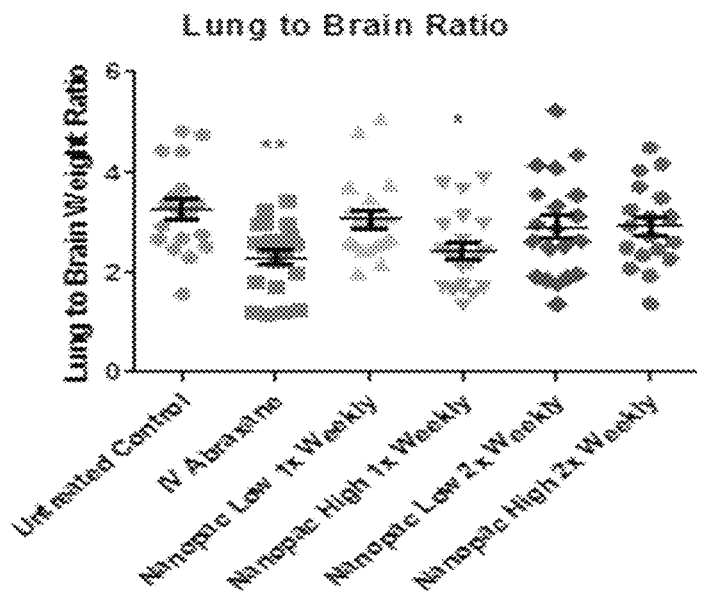
FIG. 12 is a plot of animal lung to brain weight ratios from Orthotopic Lung Cancer study.

Individual animal organ weight data is shown graphically in FIG. 10, FIG. 11 and FIG. 12. In ABRAXANE® treated animal's lung weights, lung to BW ratios and lung to brain weight ratios were significantly lower compared to Untreated Controls. The once weekly paclitaxel particle formulation High Dose group had similar weights to the ABRAXANE® group and significantly lower lung weights and lung to brain ratios compared to Untreated Controls. The once weekly Low Dose, paclitaxel particle formulation twice weekly Low Dose and twice weekly High Dose paclitaxel particle formulation groups generally had similar average lung weights and ratios.

Morphometry

Figure 13:
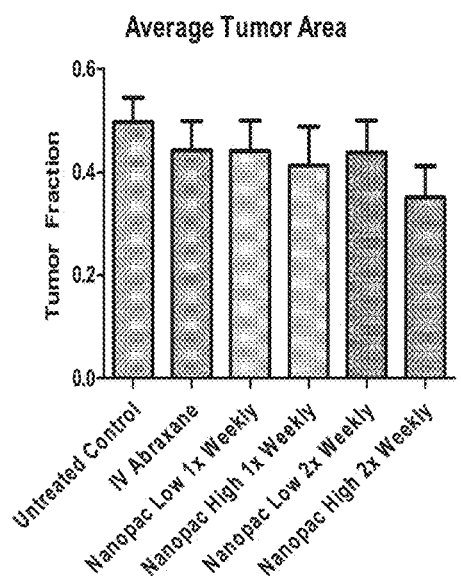
FIG. 13 is a graph of average tumor areas from Orthotopic Lung Cancer study.
Figure 14:
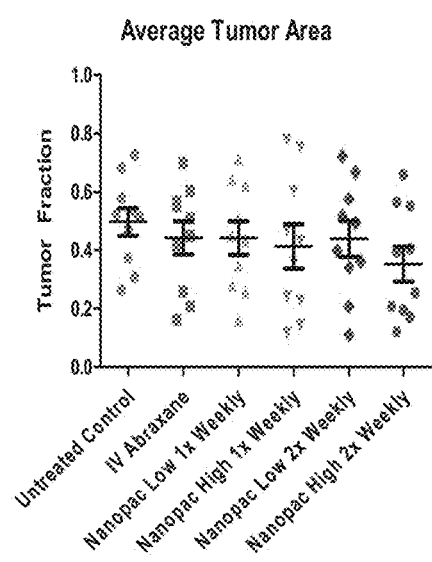
FIG. 14 is a plot of average tumor areas from Orthotopic Lung Cancer study.

All treatment groups showed a decrease in average lung tumor fraction when compared to the control group; however, there was no statistically significant difference between groups. There was also no statistically significant difference between IV ABRAXANE® treatment and any of the paclitaxel particle formulation treatment regimens in regards to the tumor area fraction examined on cross sectional lung slides. As is typical of this model, there is wide variability between animals within all groups in the tumor fraction. These data should be considered in combination with other indicators of lung tumor burden in this model including lung to brain weight ratios and standard histopathology for final interpretation. It is important to note that morphometric analysis and histopathologic examination was performed on fixed lung tissue from the left lobe while other analyses on lung tissue may be performed on frozen tissue from the right lung lobes. Average tumor area is shown in FIG. 13 and FIG. 14.

Pathology Results

Figure 15:
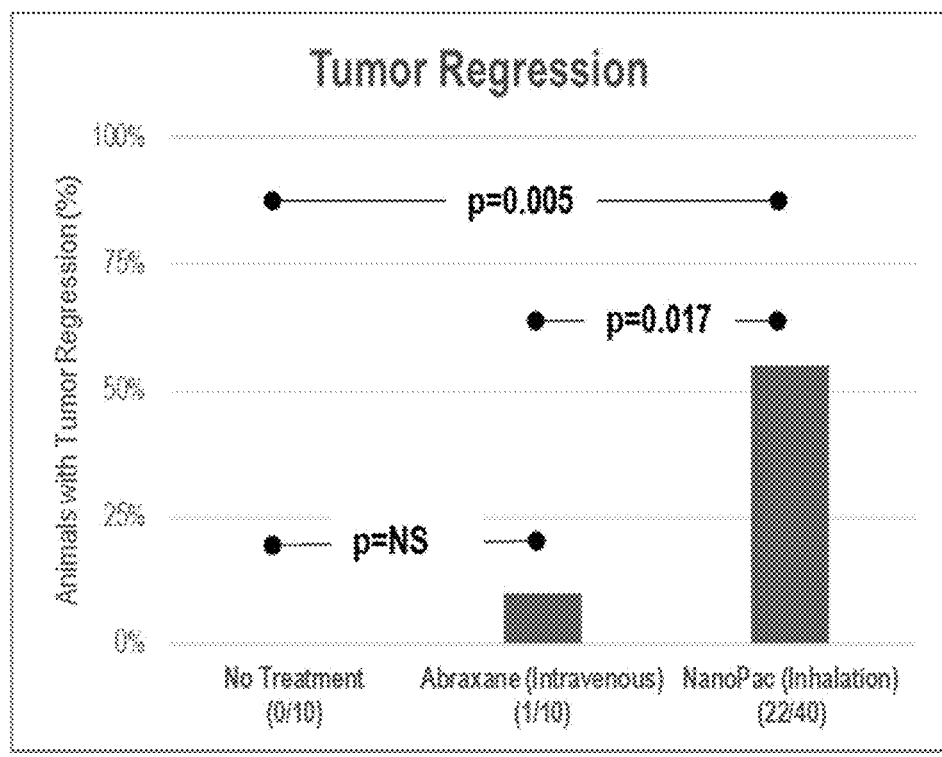
FIG. 15 is a plot of tumor regression from Orthotopic Lung Cancer study.

As a result of the slide examination of the identified populations of neoplastic cells the pathologist determined: (1) There was a slight decrease in severity of an overall lung tumor burden of Adenocarcinoma (undifferentiated and differentiated cells) in all treated groups (Grp. 2 (1.7), Grp. 3 (1.8), Grp. 4 (1.7), Grp 5 (1.6) and Grp. 6 (1.6) compared to the untreated Control Grp. 1 (2.1). (2) There was reduction in the Primitive Tumor Cell population evident by a decrease in the severity in Grp. 3 (0.3), Grp. 4 (0.3), Grp 5 (0.2) and Grp 6 (0.2) compared to the corresponding control Grp 1 (0.9) and Grp 2 (1.0), and 3) There was Tumor Regression present in Grp 3 (0.6), Grp 4 (1.0), Grp 5 (0.8) and Grp 6 (1.0) compared to the corresponding control Grp 1 (0.0) and Grp 2 (0.1). The incidence and severties of the lung burden characteristics data are summarized in Table 7, and in FIG. 15. Photomicrographs of the slides are shown in FIGS. 16 to 50.

TABLE 7

Incidences and Severities of Cumulative Lung Burden Table

| | Groups | | | | | |
|---|---|---|---|---|---|---|
| | 1 Control | 2 IV Abraxane | 3 Low 1x | 4 High 1x | 5 Low 2x | 6 High 2x |
| Animal Nos. | 1001-1010 | 2001-2010 | 3001-3010 | 4001-4010 | 5001-5010 | 6001-6010 |
| LUNG (NO. EX) | (10) | (10) | (10) | (10) | (10) | (10) |
| Adenocarcinoma | 10 | 10 | 10 | 9 | 10 | 10 |
| Minimal | 2[a] | 4 | 5 | 3 | 5 | 5 |
| Mild | 5 | 5 | 2 | 4 | 4 | 3 |
| Moderate | 3 | 1 | 3 | 2 | 1 | 2 |
| Marked | 0[b] | 0 | 0 | 0 | 0 | 0 |
| Average Severity Grade | 2.1 | 1.7 | 1.8 | 1.7 | 1.6 | 1.7 |
| Primitive Tumor Cells | 9 | 10 | 2 | 3 | 2 | 2 |
| Minimal | 9 | 10 | 1 | 3 | 2 | 2 |
| Mild | 0 | 0 | 1 | 0 | 0 | 0 |
| Moderate | 0 | 0 | 0 | 0 | 0 | 0 |
| Marked | 0 | 0 | 0 | 0 | 0 | 0 |
| Average Severity Grade | 0.9 | 1.0 | 0.3 | 0.3 | 0.2 | 0.2 |
| Tumor Regression | 0 | 1 | 6 | 5 | 6 | 5 |
| Minimal | 0 | 1 | 6 | 3 | 5 | 2 |
| Mild | 0 | 0 | 0 | 0 | 0 | 2 |
| Moderate | 0 | 0 | 0 | 1 | 1 | 0 |
| Marked | 0 | 0 | 0 | 1 | 0 | 1 |
| Average Severity Grade | 0 | 0.1 | 0.6 | 1.0 | 0.8 | 1.0 |

[a] Severity Grade based on a 4 point grading scale of 1 to 4: 1 = minimal, 2 = mild, 3 = moderate, 4 = marked
[b] The presence of a (0) indicates that there is no evidence histopathologically of the lesion in question Histological Overview of Photomicrographs in FIGS. 16 to 50

General Observations:

Control: Extensive levels of viable tumor with proliferating cells and little to no immune cell infiltration.

ABRAXANE® IV: Many viable appearing tumor masses with some lymphocytic response along with some tumor regression.

paclitaxel particle formulation 1x per week, High: Clearance of tumor from the lung with few viable tumor cells remaining. Masses remaining appear to be immune cell infiltrate and fibrosis.

paclitaxel particle formulation 2x per week, Low: Some remaining tumor nodules surrounded by immune cell infiltrate including macrophages and mononuclear cells.

paclitaxel particle formulation 2x per week, High: Few tumor nodules with immune infiltrate and stromal fibrosis replacing tumor.

Extensive mononuclear tumoricidal cell infiltration was observed in the lungs of animals receiving paclitaxel particle formulation through inhalation. As the model used is T cell deficient, it is likely that the cells are B cells or NK cells, or both. B cells are responsible for the production of antibodies and can be involved in tumor cell killing through antibody-dependent cell mediated cytotoxicity (the antibodies bind to cells expressing Fc Receptors and enhance the killing ability of these cells). NK cells are innate lymphoid cells that are crucial in the killing of tumor cells. In patients with tumors, NK cell activity is reduced allowing for the growth of the tumor. Along with T cells, NK cells are the target of some check point inhibitors to increase their activity.

By the use of a wide array of surface receptors capable of delivering either triggering or inhibitory signals, NK cells can monitor cells within their environment to ascertain if the cell is abnormal (tumor or virally infected) and should be eliminated through cytotoxicity.

The cytotoxicity and chemotaxis of NK cells can be modified by many pathological processes including tumor cells and their byproducts. In response to certain signals their functions are enhanced or potentiated. In response to several Pathogen Associated Molecular Patterns (PAMPs) by using different Toll Like Receptors (TLR); NK cells can increase cytokine production and/or cytolytic activity. Cytokines, including IL-2, IL-15, IL-12, IL-18, and IFNs α/β can also modify the activity of NK cells. NK cells are not simple cells that are only cytolytic effectors capable of killing different tumor cell targets; rather, they represent a heterogeneous population which can finely tune their activity in variable environmental contexts.

The tumor burden seems to be significantly reduced in the lungs of the animals treated with paclitaxel particle formulation and is lower than that for ABRAXANE® IV. Therefore, the localized administration of paclitaxel in the form of paclitaxel particle formulation provides additional potency. This is likely due to both the longer exposure to the chemotherapy over time and the vigorous cellular infiltration to the site of the tumor. This latter response appeared to be dependent on the dose density (actual dose and dose frequency).

Figure 16:
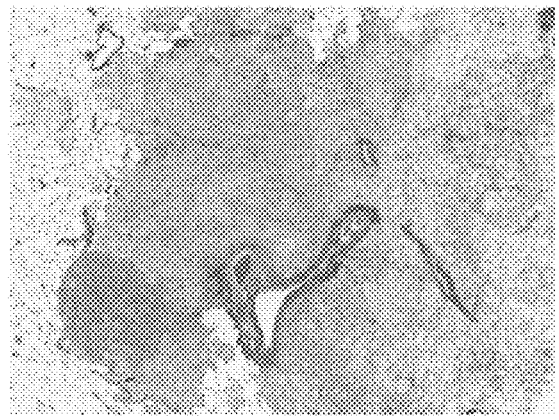
FIG. 16 is a photomicrograph of Orthotopic Lung Cancer tissue slide—1006 (Control) Adenocarcinoma-3, Primitive-1, Regression-0. Primary characteristics of the lung tumor masses. (2×).
Figure 17:
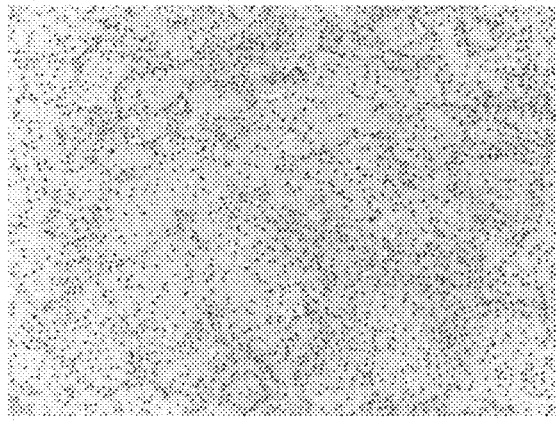
FIG. 17 is a photomicrograph of Orthotopic Lung Cancer tissue slide—1006 Control, Adenocarcinoma-3, Primitive-1, Regression-0. Primary characteristics of undifferentiated cells within the lung tumor masses.
Figure 18:
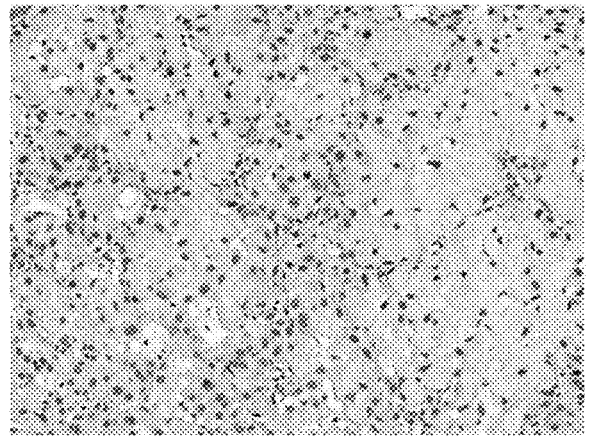
FIG. 18 is a photomicrograph of Orthotopic Lung Cancer tissue slide—1006 (Control) Adenocarcinoma-3, Primitive-1, Regression-0. Primary characteristics of undifferentiated cells within the lung tumor masses.
Figure 19:
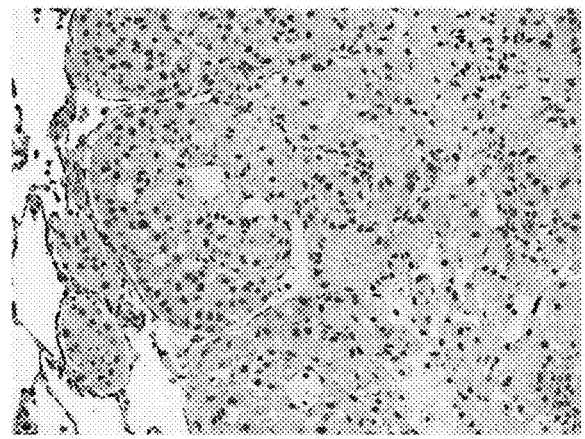
FIG. 19 is a photomicrograph of Orthotopic Lung Cancer tissue slide—1006 (Control) Adenocarcinoma-3, Primitive-1, Regression-0. Primary characteristics of undifferentiated cells within the lung tumor masses showing masses within alveolar spaces. a(20×).
Figure 20:
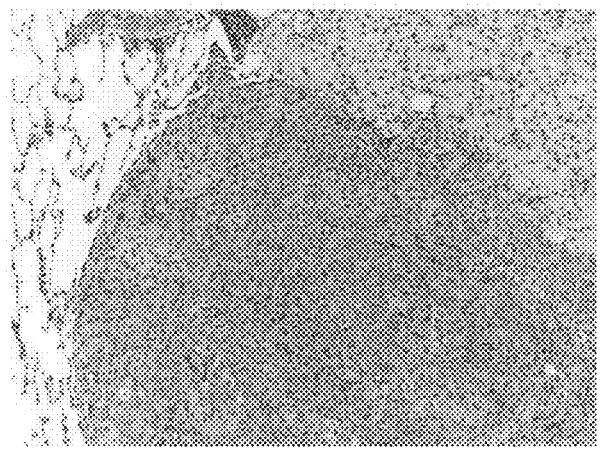
FIG. 20 is a photomicrograph of Orthotopic Lung Cancer tissue slide—1006 (Control) Adenocarcinoma-3, Primitive-1, Regression-0. Primary characteristics of primitive cells within the lung tumor masses. b(10×).
Figure 21:
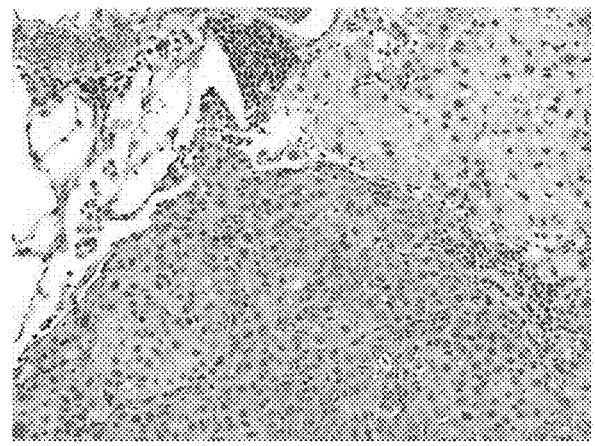
FIG. 21 is a photomicrograph of Orthotopic Lung Cancer tissue slide—1006 (Control) Adenocarcinoma-3, Primitive-1, Regression-0. Primary characteristics of primitive cells within the lung tumor masses. b20×.
Figure 22:
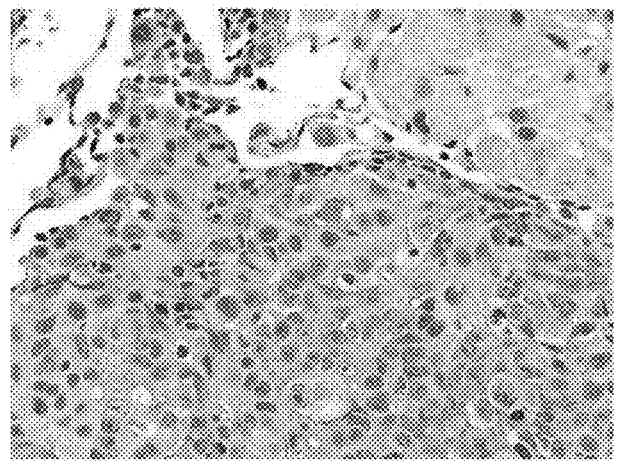
FIG. 22 is a photomicrograph of Orthotopic Lung Cancer tissue slide—1006 (Control) Adenocarcinoma-3, Primitive-1, Regression-0. Primary characteristics of primitive cells within the lung tumor masses. b(40×).
Figure 23:
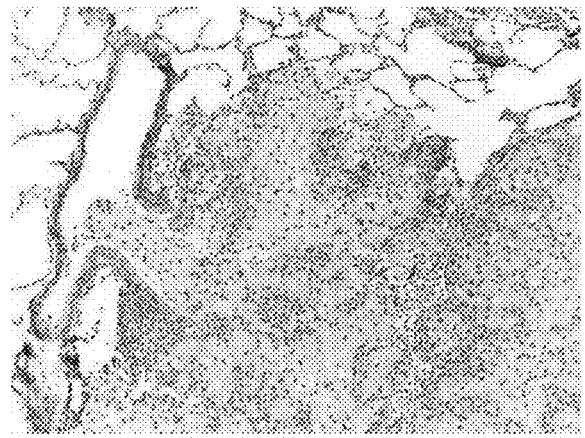
FIG. 23 is a photomicrograph of Orthotopic Lung Cancer tissue slide—1006 (Control) Adenocarcinoma-3, Primitive-1, Regression-0. Primary characteristics of primitive cells within the lung tumor masses. b(40×).
Figure 24:
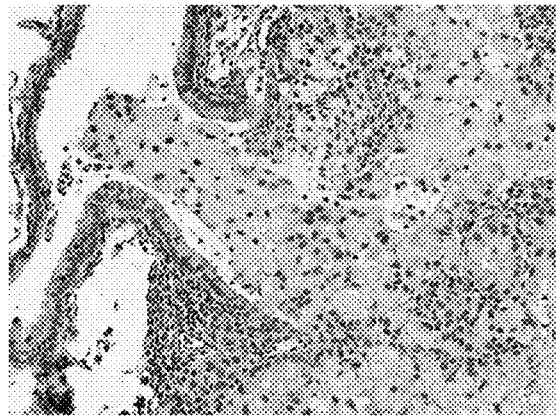
FIG. 24 is a photomicrograph of Orthotopic Lung Cancer tissue slide—1006 (Control) Adenocarcinoma-3, Primitive-1, Regression-0 bronchiole. Primary characteristics of undifferentiated cells showing within bronchiole. c(20×).
Figure 25:
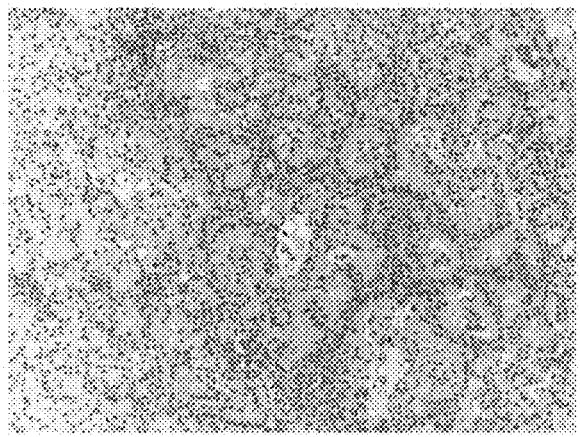
FIG. 25 is a photomicrograph of Orthotopic Lung Cancer tissue slide—1006 (Control) Adenocarcinoma-3, Primitive-1, Regression-0 glands. Primary characteristics of acinar gland differentiation within the lung tumor masses. d(10×).
Figure 26:
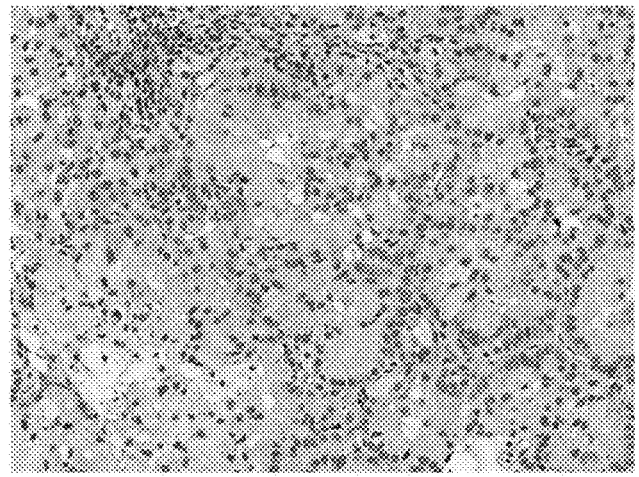
FIG. 26 is a photomicrograph of Orthotopic Lung Cancer tissue slide—1006 (Control) Adenocarcinoma-3, Primitive-1, Regression-0 glands. Primary characteristics of acinar gland differentiation within the lung tumor masses. d(20×).
Figure 27:
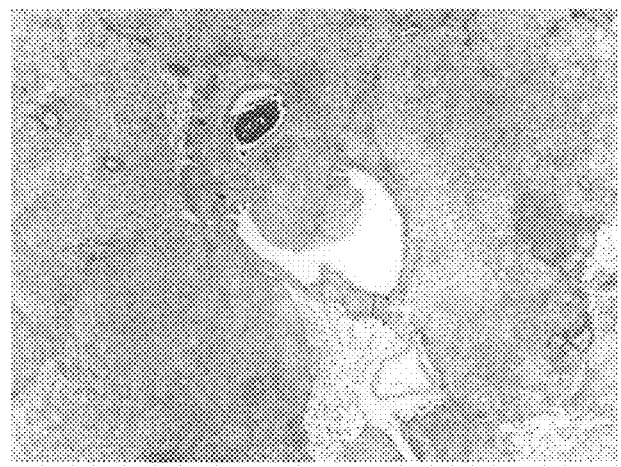
FIG. 27 is a photomicrograph of Orthotopic Lung Cancer tissue slide—2001 (IV ABRAXANE®) Adenocarcinoma-2, Primitive-1, Regression-O. Primary characteristics of the lung tumor mass pushing underneath a bronchiole and showing no evidence of intravascular invasion. (2×).
Figure 28:
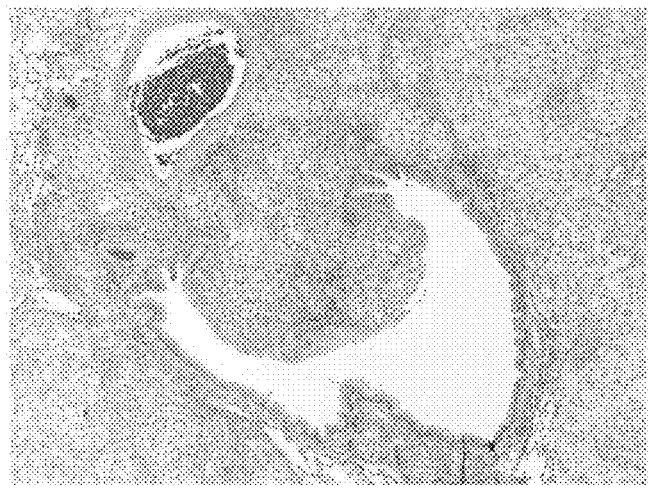
FIG. 28 is a photomicrograph of Orthotopic Lung Cancer tissue slide—2001 (IV ABRAXANE®) Adenocarcinoma-2, Primitive-1, Regression-0. Primary characteristics of the lung tumor mass pushing underneath a bronchiole and showing no evidence of intravascular invasion. (4×).
Figure 29:
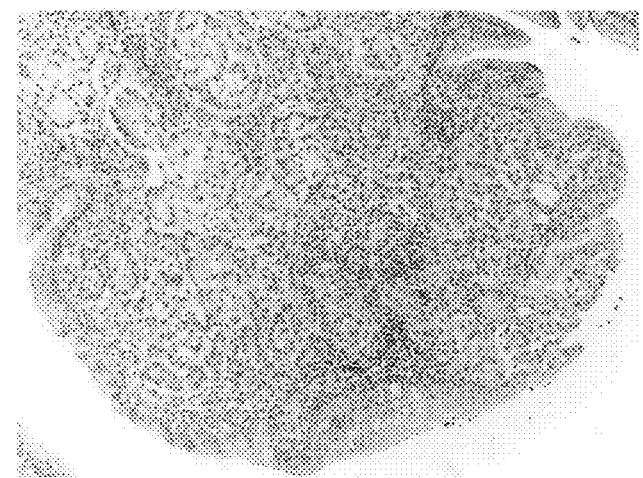
FIG. 29 is a photomicrograph of Orthotopic Lung Cancer tissue slide—2001 (IV ABRAXANE®) Adenocarcinoma-2, Primitive-1, Regression-0. Primary characteristics of the lung tumor mass pushing underneath a bronchiole. (10×).

Observations of Specific Photomicrographs:

FIG. 16: Subject 1006 (Control) Adenocarcinoma-3, Primitive-1, Regression-0. Low-power magnification (2×) showing the general distribution of undifferentiated, pleomorphic, large, anaplastic tumor cells within alveolar spaces or lining the alveolar septae. The majority of cells do not have features of adenocarcinoma and appear in sheets of contiguous tumor. Many cells have basophilic staining cytoplasm, while others are large, anaplastic and contain pale amphophilic-staining. Note the presence of a pre-existing resident population of alveolar macrophages and the absence of tumor regression.

Figure 30:
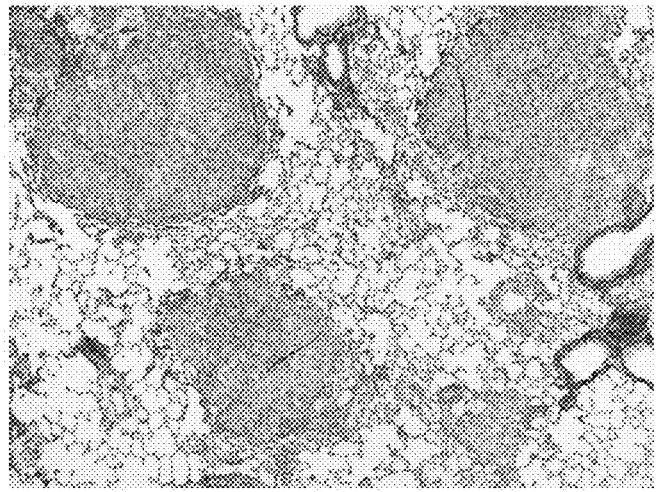
FIG. 30 is a photomicrograph of Orthotopic Lung Cancer tissue slide—2003 (IV ABRAXANE®) Adenocarcinoma-1, Primitive-1, Regression-1. Characteristics of the lung tumor masses undergoing regression. (4×).
Figure 31:
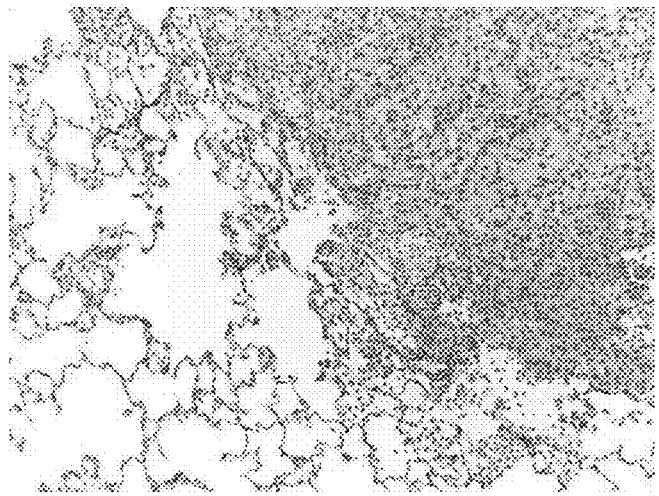
FIG. 31 is a photomicrograph of Orthotopic Lung Cancer tissue slide—2003 (IV ABRAXANE®) Adenocarcinoma-1, Primitive-1, Regression-1. Characteristics of the lung tumor masses undergoing regression. (10×).
Figure 32:
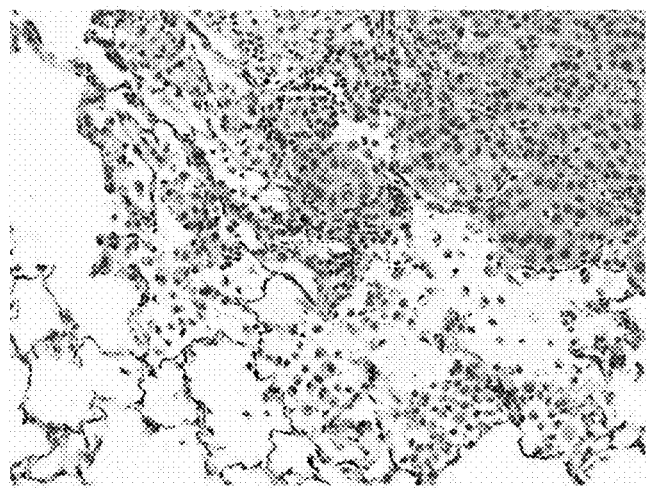
FIG. 32 is a photomicrograph of Orthotopic Lung Cancer tissue slide—2003 (IV ABRAXANE®) Adenocarcinoma-1, Primitive-1, Regression-1. Characteristics of the lung tumor masses undergoing regression. (20×).
Figure 33:
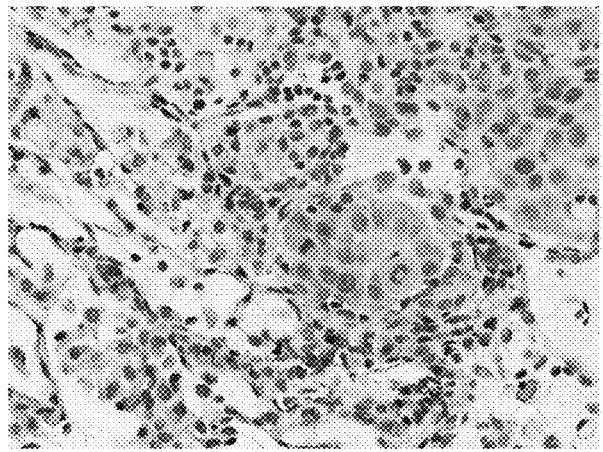
FIG. 33 is a photomicrograph of Orthotopic Lung Cancer tissue slide—2003 (IV ABRAXANE®) Adenocarcinoma-1, Primitive-1, Regression-1. Characteristics of the lung tumor masses undergoing regression. Note lymphocytes and macrophages along the edge. 1(40×).
Figure 34:
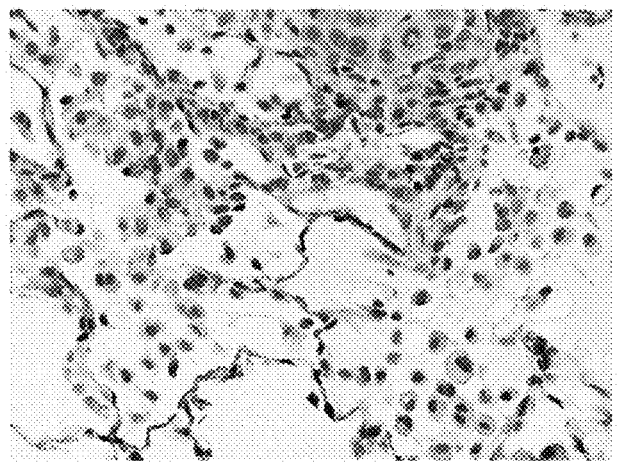
FIG. 34 is a photomicrograph of Orthotopic Lung Cancer tissue slide—2003 (IV ABRAXANE®) Adenocarcinoma-1, Primitive-1, Regression-1. Characteristics of the lung tumor masses undergoing regression. Note lymphocytes and macrophages along the edge. 2(40×).
Figure 35:
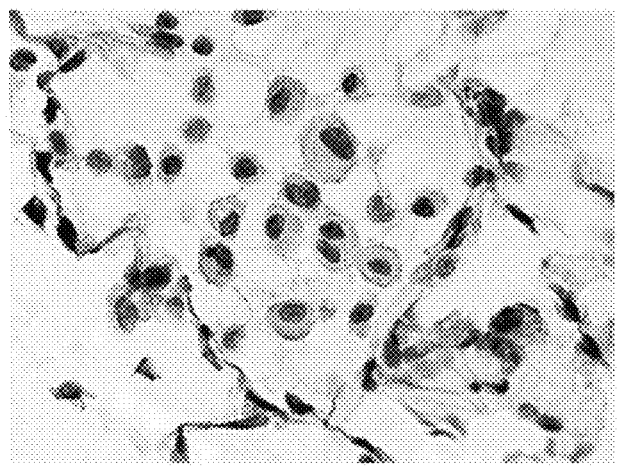
FIG. 35 is a photomicrograph of Orthotopic Lung Cancer tissue slide—2003 (IV ABRAXANE®) Adenocarcinoma-1, Primitive-1, Regression-1. Characteristics of the lung tumor masses undergoing regression. Note larger foamy and pigmented macrophages. 2, 2×(40×).

FIG. 30: Subject 2003 (IV ABRAXANE®) Adenocarcinoma-1, Primitive-1, Regression-1. Low-power magnification (4×) showing the general distribution of tumor masses predominantly at the periphery as well as multiple smaller expansive tumor masses filling alveolar spaces. The tumor cells are pleomorphic, large, anaplastic and have pale amphophilic-staining, varying from undifferentiated to differentiated patterns of adenocarcinoma. Evidence of tumor regression is present around the periphery of the mass and primarily characterized by the infiltration of macrophages.

Figure 36:
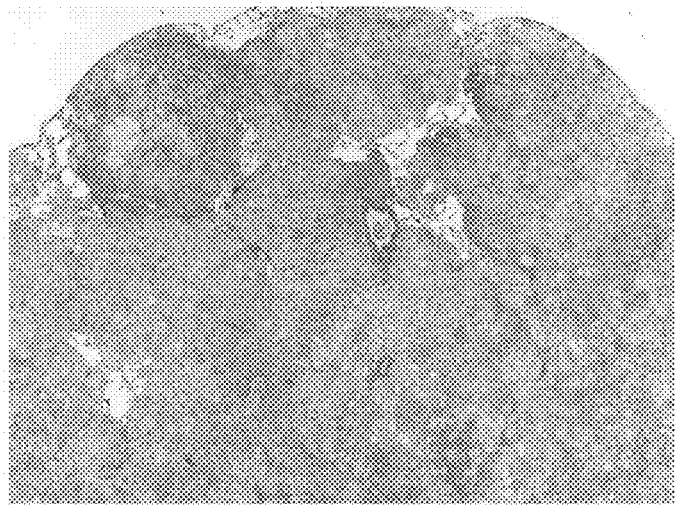
FIG. 36 is a photomicrograph of Orthotopic Lung Cancer tissue slide—2010 (IV ABRAXANE®) Adenocarcinoma-3, Primitive-1, Regression-0. Primary characteristics of the lung tumor masses. (2×).
Figure 37:
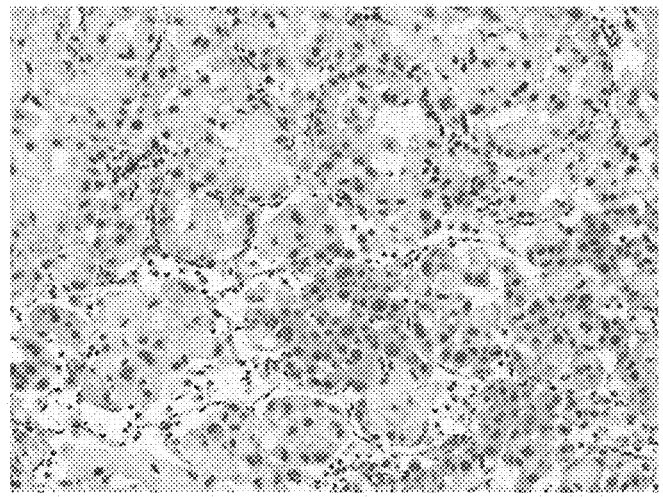
FIG. 37 is a photomicrograph of Orthotopic Lung Cancer tissue slide—2010 (IV ABRAXANE®) Adenocarcinoma-3, Primitive-1, Regression-0. Primary characteristics of the lung tumor masses. (20×).
Figure 38:
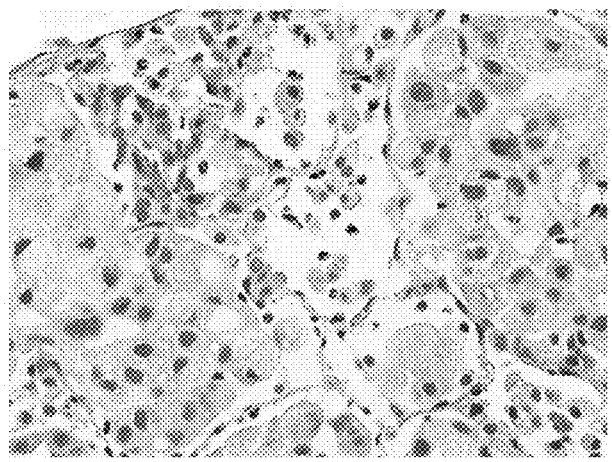
FIG. 38 is a photomicrograph of Orthotopic Lung Cancer tissue slide—2010 (IV ABRAXANE®) Adenocarcinoma-3, Primitive-1, Regression-0. Primary characteristics of the lung tumor masses. Note subtle evidence of macrophages along the edge. (40×).

FIG. 36: Subject 2010 (IV ABRAXANE®) Adenocarcinoma-3, Primitive-1, Regression-0. Low-power magnification (2×) showing the general distribution of large expansive tumor mass filling most alveolar spaces as well as neoplastic cells in the periphery. Most tumor cells are predominantly undifferentiated, pleomorphic, large, anaplastic with pale amphophilic-staining. The primitive cells are smaller, ovoid, and have more basophilic staining cytoplasm with variable, vesicular nuclei and moderate to marked anisokaryosis. Inflammatory cell infiltration are predominantly neutrophils and macrophages. This image demonstrates an absence of tumor regression.

Figure 39:
FIG. 39 is a photomicrograph of Orthotopic Lung Cancer tissue slide—4009 (IH paclitaxel particle formulation 1× High) Adenocarcinoma-0, Primitive-0, Regression-4. Characteristics of the lung tumor masses that have undergone complete regression. (2×).

FIG. 39: Subject 4009 (IH paclitaxel particle formulation 1×/wk High) Adenocarcinoma-0, Primitive-0, Regression-4. Low-power magnification (2×) showing the general distribution of previously populated tumor masses, the presence of multiple small areas of fibrous connective tissue, central collagenous stroma and fibrocytes are seen at the peripheral alveolar spaces as well as thickened alveolar septae supports evidence of tumor regression. In addition, the alveolar spaces are commonly filled with infiltrate of macrophages and lymphocytes together with additional evidence of tumor regression.

Figure 42:
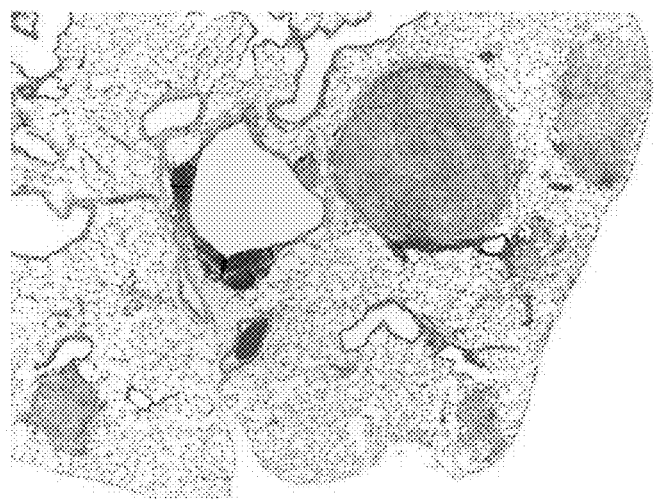
FIG. 42 is a photomicrograph of Orthotopic Lung Cancer tissue slide—5010 (IH paclitaxel particle formulation 2× Low) Adenocarcinoma-1, Primitive-0, Regression-3. Characteristics of the lung tumor masses undergoing regression. (2×).
Figure 43:
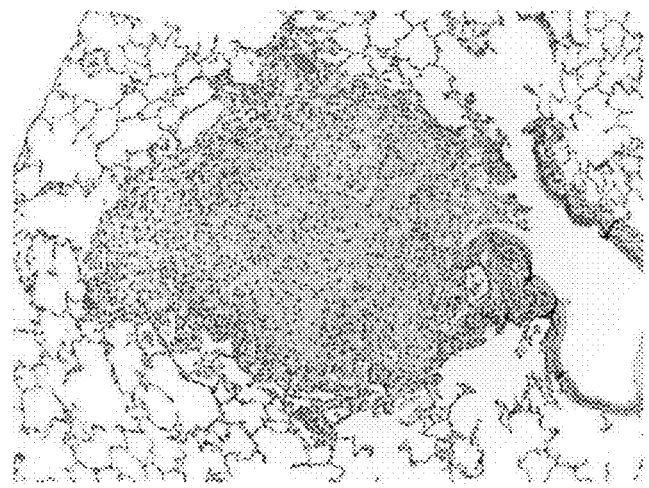
FIG. 43 is a photomicrograph of Orthotopic Lung Cancer tissue slide—5010 (IH paclitaxel particle formulation 2× Low) Adenocarcinoma-1, Primitive-0, Regression-3. Characteristics a lung tumor mass that is undergoing regression. (10×).
Figure 44:
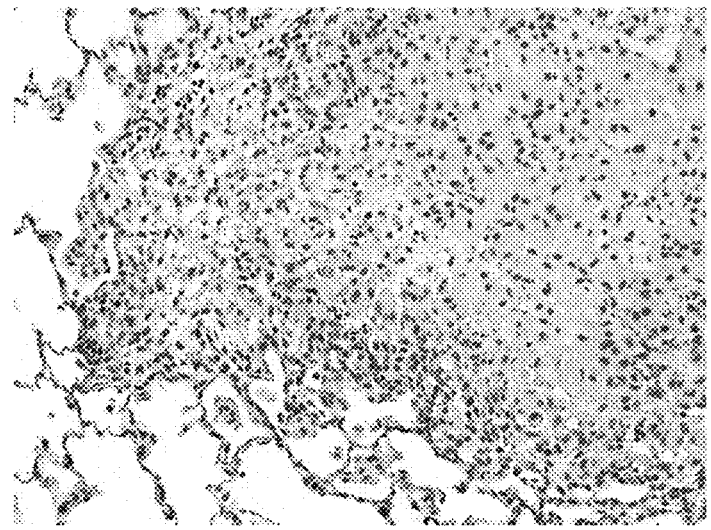
FIG. 44 is a photomicrograph of Orthotopic Lung Cancer tissue slide—5010 (IH paclitaxel particle formulation 2× Low) Adenocarcinoma-1, Primitive-0, Regression-3. Characteristics a lung tumor mass that is undergoing regression. (20×).
Figure 45:
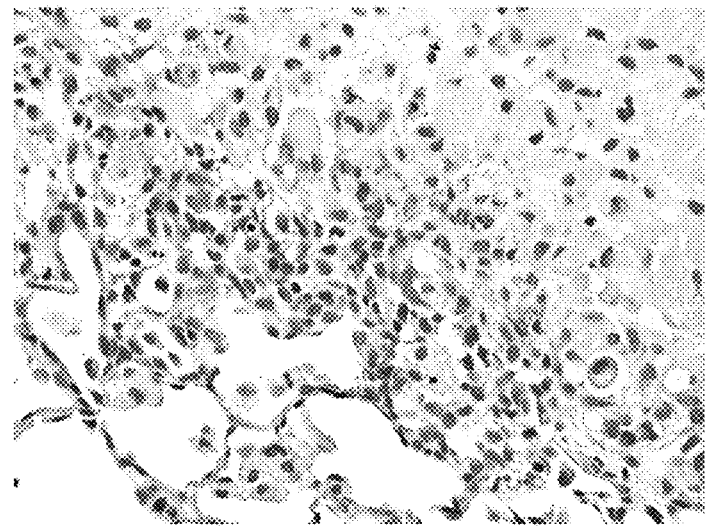
FIG. 45 is a photomicrograph of Orthotopic Lung Cancer tissue slide—5010 (IH paclitaxel particle formulation 2× Low) Adenocarcinoma-1, Primitive-0, Regression-3. Characteristics a lung tumor mass that is undergoing regression. (40×).

FIG. 42: Subject 5010 (IH paclitaxel particle formulation 2×/wk Low) Adenocarcinoma-1, Primitive-0, Regression-3. Low-power magnification (2×) showing the general distribution of previously populated tumor masses. Regressing masses are variably small and randomly distributed. Fibrous connective tissue is seen filling/replacing alveolar spaces and suggests foci of regressing adenocarcinoma. Acute necrosis, fibrous connective scaffolding, mixed cell infiltration of macrophages, giant cells and lymphocytes in the epithelium as well as around the stroma are signs of tumor regression.

Figure 46:
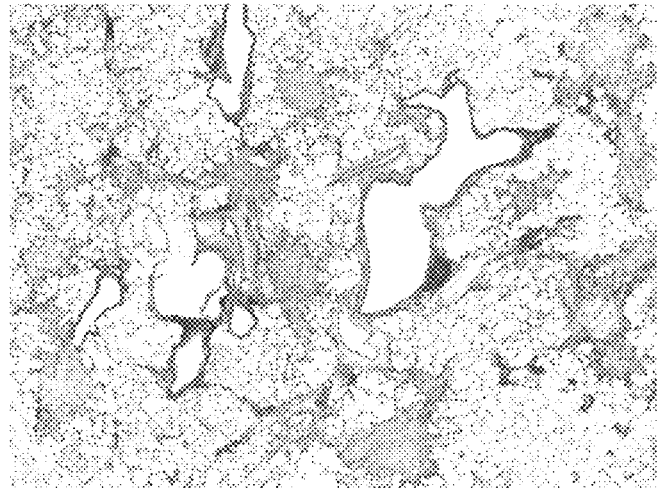
FIG. 46 is a photomicrograph of Orthotopic Lung Cancer tissue slide—6005 (IH paclitaxel particle formulation 2× High) Adenocarcinoma-1, Primitive-0, Regression-4. Characteristics a lung tumor mass that is undergoing regression. (2×).
Figure 47:
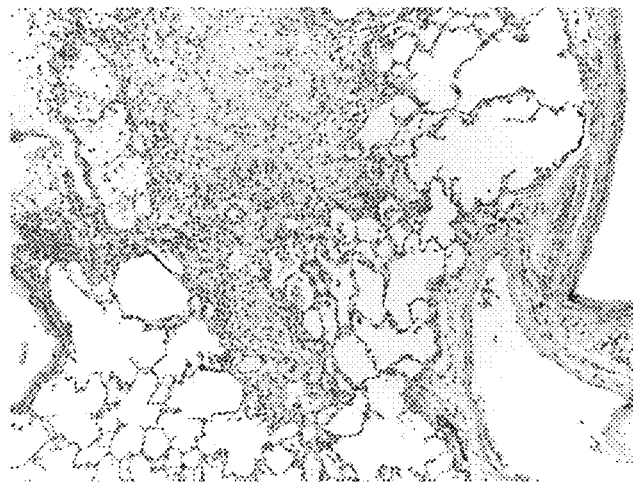
FIG. 47 is a photomicrograph of Orthotopic Lung Cancer tissue slide—6005 (IH paclitaxel particle formulation 2× High) Adenocarcinoma-1, Primitive-0, Regression-4. Characteristics a lung tumor mass that is undergoing regression. Note stromal fibrosis, and lymphocytes and macrophages along the edge. (10×).
Figure 48:
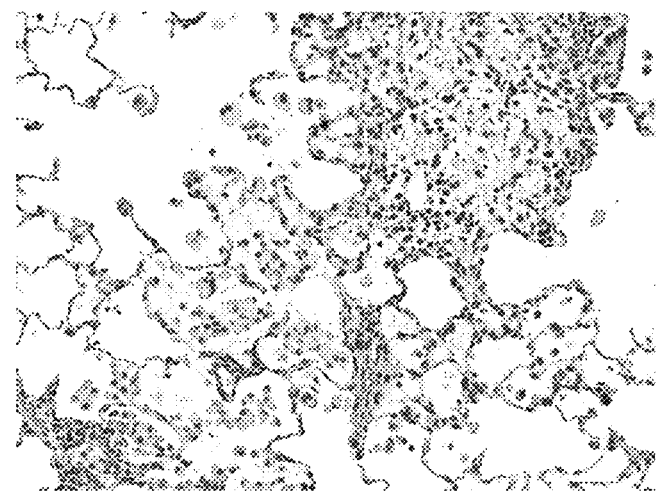
FIG. 48 is a photomicrograph of Orthotopic Lung Cancer tissue slide—6005 (IH paclitaxel particle formulation 2× High) Adenocarcinoma-1, Primitive-0, Regression-4. Characteristics a lung tumor mass that is undergoing regression. Note lymphocytes and macrophages along the edge. (20×).
Figure 49:
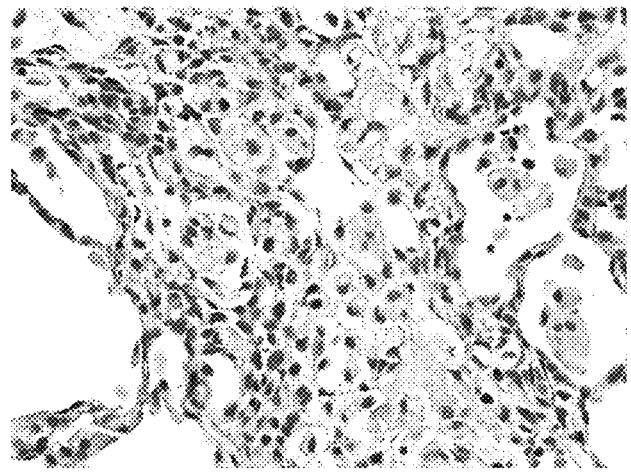
FIG. 49 is a photomicrograph of Orthotopic Lung Cancer tissue slide—6005 (IH paclitaxel particle formulation 2× High) Adenocarcinoma-1, Primitive-0, Regression-4. Note lymphocytes and macrophages along the edge. (40×).
Figure 50:
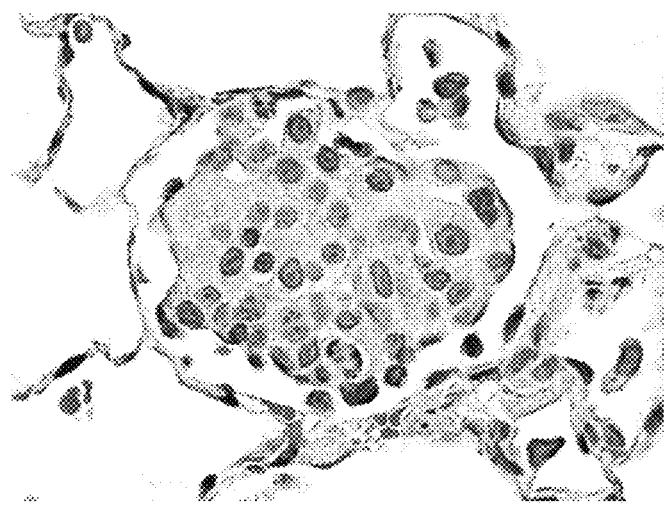
FIG. 50 is a photomicrograph of Orthotopic Lung Cancer tissue slide—6005 (IH paclitaxel particle formulation 2× High) Adenocarcinoma-1, Primitive-0, Regression-4. Note the presence of a focal area of residual tumor cells within an alveolus. 2(40×).

FIG. 46: Subject 6005 (IH paclitaxel particle formulation 2×/wk High) Adenocarcinoma-1, Primitive-0, Regression-4. Low-power magnification (2×) showing the general distribution of previously populated tumor masses in multiple small areas of fibrous connective tissue filling/replacing the alveolar spaces suggesting foci of previous infiltrates of adenocarcinoma cells. Tumor regression is evidenced by fibrosis of previously populated tumor masses, central collagenous stromal core and fibrous connective tissue at the periphery filling/replacing the alveolar spaces, thickening of the septae as well as the presence of fibrocytes filling the alveolar space infiltrated by lymphocytes and macrophages.

Conclusions

One hundred twenty-seven (127) NIH-rnu Nude Rats were x-irradiated to induce immunosuppression on Day −1. On Day 0 animals were dosed with Calu3 tumor cells by intratracheal (IT) instillation. Animals underwent a growth period of three weeks. During the third week, animals were randomized by body weight stratification into the groups. Starting Week 4, animals in Group 2 received a once weekly dose of ABRAXANE® by intravenous (IV) dosing (5 mg/kg) on Days 22, 29 and 36. Animals in Groups 3 and 4 received once weekly (Monday) inhalation (INH) dose of paclitaxel particle formulation at low (0.5 mg/kg) and high (1.0 mg/kg) target doses, respectively. Animals in Groups 5 and 6 received a twice weekly (Monday and Thursday) target inhalation dose of paclitaxel particle formulation at low (0.50 mg/kg) and high (1.0 mg/kg) doses respectively. Animals in Group 1 were left untreated as a control of normal tumor cell growth. All animals were necropsied during Week 8.

All animals survived to their designated necropsy timepoint. Clinical observations related to the model included skin rash, labored breathing. All groups gained weight at about the same rate through the course of the study.

The inhalation exposure average Paclitaxel aerosol concentration for once weekly Low Dose and twice weekly Low Dose paclitaxel particle formulation groups was 270.51 µg/L and 263.56 µg/L, respectively. The inhalation exposure average Paclitaxel aerosol concentration for once weekly High Dose and twice weekly High Dose paclitaxel particle formulation groups was 244.82 µg/L and 245.76 µg/L, respectively.

Doses were based on average aerosol paclitaxel concentration, most recent average group bodyweight, assumed deposition fraction of 10% and exposure duration of 33 or 65 minutes. During four weeks of treatment, the average achieved rodent deposited dose for the once weekly Low Dose paclitaxel particle formulation group and twice weekly Low Dose paclitaxel particle formulation group were 0.655 mg/kg and 0.640 mg/kg (1.28 mg/kg/week), respectively. The average achieved rodent deposited dose for the once weekly High Dose paclitaxel particle formulation group and twice weekly High Dose paclitaxel particle formulation group were 1.166 mg/kg and 1.176 mg/kg (2.352 mg/kg/week), respectively. For the group receiving IV injections of ABRAXANE®, the average dose on Day 22, 29 and 36 was 4.94, 4.64 and 4.46 mg/kg respectively.

At scheduled necropsy, the majority of animals from each group had tan nodules on the lungs and/or red or tan patchy discolorations of the lung. Other sporadic observations included an abdominal hernia in one animal and nodule on the pericardium of another animal. No other abnormal gross observations were noted at necropsy.

In ABRAXANE® treated animals, lung weights, lung to BW ratios and lung to brain weight ratios were significantly lower compared to Untreated Controls. The once weekly paclitaxel particle formulation High Dose group had similar weights to the ABRAXANE® group and significantly lower lung weights and lung to brain ratios compared to Untreated Controls.

Compared to the positive control Grp. 1 and the ABRAXANE® treated comparative Grp. 2, there was a therapeutic effect as measured by lower lung/brain weight ratio and lower overall lung tumor burden without apparent adverse events. Histological analysis of lung tumor burden treated with inhaled paclitaxel particle formulation showed a decrease in tumor mass, a decrease in primitive tumor cell population, and an increase in tumor regression. Extensive mononuclear cell infiltration was observed in the lungs of animals receiving paclitaxel particle formulation through inhalation. As the model used is T cell deficient, it is likely that the cells are B cells or NK cells. It is hypothesized that the localized, likely higher concentration exposure of the tumor to paclitaxel particles affected the tumors leading to an alteration in the environment to draw the mononuclear cellular infiltrate into the lung.

Example 4: Study FY 17-008B—Paclitaxel Particle Pharmacokinetic Study

Executive Summary

Ninety (90) male Sprague Dawley rats were exposed to "clinical reference" dose of paclitaxel, ABRAXANE® (paclitaxel protein bound particles for injectable suspension, aka nab-paclitaxel), by intravenous (IV) bolus injection or paclitaxel particle formulation (target dose of 0.37 or 1.0 mg/kg) by nose only inhalation on a single occasion. Three animals (n=3) were euthanatized at ten (10) timepoints from 0.5 to 336 hours post exposure for blood (plasma) and lung tissue collections. Non-compartmental analysis (NCA) was performed on plasma and lung tissue to identify the duration of detectable amounts of paclitaxel post exposure for each dose group. Animals designated to the 336 hour time point from all groups had right lungs collected for liquid chromatography-mass spectrometry (LCMS) analysis while the left lungs were perfused with 10% neutral buffered formalin (NBF) and retained for potential histopathology. In order to enable comparative histopathology, three spare animals (Naive Controls) were euthanized at the 336 hour timepoint and lung collections were performed in the same manner. Animals designated to all other timepoints had all lungs individually frozen for LCMS analysis.

The inhalation exposure average Paclitaxel aerosol concentration for Low Dose and High Dose paclitaxel particle formulation groups was of 85.64 µg/L and 262.27 µg/L, respectively. The average exposure aerosol concentration was within ±15% of target aerosol concentration which was expected for nebulized inhalation exposures. The particle size distribution was determined in terms of MMAD (GSD) for each paclitaxel particle formulation aerosols using a cascade impactor. For 6.0 mg/mL and 20.0 mg/mL paclitaxel particle formulation aerosols the MMAD (GSD) were determined to be 1.8 (2.0) µm and 2.3 (1.9) µm, respectively.

Paclitaxel deposited low-dose was calculated based on Paclitaxel average aerosol concentration of 85.64 µg/L, average Day 0 group bodyweight of 420.4 g, assumed deposition fraction of 10% and exposure duration of 65 minutes; the average achieved rodent deposited dose was determined to be 0.38 mg/kg for the Low Dose paclitaxel particle formulation group. For the High Dose paclitaxel particle formulation group, paclitaxel average aerosol concentration of 262.27 µg/L, average Day 0 group bodyweight of 420.5 g, assumed deposition fraction of 10% and exposure duration of 65 minutes; the average achieved rodent deposited dose was determined to be 1.18 mg/kg. The recorded oxygen and temperature ranges were 19.8%-20.9% and 20.7° C.-20.8° C., respectively for 6.0 mg/mL paclitaxel particle formulation exposure. For 20.0 mg/mL paclitaxel particle formulation exposure, the recorded oxygen value was 19.8% throughout the exposure and temperature range was 20.7° C.-20.8° C.

For the group receiving IV injections of ABRAXANE®, Day 1 bodyweights ranged from 386.1 to 472.8 g, this resulted in ABRAXANE® doses of 2.6-3.2 mg/kg, with the average group dose being 2.9 mg/kg.

All groups gained weight through the course of the study. No abnormal clinical observations were noted through the duration of the study. All animals survived to their designated necropsy timepoint. All animals were euthanized within the window intended for each time point.

At necropsy, approximately half of the animals from each group had minimal to mild, tan discolorations on the lungs. Such observations are often associated with inhalation exposures. Other transient observations included an enlarged heart (animal #2016) and enlarged tracheobronchial lymph nodes. No other abnormal gross observations were noted at necropsy. Histopathology showed lung and trachea from test and reference article treated rats were within normal limits and indistinguishable from those of na'ive rats under the conditions of this study. At the 336 hour post-dosing sacrifice, macrophage accumulation which is common in inhalation studies as a physiologically normal response to exogenous material deposited in the lung was not apparent within the lung sections of treatment animals examined for this study.

The NCA was designed to quantify the exposure (area under the concentration versus time curve [AUC]), time to maximum concentration ($T_{max}$), maximum concentration ($C_{max}$) and when possible apparent terminal half-life ($T_{1/2}$).

The hypothesis for the novel paclitaxel particle formulation was that the formulation would result in increased retention of paclitaxel within the lung tissue and reduce the systemic exposure. The half-life within systemic plasma was unchanged for the formulation/doses tested and the half-life within the lung tissue was increased with the paclitaxel particle formulation delivered by inhalation. The exposure to the lung tissue (dose normalized AUC) was increased when delivered as the paclitaxel particle formulation by inhalation.

Collectively the data indicate a significant retention of paclitaxel particles within the lung tissue when delivered via inhalation compared to the IV "clinical reference".

Objectives

The objective of this study was to determine the pharmacokinetics of the paclitaxel particle formulation compared to a clinical reference dose of paclitaxel. The pilot pharmacokinetic (PK) data from Lovelace Biomedical study FY 17-008A (Example 1 above) with paclitaxel particle formulation dosed by inhalation indicated a retention time beyond 168 hours in lung tissue. In this study, animals dosed with either a single low or high dose nose-only inhalation paclitaxel particle formulation or single clinical reference dose of paclitaxel via intravenous (IV) tail injection had plasma and lung tissue evaluated at timepoints from 0.5 to 336 hours.

Materials and Methods

Test System

Species/Strain: Sprague Dawley Rats
Age of Animals at Study Start: 8-10 weeks of age
Body Weight Range at Study Start: 345-447 g Number on Study/Sex: 95 Males (90 study animals and 5 spares)
Source: Charles River Laboratories (Kingston, N.Y.)
Identification: Permanent maker tail marking
ABRAXANE® Formulation The clinical reference material used IV formulation was the drug product ABRAXANE® (Manufacturer: Celgene Corporation, Summit, N.J.; Lot: 6111880). The drug product was reconstituted to 5.0 mg/mL with saline (Manufacturer: Baxter Healthcare, Deerfield, 11.; Lot: P357889) on the day of dosing and was stored per manufacturer's instructions.

Paclitaxel Particle Formulation

The 6.0 mg/ml paclitaxel particle formulation for Low Dose group exposures and 20.0 mg/ml paclitaxel particle formulation for High Dose group exposures were prepared per the sponsor recommendations. Specifically, the paclitaxel particles were reconstituted with 1% polysorbate 80. The vial was shaken by hand until all particles were wetted. Additional 0.9% sodium chloride for injection was added (to the desired concentration target) and the vial was shaken by hand for another minute.

Shaking continued until no large clumps were visible and the suspension was properly dispersed. Resultant formulations were left undisturbed for at least 5 minutes to reduce any air/foam in the vial before placing it in a nebulizer for aerosolization work. The final formulation of 6.0 mg/mL was kept at room temperature and nebulized within 2 hours after reconstitution. The final formulation of 20.0 mg/mL was kept at room temperature and nebulized within 30 minutes after reconstitution.

Experimental Design

Animals in Group 1 shown in Table 8 received a single "clinical reference" dose (formulation concentration: 5 mg/mL, target dose: 5.0 mg/kg based on bodyweight; target dose volume: not to exceed 250 μL) of ABRAXANE® (paclitaxel protein bound particles for injectable suspension) by IV tail vein injection. Animals in Group 2 and 3 in Table 9 were exposed to paclitaxel particle formulation aerosols (target dose of 0.37 or 1.0 mg/kg) by nose only inhalation (INH) on a single occasion per the study design below. Three animals (n=3) were euthanized at 0.5 (±10 minutes), 6 (±10 minutes), 12 (±10 minutes), 24 (±30 minutes), 48 (±30 minutes), 72 (±30 minutes), 120 (±30 minutes), 168 (±30 minutes) 240 (±30 minutes) and 336 (±30 minutes) hours post exposure for blood (plasma) and lung tissue collections. Non-compartmental analyses were performed on plasma and lung tissue to identify duration of detectable amounts of paclitaxel post exposure for each dose group. Animals designated to the 336 hour time point from all groups had right lungs individually frozen for LCMS analysis while the left lungs were perfused with 10% neutral buffered formalin (NBF) and retained for potential histopathology. In order to enable comparative histopathology, three spare animals (Naive Controls) were also be euthanized alongside the 336 hour timepoint and had have lung collections performed in the same manner.

TABLE 8

Experimental Design

| Group | N = | Target Dose | Route | Target Exposure Duration | PK timepoints (hours post exposure) |
|---|---|---|---|---|---|
| 1 ABRAXANE ® "Clinical Reference" Dose | 30 | Up to 5.0 mg/kg[B] | IV | n/a | N = 3 from each group at 0.5, 6, 12, 24, 48, 72, 120, 168, 240 and 336[A] hours post exposure |
| 2 paclitaxel particle formulation Low Dose | 30 | 0.37 mg/kg | INH | up to 65 min | |
| 3 paclitaxel particle formulation High Dose | 30 | 1.0 mg/kg | INH | up to 65 min | |

[A]Study animals from each group and three spares will have tissue collections for LCMS analysis as well as potential histopathology at 336 hours post exposure.
[B]ABRAXANE ® (concentration: 5 mg/ml, target dose: up to 5.0 mg/kg based on bodyweight with dose volume not to exceed 250 μL) was administered to animals in Group I by IV tail vein injection Husbandry, Quarantine and Assignment to Study Male Sprague Dawley rats (6-8 weeks old) were obtained from Charles River Laboratories (Kingston, N.Y.) and quarantined for 14 days. At the end of quarantine, animals were weighed and then randomized by weight for assignment to study. Animals were identified by tail marking and cage card. Water, lighting, humidity, and temperature control were maintained and monitored according to appropriate SOPs. Rats were fed a standard rodent diet ad libitum during non-exposure hours.

Body Weights and Daily Observations

Body weights were collected at randomization, daily throughout the study and at euthanasia. Each animal on study was observed twice daily by Comparative Medicine Animal Resources (CMAR) personnel for any clinical signs of abnormality, moribundity or death.

ABRAXANE® Administration IV—Tail Vein Injections

ABRAXANE® (concentration: 5 mg/mL, target dose: 5.0 mg/kg based on bodyweight; dose volume: not to exceed 250 μL) was administered to animals in Group 1 by IV tail vein injection on a single occasion.

Paclitaxel Particle Administration—Nose-Only Aerosol Exposures

Conditioning

Animals were conditioned to nose-only exposure tubes for up to 70 minutes. Three conditioning sessions occurred over three days prior to exposure, with the first session lasting 30 minutes, the second 60 minutes and the third 70 minutes. They were monitored closely throughout the conditioning periods and during exposures to assure that they did not experience more than momentary distress.

Exposure System

Aerosols were generated with two compressed air jet Hospitak nebulizers as shown in FIG. 7 above (see Example 3) at a nebulizer pressure of 20 psi. paclitaxel particle suspension formulations of 6.0 mg/mL and 20.0 mg/mL were used for low dose and high dose exposures, respectively. Both formulations were aerosolized separately and aerosols were directed through delivery line into a 32-port nose-only exposure chamber. The rodent inhalation exposures were conducted each for 65 minutes. paclitaxel particle suspension aerosol was generated with a set of two Hospitak compressed airjet nebulizers (used for up to 40 (±1) minutes), then replaced with a second set of two Hospitak nebulizers for remaining exposure duration. Oxygen and temperature were monitored and recorded throughout each inhalation exposure.

Concentration Monitoring

Same as in Example 1

Particle Size Determination

Same as in Example 1

Determination of Dose

Same as in Example 1

Euthanasia and Necropsy

Animals were euthanized at the time points in the study designs above by an intraperitoneal (IP) injection of euthanasia solution.

For 336 Hour Timepoint (and Spare Animals, n=3): During necropsy, blood (for plasma) was collected by cardiac puncture into a K$_2$EDTA tube. A whole lung weight was collected, the left lung was tied off and filled with neutral buffered formalin and saved for potential histopathology. Right lung lobes were individually weighed and snap frozen in liquid nitrogen and stored at −70 to −90° C. for bioanalytical analyses. Additionally, a full gross examination was performed by qualified necropsy personnel. External surfaces of the body, orifices, and the contents of the cranial, thoracic, and abdominal cavities were examined. Lesions were described and recorded using a set of glossary terms for morphology, quantity, shape, color, consistency, and severity.

For all Other Timepoints: During necropsy, blood (for plasma) was collected by cardiac puncture into a K$_2$EDTA tube. A whole lung weight was collected, lung lobes were individually weighed and snap frozen in liquid nitrogen and stored at −70 to −90° C. for bioanalytical analyses. Additionally, a full gross examination was performed by qualified necropsy personnel. External surfaces of the body, orifices, and the contents of the cranial, thoracic, and abdominal cavities were examined. Lesions were described and recorded using a set of glossary terms for morphology, quantity, shape, color, consistency, and severity.

Histopathology

Available fixed tissues were trimmed. Fixed left lung lobes were trimmed to yield a typical toxicologic pathology style section with airways. Tissues were processed routinely, paraffin embedded, sectioned at ~4 μm, mounted, and stained with hematoxylin and eosin (H&E) for microscopic examination. Findings were graded subjectively, semi-quantitatively by a single pathologist experienced in toxicologic pathology on a scale of 1-5 (1=minimal, 2=mild, 3=moderate, 4=marked, 5=severe). The Provantis™ (Instem LSS Ltd., Staffordshire, England) computer software/database was used for histopathology data acquisition, reporting and analysis.

Blood Collection and Processing

Blood collected at necropsy was processed to plasma by centrifugation at a minimum of 1300 g at 4° C. for 10 minutes. Plasma samples were stored at −70 to −90° C. until analysis.

Bioanalytical Analyses

Systemic blood (in the form of plasma from K$_2$EDTA) and lung tissue was assayed via the liquid chromatography-mass spectrometry (LCMS) assay to quantify the amount of paclitaxel as a function of time. In brief the assay utilizes an ultra-performance liquid chromatography tandem mass spectrometry (UPLC-MS/MS) assay to quantify paclitaxel. Samples are extracted via a protein precipitation method and separation is achieved via reversed phase chromatography. Quantification was conducted with a matrix based calibration curve.

Non-compartmental analyses were conducted on data from the plasma and lung tissue concentrations. At a minimum the $C_{max}$, $T_{max}$, AUC and apparent terminal half-life were determined. Other parameters may be determined based on the data.

Results

Clinical Observations, Survival, and Bodyweights

All animals survived to their designated necropsy timepoint. All animals were euthanized within the window intended for each time point.

No abnormal clinical observations were noted through the duration of the study.

Figure 51:
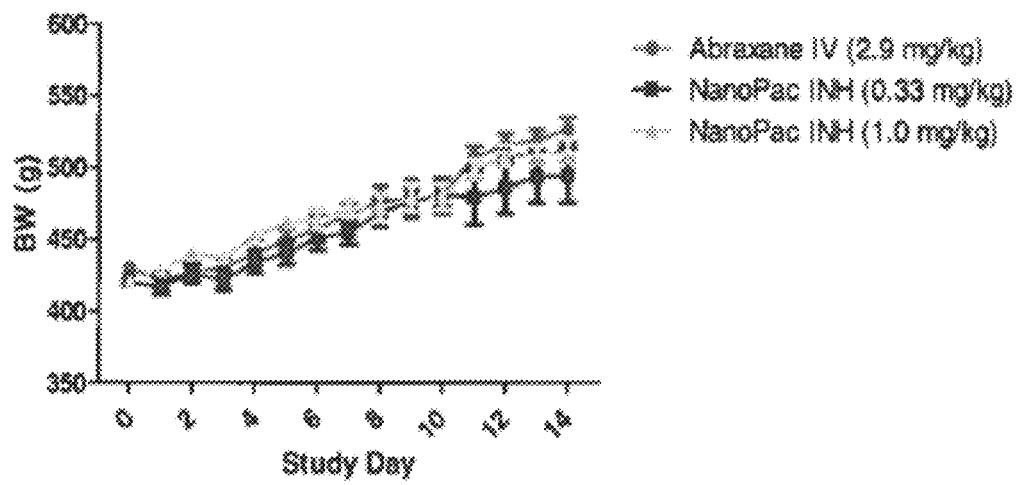
FIG. 51 is a graph of animal body weight over time from inhalation study.
Figure 52:
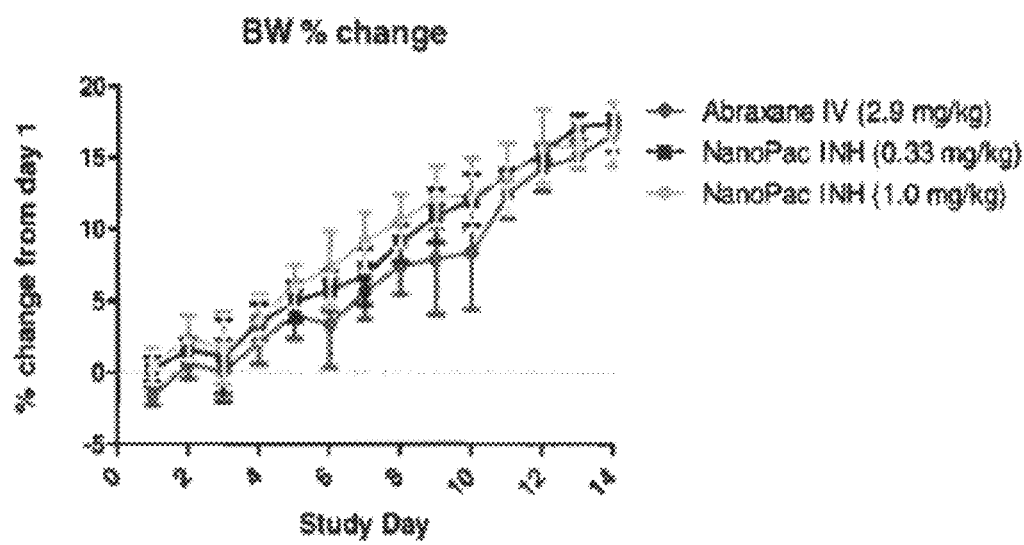
FIG. 52 is a graph of animal body weight change over time from inhalation study.

FIG. 51 and FIG. 52 show the average body weights through the duration of the study and as a percent change from Day 1. All groups gained weight at about the same rate through the course of the study.

ABRAXANE® IV Tail Vein Injections

For the group receiving IV injections of ABRAXANE®, Day 1 bodyweights ranged from 386.1 to 472.8 g, this resulted in ABRAXANE® doses of 2.6-3.2 mg/kg. The average dose (standard deviation) was 2.9 (0.16) mg/kg. Individual ABRAXANE® doses are shown in Table 9.

TABLE 9

Individual ABRAXANE ® Doses

| Subject Name | Day 1 Bodyweight (g) | ABRAXANE ® administered^ (mg) | Dose (mg/kg) |
|---|---|---|---|
| 1001 | 442.1 | 1.25 | 2.8 |
| 1002 | 441.3 | 1.25 | 2.8 |
| 1003 | 425.1 | 1.25 | 2.9 |
| 1004 | 435.7 | 1.25 | 2.9 |
| 1005 | 446.3 | 1.25 | 2.8 |
| 1006 | 412.8 | 1.25 | 3.0 |
| 1007 | 472.8 | 1.25 | 2.6 |
| 1008 | 435.6 | 1.25 | 2.9 |
| 1009 | 400.4 | 1.25 | 3.1 |
| 1010 | 469.8 | 1.25 | 2.7 |
| 1011 | 412.9 | 1.25 | 3.0 |
| 1012 | 456.9 | 1.25 | 2.7 |
| 1013 | 390.7 | 1.25 | 3.2 |
| 1014 | 403.6 | 1.25 | 3.1 |
| 1015 | 414.1 | 1.25 | 3.0 |
| 1016 | 436.0 | 1.25 | 2.9 |
| 1017 | 404.5 | 1.25 | 3.1 |
| 1018 | 424.7 | 1.25 | 2.9 |
| 1019 | 386.1 | 1.25 | 3.2 |
| 1020 | 395.0 | 1.25 | 3.2 |
| 1021 | 414.8 | 1.25 | 3.0 |
| 1022 | 438.5 | 1.25 | 2.9 |
| 1023 | 458.7 | 1.25 | 2.7 |
| 1024 | 425.4 | 1.25 | 2.9 |
| 1025 | 467.3 | 1.25 | 2.7 |
| 1026 | 423.2 | 1.25 | 3.0 |
| 1027 | 414.8 | 1.25 | 3.0 |
| 1028 | 453.5 | 1.25 | 2.8 |
| 1029 | 441.1 | 1.25 | 2.8 |
| 1030 | 458.6 | 1.25 | 2.7 |
| Average | 430.1 | 1.3 | 2.9 |
| Std. Dev. | 24.14 | 0.00 | 0.16 |

^Animals received a maximum IV dose volume of 250 uL of the 5 mg/mL ABRAXANE ® formulation (1.25 mg).

Paclitaxel Particle Exposures

Aerosol Concentration and Particle Size

See: Results—Aerosol Concentration and Particle Size in Example 2.

Oxygen and Temperature
See: Results—Oxygen and Temperature in Example 2.
Deposited Dose
See: Results—Deposited Dose in Example 2.
Necropsy All animals survived to their designated necropsy timepoint. At necropsy animals from each group had minimal to mild, tan discolorations on the lungs (Table 10). Such observations are often associated with inhalation exposures. Other sporadic observations included an enlarged heart (animal #2016) and enlarged tracheobronchial lymph nodes. No other abnormal gross observations were noted at necropsy.

TABLE 10

Summary of Gross Necropsy Observations

|  | ABRAXANE ® IV | Low Dose paclitaxel particle formulation | High Dose paclitaxel particles IH | Naive Control |
|---|---|---|---|---|
| Number on study | 30 | 30 | 30 | 3 |
| No visible lesions | 15 | 14 | 11 | 3 |
| Lungs - Discoloration; Tan; All; Patchy |  |  |  |  |
| Minimal (1) | 0 | 4 | 2 | 0 |
| Mild (2) | 14 | 12 | 15 | 0 |
| Moderate (3) | 1 | 0 | 2 | 0 |

Histopathology

There were no significant abnormalities noted within the trachea and left lungs of the 336 hour (~14 day) post-dosing sacrifice animals examined for this study. Tissues were microscopically indistinguishable from "Spare" animals serving as controls.

Macrophage accumulation was not apparent within the lung sections of treatment animals examined for this study. Some level of increase in alveolar macrophages is very common in inhalation studies as a physiologically normal response to exogenous material deposited in the lung (minor levels can also be a relatively common observation in untreated animals). The apparent absence in inhalation dosed animals in this study may be partly related to the relatively late (336 hour or ~14 day) post-dose timepoint examined histologically.

Bioanalytical and PK Modeling

Figure 53:
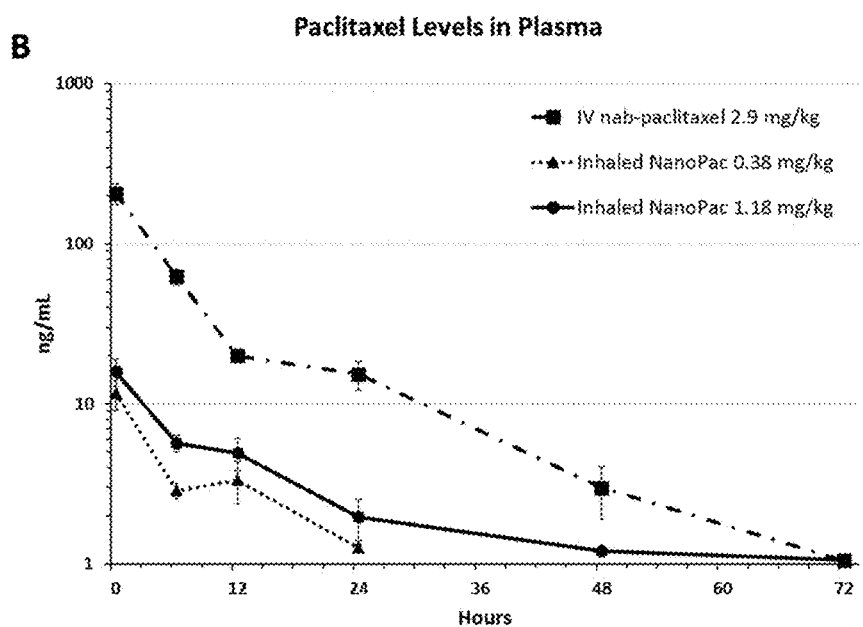
FIG. 53 is a graph of plasma levels of paclitaxel over time from inhalation study.
Figure 54:
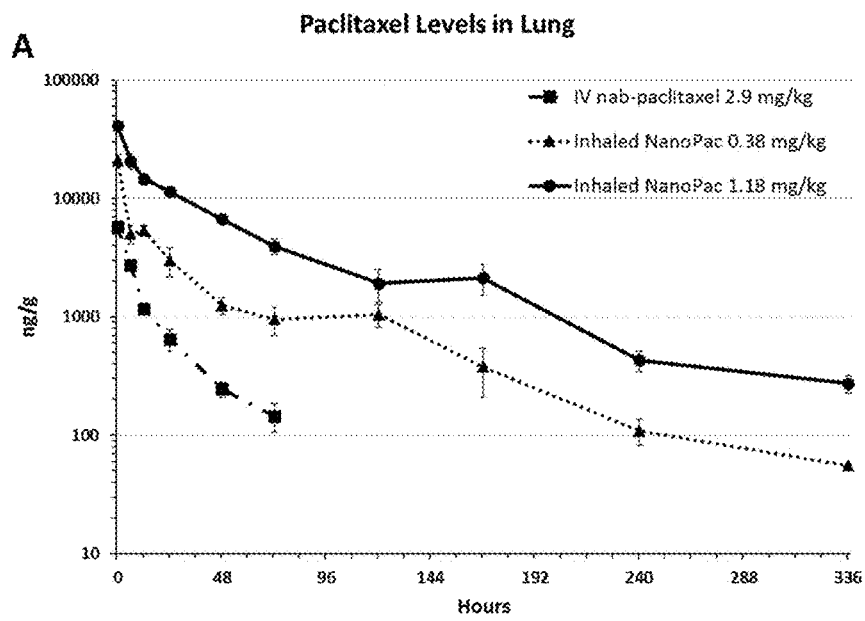
FIG. 54 is a graph of lung tissue levels of paclitaxel over time from inhalation study.

Results are summarized below in Tables 11, 12, and 13, and in FIG. 53 and FIG. 54. The average paclitaxel plasma concentration vs. time and average paclitaxel lung tissue concentration vs. time data was modeled as shown above and the results are shown in Table 14 and 15, respectively.

TABLE 11

Lung and Plasma Bioanalytical Results - ABRAXANE ® IV (IV nab-paclitaxel)

|  |  | Plasma | | Lung Tissue | |
|---|---|---|---|---|---|
| Animal ID | Timepoint (hr) | Concentration (ng/mL) | Mean Concentration Per Timepoint (ng/mL) | Concentration (ng/mL) | Mean Concentration Per Timepoint (ng/mL) |
| 1001 | 0.5 | 153 | 206 | 5850 | 5800 |
| 1002 |  | 205 |  | 5250 |  |
| 1003 |  | 261 |  | 6300 |  |
| 1004 | 6 | 70.5 | 62.2 | 2665 | 2730 |

TABLE 11-continued

Lung and Plasma Bioanalytical Results - ABRAXANE ® IV (IV nab-paclitaxel)

|  |  | Plasma | | Lung Tissue | |
|---|---|---|---|---|---|
| Animal ID | Timepoint (hr) | Concentration (ng/mL) | Mean Concentration Per Timepoint (ng/mL) | Concentration (ng/mL) | Mean Concentration Per Timepoint (ng/mL) |
| 1005 |  | 66.7 |  | 2880 |  |
| 1006 |  | 49.3 |  | 2645 |  |
| 1007 | 12 | 18.9 | 20.0 | 1045 | 1170 |
| 1008 |  | 20 |  | 1145 |  |
| 1009 |  | 21.1 |  | 1320 |  |
| 1010 | 24 | 9.46 | 15.3 | 386 | 647 |
| 1011 |  | 16.3 |  | 825 |  |
| 1012 |  | 20.1 |  | 730 |  |
| 1013 | 48 | 5.08 | 2.98 | 307 | 244 |
| 1014 |  | 1.56 |  | 190 |  |
| 1015 |  | 2.3 |  | 237 |  |
| 1016 | 72 | BQL | 1.05 | 101 | 145 |
| 1017 |  | 1.05 |  | 221 |  |
| 1018 |  | BQL |  | 113 |  |
| 1019 | 120 | BQL | BQL | BQL | BQL |
| 1020 |  | BQL |  | BQL |  |
| 1021 |  | BQL |  | BQL |  |
| 1022 | 168 | BQL | BQL | BQL | BQL |
| 1023 |  | BQL |  | BQL |  |
| 1024 |  | BQL |  | BQL |  |
| 1025 | 240 | BQL | BQL | BQL | BQL |
| 1026 |  | BQL |  | BQL |  |
| 1027 |  | BQL |  | BQL |  |
| 1028 | 336 | BQL | BQL | BQL | BQL |
| 1029 |  | BQL |  | BQL |  |
| 1030 |  | BQL |  | BQL |  |

TABLE 12

Lung and Plasma Bioanalytical Results - Paclitaxel Particle Formulation Low Dose (0.38 mg/kg) IH

|  |  | Plasma | | Lung Tissue | |
|---|---|---|---|---|---|
| Animal ID | Timepoint (hr) | Concentration (ng/mL) | Mean Concentration Per Timepoint (ng/mL) | Concentration (ng/mL) | Mean Concentration Per Timepoint (ng/mL) |
| 2001 | 0.5 | 15.6 | 11.6 | 19450 | 21000 |
| 2002 |  | 12.1 |  | 17700 |  |
| 2003 |  | 7.09 |  | 25850 |  |
| 2004 | 6 | 3.44 | 2.87 | 6700 | 4990 |
| 2005 |  | 2.37 |  | 3945 |  |
| 2006 |  | 2.81 |  | 4325 |  |
| 2007 | 12 | 5.29 | 3.35 | 6200 | 5368 |
| 2008 |  | 2.08 |  | 5550 |  |
| 2009 |  | 2.67 |  | 4355 |  |
| 2010 | 24 | BQL | 1.26 | 2325 | 3008 |
| 2011 |  | 1.16 |  | 2045 |  |
| 2012 |  | 1.36 |  | 4655 |  |
| 2013 | 48 | BQL | BQL | 850 | 1247 |
| 2014 |  | BQL |  | 1530 |  |
| 2015 |  | BQL |  | 1360 |  |
| 2016 | 72 | BQL | BQL | 950 | 950 |
| 2017 |  | BQL |  | 1385 |  |
| 2018 |  | BQL |  | 515 |  |
| 2019 | 120 | BQL | BQL | 1500 | 1045 |
| 2020 |  | BQL |  | 890 |  |
| 2021 |  | BQL |  | 745 |  |
| 2022 | 168 | BQL | BQL | 309 | 377 |
| 2023 |  | BQL |  | 695 |  |
| 2024 |  | BQL |  | 129 |  |
| 2025 | 240 | BQL | BQL | 58 | 109 |
| 2026 |  | BQL |  | 151 |  |

TABLE 12-continued

Lung and Plasma Bioanalytical Results - Paclitaxel
Particle Formulation Low Dose (0.38 mg/kg) IH

| | | Plasma | | Lung Tissue | |
|---|---|---|---|---|---|
| Animal ID | Timepoint (hr) | Concentration (ng/mL) | Mean Concentration Per Timepoint (ng/mL) | Concentration (ng/mL) | Mean Concentration Per Timepoint (ng/mL) |
| 2027 | | BQL | | 117 | |
| 2028 | 336 | BQL | BQL | BQL | 55.5 |
| 2029 | | BQL | | 55.5 | |
| 2030 | | BQL | | BQL | |

TABLE 13

Lung and Plasma Bioanalytical Results - Paclitaxel
Particle Formulation High Dose (1.18 mg/kg) IH

| | | Plasma | | Lung Tissue | |
|---|---|---|---|---|---|
| Animal ID | Timepoint (hr) | Concentration (ng/mL) | Mean Concentration Per Timepoint (ng/mL) | Concentration (ng/mL) | Mean Concentration Per Timepoint (ng/mL) |
| 3001 | 0.5 | 10.8 | 15.9 | 40400 | 41600 |
| 3002 | | 21.3 | | 43800 | |
| 3003 | | 15.6 | | 40600 | |
| 3004 | 6 | 6.56 | 5.69 | 15500 | 20800 |
| 3005 | | 4.35 | | 20400 | |
| 3006 | | 6.15 | | 26500 | |
| 3007 | 12 | 7.14 | 4.95 | 17050 | 14700 |
| 3008 | | 3.47 | | 13500 | |
| 3009 | | 4.23 | | 13550 | |
| 3010 | 24 | 1.47 | 1.96 | 10300 | 11433 |
| 3011 | | 3.11 | | 11700 | |
| 3012 | | 1.31 | | 12300 | |
| 3013 | 48 | 1.21 | 1.21 | 6000 | 6700 |
| 3014 | | BQL | | 7300 | |
| 3015 | | BQL | | 6800 | |
| 3016 | 72 | BQL | 1.06 | 4375 | 3953 |
| 3017 | | 1.06 | | 4735 | |
| 3018 | | BQL | | 2750 | |
| 3019 | 120 | BQL | BQL | 1570 | 1923 |
| 3020 | | BQL | | 1110 | |
| 3021 | | BQL | | 3090 | |
| 3022 | 168 | BQL | BQL | 3395 | 2143 |
| 3023 | | BQL | | 1410 | |
| 3024 | | BQL | | 1625 | |
| 3025 | 240 | BQL | BQL | 271 | 430 |
| 3026 | | BQL | | 448 | |
| 3027 | | BQL | | 570 | |
| 3028 | 336 | BQL | BQL | 233 | 272 |
| 3029 | | BQL | | 367 | |
| 3030 | | BQL | | 216 | |

TABLE 14

Paclitaxel plasma PK modeling results

| Group | Dose (mg/kg) | $C_{max}$ (ng/mL) | $T_{max}$ (hr) | $T_{1/2}$ (hr) | $AUC_{(last)}$ (hr*ng/mL) | $AUC_{D(last)}$ (hr*ng*mg/ mL*kg) |
|---|---|---|---|---|---|---|
| IV | 2.9 | 206 | 0.5 | 8.7 | 1517 | 528 |
| Inhalation | 0.38 | 11.6 | 0.5 | 7.9 | 101 | 264 |
| Inhalation | 1.18 | 15.9 | 0.5 | 8.6 | 228 | 193 |

TABLE 15

Paclitaxel lung tissue PK modeling results

| Group | Dose (mg/kg) | $C_{max}$ (ng/mL) | $T_{max}$ (hr) | $T_{1/2}$ (hr) | $AUC_{(last)}$ (hr*ng/mL) | $AUC_{D(last)}$ (hr*ng*mg/ mL*kg) |
|---|---|---|---|---|---|---|
| IV | 2.9 | 5800 | 0.5 | 19.9 | 62,870 | 23,112 |
| Inhalation | 0.38 | 21,000 | 0.5 | 56.3 | 342,877 | 914,095 |
| Inhalation | 1.18 | 41,600 | 0.5 | 56.0 | 1,155,662 | 997,985 |

The modeling was conducted with WinNonlin based on average plasma or lung tissue concentrations at each time point. The NCA was designed to quantify the exposure (area under the concentration versus time curve [AUC]), time to maximum concentration ($T_{max}$), maximum concentration ($C_{max}$) and when possible apparent terminal half-life ($T_{1/2}$). The half-life within systemic plasma was unchanged for the formulation/doses tested and the half-life within the lung tissue was increased with the paclitaxel particle formulation delivered by inhalation. The exposure to the lung tissue (dose normalized AUC) was increased when delivered as the paclitaxel particle formulation by inhalation.

Collectively the data indicate a significant retention of paclitaxel particles within the lung tissue when delivered via inhalation.

CONCLUSIONS

Ninety (90) male Sprague Dawley rats were exposed to "clinical reference" dose of paclitaxel, ABRAXANE® (paclitaxel protein bound particles for injectable suspension), by intravenous (IV) bolus injection or paclitaxel particle formulation (target dose of 0.37 or 1.0 mg/kg) by nose only inhalation on a single occasion. Three animals (n=3) were euthanatized at ten (10) timepoints from 0.5 to 336 hours post exposure for blood (plasma) and lung tissue collections. Non-compartmental analysis was performed on plasma and lung tissue to identify the duration of detectable amounts of paclitaxel post exposure for each dose group. Animals designated to the 336 hour time point from all groups had right lungs collected for liquid chromatography-mass spectrometry (LCMS) analysis while the left lungs were perfused with 10% neutral buffered formalin (NBF) and retained for potential histopathology. In order to enable comparative histopathology, three spare animals (Native Controls) were also euthanized at the 336 hour timepoint and had lung collections performed in the same manner. Animals designated to all other timepoints had all lungs individually frozen for LCMS analysis.

The inhalation exposure average Paclitaxel aerosol concentration for Low Dose and High Dose paclitaxel particle formulation groups was of 85.64 μg/L and 262.27 μg/L, respectively. The average exposure aerosol concentration was within ±15% of target aerosol concentration which was expected for nebulized inhalation exposures. The particle size distribution was determined in terms of MMAD (GSD) for each paclitaxel particle formulation aerosols using cascade impactor. For 6.0 mg/mL and 20.0 mg/mL paclitaxel particle formulation aerosols the MMAD (GSD) were determined to be 1.8 (2.0) μm and 2.3 (1.9) μm, respectively.

Paclitaxel deposited dose was calculated based on Paclitaxel average aerosol concentration of 85.64 μg/L, average Day 0 group bodyweight of 420.4 g, assumed deposition fraction of 10% and exposure duration of 65 minutes; the average achieved rodent deposited dose was determined to be 0.38 mg/kg for the Low Dose paclitaxel particle formulation group. For the High Dose paclitaxel particle formulation group, paclitaxel average aerosol concentration of 262.27 µg/L, average Day 0 group bodyweight of 420.5 g, assumed deposition fraction of 10% and exposure duration of 65 minutes; the average achieved rodent deposited dose was determined to be 1.18 mg/kg. The recorded oxygen and temperature ranges were 19.8%-20.9% and 20.7° C.-20.8° C., respectively for 6.0 mg/mL paclitaxel particle formulation exposure. For 20.0 mg/mL paclitaxel particle formulation exposure, the recorded oxygen value was 19.8% throughout the exposure and temperature range was 20.7° C.-20.8° C.

For the group receiving IV injections of ABRAXANE®, Day 1 bodyweights ranged from 386.1 to 472.8 g, this resulted in ABRAXANE® doses of 2.6-3.2 mg/kg, with the average group dose being 2.9 mg/kg.

All groups gained weight through the course of the study. No abnormal clinical observations were noted through the duration of the study. All animals survived to their designated necropsy timepoint. All animals were euthanized within the window intended for each time point.

At necropsy, approximately half of the animals from each group had minimal to mild, tan discolorations on the lungs. Such observations are often associated with inhalation exposures. Other transient observations included an enlarged heart (animal #2016) and enlarged tracheobronchial lymph nodes. No other abnormal gross observations were noted at necropsy. Histopathology showed lung and trachea from test and reference article treated rats were within normal limits and indistinguishable from those of naive rats under the conditions of this study.

The NCA was designed to quantify the exposure (area under the concentration versus time curve [AUC]), time to maximum concentration ($T_{max}$), maximum concentration ($C_{max}$) and when possible apparent terminal half-life ($T_{1/2}$).

The hypothesis for the novel paclitaxel particle formulation was that the formulation would result in increased retention of paclitaxel within the lung tissue and reduce the systemic exposure. The half-life within systemic plasma was unchanged for the formulation/doses tested and the half-life within the lung tissue was increased with the paclitaxel particle formulation delivered by inhalation. The exposure to the lung tissue (dose normalized AUC) was increased when delivered as the paclitaxel particle formulation by inhalation.

Collectively the data indicate a significant retention of paclitaxel particles within the lung tissue when delivered via inhalation compared to the IV "clinical reference".

We claim:

1. A method for treating a lung tumor, comprising pulmonary administration to a subject with a lung tumor of an amount effective of a composition comprising taxane particles to treat the lung tumor, wherein the taxane comprises paclitaxel or a pharmaceutically acceptable salt thereof, wherein the taxane particles comprise at least 95% of the taxane and have a mean particle size (number) of between 0.4 µm and 3 µm, wherein the taxane particles have a specific surface area (SSA) of at least 27 m²/g, wherein the taxane particles are present in a suspension comprising the taxane particles and a pharmaceutically acceptable carrier, wherein the suspensions are aerosolized for administration, and aerosol droplets resulting from aerosolization have a mass median aerodynamic diameter (MMAD) of between about 0.5 µm to about 6 µm diameter, wherein the pulmonary administration comprises nebulization, and wherein the nebulization results in pulmonary delivery to the subject of aerosol droplets of the taxane particle suspension.

2. The method of claim 1, wherein the taxane particles have a mean particle size (number) of between 0.4 µm and 2 µm.

3. The method of claim 1, wherein the taxane particles have a mean particle size (number) of between about 0.4 µm and about 1.2 µm.

4. The method of claim 1, wherein the aerosol droplets resulting from aerosolization have a mass median aerodynamic diameter (MMAD) of between about 1 µm to about 3 µm diameter.

5. The method of claim 1, wherein the suspension further comprises-a polysorbate, wherein the polysorbate is present in the suspension at a concentration of between about 0.01% v/v and about 1.5% v/v.

6. The method of claim 1, wherein the pharmaceutically acceptable carrier is saline.

7. The method of claim 5, wherein the polysorbate is polysorbate 80.

8. The method of claim 1, wherein the taxane is present in the suspension at a concentration between about 1 mg/ml and about 40 mg/ml.

9. The method of claim 1, wherein the particles and suspensions thereof are uncoated and exclude lipids, polymers, proteins, polyethoxylated castor oil, and polyethylene glycol glycerides composed of mono-, di- and triglycerides and mono- and diesters of polyethylene glycol.

10. The method of claim 4, wherein the suspension further comprises-a polysorbate, wherein the polysorbate is present in the suspension at a concentration of between about 0.01% v/v and about 1.5% v/v.

11. The method of claim 10, wherein the pharmaceutically acceptable carrier comprises saline.

12. The method of claim 1, wherein the taxane particles have a mean bulk density between about 0.050 g/cm³ and about 0.12 g/cm³.

13. The method of claim 1, wherein the taxane particles are in crystalline form.

14. The method of claim 10, wherein the particles and suspensions thereof are uncoated and exclude lipids, polymers, proteins, polyethoxylated castor oil, and polyethylene glycol glycerides composed of mono-, di- and triglycerides and mono- and diesters of polyethylene glycol.

15. The method of claim 1, wherein the taxane particles reside at the lung tumor site after administration of the composition exposing the tumor to the taxane particles for a sustained amount of time sufficient to stimulate the subject's endogenous immune system resulting in production of tumoricidal cells and infiltration of the tumoricidal cells into the lung tumor at a level sufficient to treat the tumor.

16. The method of claim 15, wherein the sustained amount of time is at least 4 weeks.

17. The method of claim 15, wherein the tumoricidal cells comprise T-cells, B cells, or natural killer (NK) cells, or combinations thereof.

18. The method of claim 1, wherein the composition is administered in two or more separate administrations.

19. The method of claim 18, wherein the composition administered once a week for at least two weeks.

20. The method of claim 18, wherein the composition is administered twice a week for at least one week, wherein the two or more separate administrations are separated by at least one day.

* * * * *